(12) United States Patent
Neelamkavil et al.

(10) Patent No.: US 8,815,876 B2
(45) Date of Patent: Aug. 26, 2014

(54) BICYCLIC HETEROCYCLE DERIVATIVES AND METHODS OF USE THEREOF

(75) Inventors: Santhosh Francis Neelamkavil, Edison, NJ (US); Craig D. Boyle, Branchburg, NJ (US); Bernard R. Neustadt, West Orange, NJ (US); Samuel Chackalamannil, Califon, NJ (US); William J. Greenlee, Teaneck, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 564 days.

(21) Appl. No.: 13/003,716

(22) PCT Filed: Jul. 15, 2009

(86) PCT No.: PCT/US2009/050657
§ 371 (c)(1),
(2), (4) Date: Mar. 15, 2011

(87) PCT Pub. No.: WO2010/009208
PCT Pub. Date: Jan. 21, 2010

(65) Prior Publication Data
US 2011/0166167 A1 Jul. 7, 2011

Related U.S. Application Data

(60) Provisional application No. 61/081,223, filed on Jul. 16, 2008.

(51) Int. Cl.
| | | |
|---|---|---|
| *C07D 519/00* | (2006.01) | |
| *A61K 31/519* | (2006.01) | |
| *A61P 13/12* | (2006.01) | |
| *A61P 3/04* | (2006.01) | |

(52) U.S. Cl.
CPC .................................. *C07D 519/00* (2013.01)
USPC ...... 514/265.1; 544/280; 544/262; 514/262.1

(58) Field of Classification Search
CPC ............................ C07D 519/00; A61K 31/519
USPC ....................................... 544/280; 514/265.1
See application file for complete search history.

(56) References Cited

U.S. PATENT DOCUMENTS

2005/0059650 A1  3/2005  Jones et al.

FOREIGN PATENT DOCUMENTS

| EP | 1338651 | 8/2003 |
|---|---|---|
| WO | 2004/065380 | 8/2004 |
| WO | 2004/076413 A2 | 9/2004 |
| WO | 2004/076413 A3 | 9/2004 |
| WO | 2008/008887 | 1/2008 |
| WO | 2008/130584 | 10/2008 |
| WO | 2008/137435 | 11/2008 |
| WO | 2008/137436 | 11/2008 |
| WO | 2009/012275 | 1/2009 |
| WO | 2009/055331 | 4/2009 |
| WO | 2009/143049 | 11/2009 |
| WO | 2010/009195 | 1/2010 |
| WO | 2010/009207 | 1/2010 |
| WO | 2010/114958 | 10/2010 |
| WO | 2011/053686 | 5/2011 |
| WO | 2011/062885 | 5/2011 |
| WO | 2011/066137 | 6/2011 |

OTHER PUBLICATIONS

Int'l Search Report of PCT/US2009/050657, dated Nov. 9, 2009.
Int'l Preliminary Report on Patentability of PCT/US2009/050657, dated Jan. 18, 2011.

*Primary Examiner* — Susanna Moore
(74) *Attorney, Agent, or Firm* — Anna L. Cocuzzo; Catherine D. Fitch

(57) ABSTRACT

The present invention relates to Bicyclic Heterocycle Derivatives, compositions comprising a Bicyclic Heterocycle Derivative, and methods of using the Bicyclic Heterocycle Derivatives for treating or preventing obesity, diabetes, a diabetic complication, a metabolic disorder, a cardiovascular disease or a disorder related to the activity of a G protein-coupled receptor (GPCR) in a patient. The compounds are of structure (I).

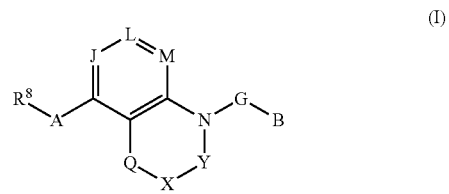

(I)

16 Claims, No Drawings

BICYCLIC HETEROCYCLE DERIVATIVES AND METHODS OF USE THEREOF

CROSS-REFERENCE TO RELATED APPLICATIONS

This application is a U.S. National Phase application under 35 U.S.C. §371 of PCT/US2009/050657, filed Jul. 15, 2009, which claims priority from U.S. provisional application 61/081,223, filed Jul. 16, 2008.

FIELD OF THE INVENTION

The present invention relates to Bicyclic Heterocycle Derivatives, compositions comprising a Bicyclic Heterocycle Derivative, and methods of using the Bicyclic Heterocycle Derivatives for treating or preventing obesity, diabetes, a diabetic complication, a metabolic disorder, a cardiovascular disease or a disorder related to the activity of a G protein-coupled receptor (GPCR) in a patient.

BACKGROUND OF THE INVENTION

Although a number of receptor classes exist in humans, by far the most abundant and therapeutically relevant is represented by the G protein-coupled receptor (GPCR or GPCRs) class. It is estimated that there are some 100,000 genes within the human genome, and of these, approximately 2% or 2,000 genes, are estimated to code for GPCRs. Receptors, including GPCRs, for which the endogenous ligand has been identified are referred to as "known" receptors, while receptors for which the endogenous ligand has not been identified are referred to as "orphan" receptors. GPCRs represent an important area for the development of pharmaceutical products, as evidenced by the fact that pharmaceutical products have been developed from approximately 20 of the 100 known GPCRs. This distinction is not merely semantic, particularly in the case of GPCRs. Thus, the orphan GPCRs are to the pharmaceutical industry what gold was to California in the late 19th century—an opportunity to drive growth, expansion, enhancement and development.

GPCRs share a common structural motif. All these receptors have seven sequences of between 22 to 24 hydrophobic amino acids that form seven alpha helices, each of which spans the membrane (each span is identified by number, transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., *Life Sciences* 43, 1095 (1988). Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to produce a biological response. Changing the receptor conformation to the active state allows linkage to the transduction pathway (via the G-protein) and produces a biological response. A receptor can be stabilized in an active state by an endogenous ligand or a compound such as a drug.

Modulation of G-protein coupled receptors has been well-studied for controlling various metabolic disorders. Small molecule modulators of the receptor GPR119, a G-protein coupled-receptor described in, for example, GenBank (see, e.g., accession numbers XM.sub.—066873 and AY288416), have been shown to be useful for treating or preventing certain metabolic disorders. GPR119 is a G protein-coupled receptor that is selectively expressed on pancreatic beta cells. GPR119 activation leads to elevation of a level of intracellular cAMP, consistent with GPR119 being coupled to Gs. Agonists to GPR119 stimulate glucose-dependent insulin secretion in vitro and lower an elevated blood glucose level in vivo. See, e.g., international Application Nos, WO 04/065380, WO 04/076413, and EP 1338651, the disclosure of each of which is herein incorporated by reference in its entirety.

U.S. Ser. No. 10/890,549 discloses pyrazolo[3,4-d]pyrimidine ethers and related compounds as modulators of the GPR119 receptor that are useful for the treatment of various metabolic-related disorders such as type I diabetes, type II diabetes, inadequate glucose tolerance, insulin resistance, hyperglycemia, hyperlipidemia, hypertriglyceridemia, hypercholesterolemia, dyslipidemia or syndrome X. The compounds are also reported as being useful for controlling weight gain, controlling food intake, and inducing satiety in mammals. The promising nature of these GPCR modulators indicates a need in the art for additional small molecule GPCR modulators with improved efficacy and safety profiles. This invention addresses that need.

SUMMARY OF THE INVENTION

In one aspect, the present invention provides compounds of Formula (I):

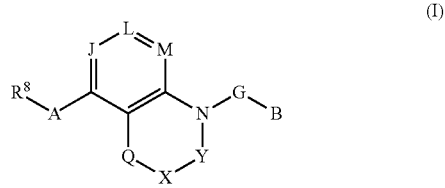

and pharmaceutically acceptable salts, solvates, esters and prodrugs thereof, wherein:

A is alkylene, -(alkylene)$_t$-O-(alkylene)$_t$-, -(alkylene)$_t$-C(O)-(alkylene)$_t$-, -(alkylene)$_t$-N(R$^{12}$)-(alkylene)$_t$- or -(alkylene)$_t$-S(O)$_n$-(alkylene)$_t$-;

B is:

[chemical structure]

G is a bond, -alkylene-, -(alkylene)$_t$-C(O)-(alkylene)$_t$-, -(alkylene)$_t$-S(O)$_q$-(alkylene)$_t$-, -alkylene-O-(alkylene)$_t$-, -alkylene-S-(alkylene)$_t$- or -alkylene-N(R$^7$)-(alkylene)$_t$-;

J is —C(R$^{11}$)— or —N—;
L is —C(R$^{11}$)— or —N—;
M is —C(R$^{11}$)— or —N—;
W is a bond, alkylene, —C(O)—, —C(O)—O—, —S(O)$_2$—, —S(O)$_2$—N(R$^{10}$)— or —C(O)—N(R$^{10}$)—;
Q is a bond, —C(R$^7$)$_2$—, —O—, —S(O)$_n$— or —N(R$^7$)—, such that when Q is —O—, —S(O)$_n$— or —N(R$^7$)—, then group —X—Y— is —C(R$^7$)$_2$C(R$^7$)$_2$—, —C(R$^7$)$_2$—C(O)—, —C(R$^7$)$_2$—S(O)$_n$—, —C(R$^7$)═C(R)— or —C(R$^7$)═N—;
the group —X—Y— is —C(R$^7$)$_2$C(R$^7$)$_2$—, —C(R$^7$)$_2$C(O)—, —N(R$^7$)C(O)—, —OC(O)—, —C(R$^7$)═C(R$^7$)—, —C(R$^7$)═N—, —N═C(R$^7$)—, —C(O)—N(R$^7$)—, —C(O)—C(R$^7$)$_2$—, —S(O)$_n$—C(R$^7$—C(R$^7$)$_2$—S(O)$_n$— or —N═N—;
Z is a bond, —C(O)—, —C═NOR$^2$, —C═C(R$^{14}$)$_2$, —C(R$^1$)$_2$—, —O—, —N(R$^{10}$)— or —S(O)$_n$—;

each occurrence of R$^1$ is independently H, alkyl, cycloalkyl, halo or —OR$^7$; or any two geminal R$^1$ groups, together with the common carbon atom to which they are attached, can join to form a spirocyclic 3- to 6-membered cycloalkyl group, a spirocyclic 3- to 6-membered heterocycloalkyl group or a spirocyclic 3- to 6-membered heterocycloalkenyl group; or any two R$^1$ groups present on adjacent carbon atoms, together with the adjacent carbon atoms to which they are attached, can join to form a fused 3- to 6-membered cycloalkyl group, a fused 3- to 6-membered heteroaryl group, a fused 3- to 6-membered heterocycloalkyl group or a fused aryl group; and wherein an alkyl group can be unsubstituted or optionally substituted with one or more of the following groups: —O-alkyl, —OH or —N(R$^4$)$_7$; and wherein an optional endocyclic double bond can be present between any two adjacent ring carbon atoms;

each occurrence of R$^2$ is independently H, alkyl, halo or —OR$^7$;

R$^3$ is alkyl, alkenyl, alkynyl, haloalkyl, -alkylene-O-(alkylene)$_t$-aryl, -alkylene-S-aryl, -alkylene-N(R$^4$)C(O)O-alkyl, —CH(cycloalkyl)$_2$, —CH(heterocycloalkyl)$_2$, -(alkylene)$_t$-aryl, -(alkylene)$_t$-cycloalkyl, -(alkylene)$_t$-cycloalkenyl, -(alkylene)$_t$-heterocycloalkyl, -(alkylene)$_t$-heterocycloalkenyl or -(alkylene)$_t$-heteroaryl, wherein an aryl, cycloalkyl, cycloalkenyl, heterocycloalkyl, heterocycloalkenyl or heteroaryl group can be unsubstituted or optionally substituted with R$^9$;

each occurrence of R$^4$ is independently H or alkyl;

each occurrence of R$^7$ is independently H or alkyl;

R$^8$ is aryl, heteroaryl, heterocycloalkenyl, cycloalkenyl, cycloalkyl or heterocycloalkyl, any of which can be optionally substituted with R$^9$;

R$^9$ represents from 1 to 4 optional substituents, which can be the same or different, and which are selected from alkenyl, alkynyl, halo, haloalkyl, —CN, —NO$_2$, —O-(alkylene)$_t$-R$^{13}$, —S-(alkylene)$_t$-R$^{13}$, —N(R$^{13}$)-(alkylene)$_t$-R$^{13}$, -(alkylene)$_t$-R$^{13}$, —C(O)-(alkylene)$_t$-R$^3$, —C(O)O-(alkylene)$_t$-R$^{13}$, —N(R$^7$)C(O)-(alkylene)$_t$-R$^{13}$, —C(O)N(R$^7$)-(alkylene)$_t$-R$^{13}$, —OC(O)-(alkylene)$_t$-R$^{13}$, —N(R$^7$)C(O)N(R$^7$)-(alkylene)$_t$-R$^{13}$, —N(R$^7$)C(O)O-(alkylene)$_t$-R$^{13}$, —S(O)-(alkylene)$_t$-R$^{13}$ or —S(O)$_2$(alkylene)$_t$-R$^{13}$;

R$^{10}$ is H, alkyl, aryl, or —C(O)OR$^4$;

each occurrence of R$^{11}$ is independently H, alkyl, aryl, cycloalkyl, heterocycloalkyl, heteroaryl, —N(R$^7$)$_2$ or halo;

R$^{12}$ is H, alkyl or aryl;

each occurrence of R$^{13}$ is independently H, haloalkyl, aryl, cycloalkyl, cycloalkenyl, heterocycloalkyl, heterocycloalkenyl or heteroaryl;

each occurrence of R$^{14}$ is independently H, alkyl or aryl, or both R$^{14}$ groups, and the carbon atom to which they are attached, combine to form a cycloalkyl or heterocycloalkyl group;

each occurrence of m is independently 1 or 2;
each occurrence of n is independently 0, 1 or 2;
p is 0, 1 or 2;
q is 0, 1 or 2;
r is 0, 1 or 2;
s is 0, 1 or 2;
each occurrence of t is independently 0 or 1; and
u is 0, 1 or 2.

In another aspect, the present invention provides compounds of Formula (II):

[chemical structure (II)]

and pharmaceutically acceptable salts, solvates, esters and prodrugs thereof,
wherein:

A is alkylene, -(alkylene)$_t$-O-(alkylene)$_t$-, -(alkylene)$_t$-C(O)-(alkylene)$_t$-, -(alkylene)$_t$-N(R$^{12}$)-(alkylene)$_t$- or -(alkylene)$_t$-S(O)$_n$-(alkylene)$_t$-;

B is:

[chemical structure]

G is a bond, -alkylene-, -(alkylene)$_t$-C(O)-(alkylene)$_t$-, -(alkylene)$_t$-S(O)$_q$-(alkylene)$_t$-, -alkylene-O-(alkylene)$_t$-, -alkylene-S-(alkylene)$_t$- or -alkylene-N(R$^7$)-(alkylene)$_t$-;

J is —C(R$^{11}$)— or —N—;
L is —C(R$^{11}$)— or —N—;
M is —C(R$^{11}$)— or —N—;

W is a bond, alkylene, —C(O)—, —C(O)—O—, —S(O)$_2$—, —S(O)$_2$—N(R$^{10}$)— or —C(O)—N(R$^{10}$)—;

Q is a bond, —C(R$^7$)$_2$—, —O—, —S(O)$_n$— or —N(R$^7$)—, such that when Q is —O—, —S(O)$_n$— or —N(R$^7$)—, then group —X—Y— is —C(R$^7$)$_2$C(R$^7$)$_2$—, —C(R$^7$)$_2$—C(O)—, —C(R$^7$)$_2$—S(O)$_n$—, —C(R$^7$)=C(R$^7$)— or —C(R$^7$)=N—;

the group —X—Y— is —C(R$^7$)$_2$C(R$^7$)$_2$—, —C(R$^7$)$_2$C(O)—, —N(R$^7$)C(O)—, —OC(O)—, —C(R$^7$)=C(R$^7$)—, —N=C(R$^7$)—, —C(O)—N(R$^7$)—, —C(O)—C(R$^7$)$_2$—, —S(O)$_n$—C(R$^7$)$_2$—, —C(R$^7$)$_2$—S(O)$_n$— or —N=N—;

each occurrence of R$^1$ is independently H, cycloalkyl, halo or —OR$^7$; or any two geminal R$^1$ groups, together with the common carbon atom to which they are attached, can join to form a spirocyclic 3- to 6-membered cycloalkyl group, a spirocyclic 3- to 6-membered heterocycloalkyl group or a spirocyclic 3- to 6-membered heterocycloalkenyl group; or any two R$^1$ groups present on adjacent carbon atoms, together with the adjacent carbon atoms to which they are attached, can join to form a fused 3- to 6-membered cycloalkyl group, a fused 3- to 6-membered heteroaryl group, a fused 3- to 6-membered heterocycloalkyl group or a fused aryl group; and wherein an alkyl group can be unsubstituted or optionally substituted with one or more of the following groups: —O-alkyl, —OH or —N(R$^4$)$_2$; and wherein an optional endocyclic double bond can be present between any two adjacent ring carbon atoms;

R$^3$ is alkyl, alkenyl, alkynyl, haloalkyl, -alkylene-O-(alkylene)$_t$-aryl, -alkylene-S-aryl, -alkylene-N(R$^4$)C(O)O-alkyl, —CH(cycloalkyl)$_2$, —CH(heterocycloalkyl)$_2$, -(alkylene)$_t$-aryl, -(alkylene)$_t$-cycloalkyl, -(alkylene)$_t$-cycloalkenyl, -(alkylene)$_t$-heterocycloalkyl, -(alkylene)$_t$-heterocycloalkenyl or -(alkylene)$_t$-heteroaryl, wherein an aryl, cycloalkyl, cycloalkenyl, heterocycloalkyl, heterocycloalkenyl or heteroaryl group can be unsubstituted or optionally substituted with R$^9$;

each occurrence of R$^4$ is independently H or alkyl;
each occurrence of R$^7$ is independently H or alkyl;
R$^8$ is aryl, heteroaryl, cycloalkyl or heterocycloalkyl, any of which can be optionally substituted with R$^9$;
R$^9$ represents from 1 to 4 optional substituents, which can be the same or different, and which are selected from alkenyl, alkynyl, halo, haloalkyl, —CN, —NO$_2$, —O-(alkylene)$_t$-R$^{13}$, —S-(alkylene)$_t$-R$^{13}$, —N(R$^{13}$)-(alkylene)$_t$-R$^{13}$, -(alkylene)$_t$-R$^{13}$, —C(O)-(alkylene)$_t$-R$^{13}$, —C(O)O-(alkylene)$_t$-R$^{13}$, —N(R$^7$)C(O)-(alkylene)$_t$-R$^{13}$, —C(O)N(R$^7$)-(alkylene)$_t$-R$^{13}$, —OC(O)-(alkylene)$_t$-R$^{13}$, —N(R$^7$)C(O)N(R$^7$)-(alkylene)$_t$-R$^{13}$, —N(R$^7$)C(O)O-(alkylene)$_t$-R$^{13}$, —S(O)-(alkylene)$_t$-R$^{13}$ or —S(O)$_2$(alkylene)$_t$-R$^{13}$;

R$^{10}$ is H, alkyl, aryl, or —C(O)OR$^4$;
each occurrence of R$^{11}$ is independently H, alkyl, aryl, cycloalkyl, heterocycloalkyl, heteroaryl, —N(R$^7$)$_2$ or halo;
R$^{12}$ is H, alkyl or aryl;
each occurrence of R$^{13}$ is independently H, haloalkyl, aryl, cycloalkyl, cycloalkenyl, heterocycloalkyl, heterocycloalkenyl or heteroaryl;

each occurrence of m is independently 1 or
each occurrence of n is independently 0, 1 or 2;
p is an integer ranging from 0 to 3, such that the sum of p and q is at least 1;
q is an integer ranging from 0 to 3;
r is an integer ranging from 0 to 3, such that the sum of r and s is at least 1;
s is an integer from 0 to 3; and
each occurrence of t is independently 0 or 1.

In another aspect, the present invention provides compounds of Formula (III):

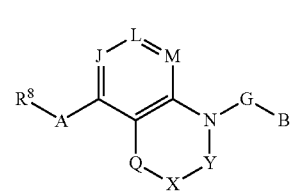

(III)

and pharmaceutically acceptable salts, solvates, esters and prodrugs thereof,
wherein:

A is alkylene, -(alkylene)$_t$-O-(alkylene)$_t$-, -(alkylene)$_t$-C(O)-(alkylene)$_t$-, -(alkylene)$_t$-N(R$^{12}$)-(alkylene)$_t$- or -(alkylene)$_t$-S(O)$_n$-(alkylene)$_t$-;

B is:

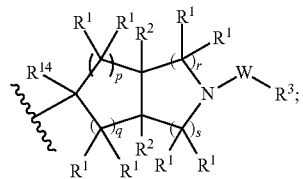

G is a bond, -alkylene-, -(alkylene)$_t$-C(O)-(alkylene)$_t$-, -(alkylene)$_t$-S(O)$_q$-(alkylene)$_t$-, -alkylene-O-(alkylene)$_t$-, -alkylene-S-(alkylene)$_t$- or -alkylene-N(R$^7$)-(alkylene)$_t$-;

J is —C(R$^{11}$)— or —N—;
L is —C(R$^{11}$)— or —N—;
M is —C(R$^{11}$)— or —N—;
W is a bond, alkylene, —C(O)—, —C(O)—O—, —S(O)$_2$—, —S(O)$_2$—N(R$^{10}$)— or —C(O)—N(R$^{10}$)—;

Q is a bond, —C(R$^7$)$_2$—, —O—, —S(O)$_n$— or —N(R$^7$)—, such that when Q is —O—, —S(O)$_n$— or —N(R$^7$)—, then group —X—Y— is —C(R$^7$)$_2$C(R$^7$)$_2$—, —C(R$^7$)$_2$—C(O)—, —C(R$^7$)$_2$—S(O)$_n$—, —C(R$^7$)=C(R$^7$)— or —C(R$^7$)=N—;

the group —X—Y— is —C(R$^7$)$_2$C(R$^7$)$_2$—, —C(R$^7$)$_2$C(O)—, —N(R$^7$)C(O)—, —OC(O)—, —C(R$^7$)=C(R$^7$)—, —C(R$^7$)=N—, —N=C(R$^7$)—, —C(O)—N(R$^7$)$_2$—, —C(O)—C(R$^7$)$_2$—, —S(O)$_n$—C(R$^7$)$_2$—, —C(R$^7$)$_2$—S(O)$_n$— or —N=N—;

each occurrence of R$^1$ is independently H, alkyl, cycloalkyl, halo or —OR$^7$; or any two geminal R$^1$ groups, together with the common carbon atom to which they are attached, can join to form a spirocyclic 3- to 6-membered cycloalkyl group, a spirocyclic 3- to 6-membered heterocycloalkyl group or a spirocyclic 3- to 6-membered heterocycloalkenyl group; or any two R$^1$ groups present on adjacent carbon atoms, together with the adjacent carbon atoms to which they are attached, can join to form a fused 3- to 6-membered cycloalkyl group, a fused 3- to 6-membered heteroaryl group, a fused 3- to 6-membered heterocycloalkyl group or a fused aryl group; and wherein an alkyl group can be unsubstituted or optionally substituted with one or more of the following groups: —O-alkyl, —OH or —N(R$^4$)$_2$; and wherein an optional endocyclic double bond can be present between any two adjacent ring carbon atoms;

each occurrence of R$^2$ is independently H, alkyl, halo or —OR$^7$;

$R^3$ is alkyl, alkenyl, alkynyl, haloalkyl, -alkylene-O-(alkylene)$_t$-aryl, -alkylene-S-aryl, -alkylene-N($R^4$)C(O)O-alkyl, —CH(cycloalkyl)$_2$, —CH(heterocycloalkyl)$_2$, -(alkylene)$_t$-aryl, -(alkylene)$_t$-cycloalkyl, -(alkylene)$_t$-cycloalkenyl, -(alkylene)$_t$-heterocycloalkyl, -(alkylene)$_t$-heterocycloalkenyl or -(alkylene)$_t$-heteroaryl, wherein an aryl, cycloalkyl, cycloalkenyl, heterocycloalkyl, heterocycloalkenyl or heteroaryl group can be unsubstituted or optionally substituted with $R^9$;

each occurrence of $R^4$ is independently H or alkyl;

each occurrence of $R^7$ is independently H or alkyl;

$R^8$ is aryl, heteroaryl, cycloalkyl or heterocycloalkyl, any of which can be optionally substituted with $R^9$;

$R^9$ represents from 1 to 4 optional substituents, which can be the same or different, and which are selected from alkenyl, alkynyl, halo, haloalkyl, —CN, —NO$_2$, —O-(alkylene)$_t$-$R^{13}$, —S-(alkylene)$_t$-$R^{13}$, —N($R^{13}$)-(alkylene)$_t$-$R^{13}$, -(alkylene)$_t$-$R^{13}$, —C(O)-(alkylene)$_t$-$R^{13}$, —C(O)O-(alkylene)$_t$-$R^{13}$, —N($R^7$)C(O)-(alkylene)$_t$-$R^{13}$, —C(O)N($R^7$)-(alkylene)$_t$-$R^{13}$, —OC(O)-(alkylene)$_t$-$R^{13}$, —N($R^7$)C(O)N($R^7$)-(alkylene)$_t$-$R^{13}$, —N($R^7$)C(O)O-(alkylene)$_t$-$R^{13}$, —S(O)-(alkylene)$_t$-$R^{13}$ or —S(O)$_2$(alkylene)$_t$-$R^{13}$;

each occurrence of $R^{11}$ is independently H, alkyl, aryl, cycloalkyl, heterocycloalkyl, heteroaryl, —N($R^7$)$_2$ or halo;

$R^{12}$ is H, alkyl or aryl;

each occurrence of $R^{13}$ is independently H, haloalkyl, aryl, cycloalkyl, cycloalkenyl, heterocycloalkyl, heterocycloalkenyl or heteroaryl;

each occurrence of m is independently 1 or 2;

each occurrence of n is independently 0, 1 or 2;

p is 0, 1 or 2;

q is 0, 1 or 2;

r is 0, 1 or 2;

s is 0, 1 or 2; and each occurrence of t is independently 0 or 1.

The compounds of formulas (I), (II) and (III) and pharmaceutically acceptable salts, solvates, esters or prodrugs thereof (referred to collectively herein as the "Bicyclic Heterocycle Derivatives") can be useful for treating or preventing obesity, diabetes, a diabetic complication, metabolic syndrome, or a disorder related to the activity of a GPCR, or a cardiovascular disease (each being a "Condition") in a patient.

Also provided by the invention are methods for treating or preventing a Condition in a patient, comprising administering to the patient an effective amount of one or more Bicyclic Heterocycle Derivatives.

The present invention further provides compositions comprising an effective amount of one or more Bicyclic Heterocycle Derivatives or a pharmaceutically acceptable salt, solvate, ester or prodrug thereof, and a pharmaceutically acceptable carrier. The compositions can be useful for treating or preventing a Condition in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides Bicyclic Heterocycle Derivatives of Formulas (I), (II) and (III), compositions comprising one or more Bicyclic Heterocycle Derivatives, and methods of using the Bicyclic Heterocycle Derivatives for treating or preventing a Condition in a patient.

Definitions and Abbreviations

As used above, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "obesity-related disorder" as used herein refers to: (i) disorders which result from a patient having a BMI of 25 or greater; and (ii) eating disorders and other disorders associated with excessive food intake. Non-limiting examples of an obesity-related disorder include edema, shortness of breath, sleep apnea, skin disorders and high blood pressure.

The term "metabolic syndrome" as used herein, refers to a set of risk factors that make a patient more susceptible to cardiovascular disease and/or type 2 diabetes. A patient is said to have metabolic syndrome if the patient simultaneously has three or more of the following five risk factors:

1) central/abdominal obesity as measured by a waist circumference of greater than 40 inches in a male and greater than 35 inches in a female;
2) a fasting triglyceride level of greater than or equal to 150 mg/dL;
3) an HDL cholesterol level in a male of less than 40 mg/dL, or in a female of less than 50 mg/dL;
4) blood pressure greater than or equal to 130/85 mm Hg; and
5) a fasting glucose level of greater than or equal to 110 mg/dL.

The term "effective amount" as used herein, refers to an amount of Bicyclic Heterocycle Derivative and/or an additional therapeutic intent, or a composition thereof that is effective in producing the desired therapeutic, ameliorative, inhibitory or preventative effect when administered to a patient suffering from a Condition. In the combination therapies present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group which may be straight or branched and which contains from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is unsubstituted. In another embodiment, an alkyl group is linear. In another embodiment, an alkyl group is branched.

The term "alkenyl," as used herein, refers to an aliphatic hydrocarbon group containing at least one carbon-carbon double bond and which may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkenyl group is unsubstituted.

The term "alkynyl," as used herein, refers to an aliphatic hydrocarbon group containing at least one carbon-carbon triple bond and which may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. Non-limiting examples of aryl groups include phenyl and naphthyl. In one embodiment, an aryl group is unsubstituted. In another embodiment, an aryl group is phenyl.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 5 to about 7 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment a cycloalkyl group is unsubstituted.

The term "cycloalkenyl," as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted. In another embodiment, a cycloalkenyl group is a 6-membered cycloalkenyl. In another embodiment, a cycloalkenyl group is a 5-membered cycloalkenyl.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heterocycloalkyl," as used herein, refers to a non-aromatic saturated monocyclic or multicyclic rang system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

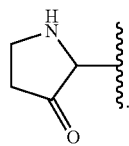

In one embodiment, a heterocycloalkyl group is unsubstituted. In another embodiment, a heterocycloalkyl group is a 5-membered heterocycloalkyl. In another embodiment, a heterocycloalkyl roup is a 6-membered heterocycloalkyl.

The term "heterocycloalkenyl," as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl gout) has from 5 to 10 ring atoms. In another embodiment, a heterocloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. An illustrative example of such a heterocycloalkenyl group is:

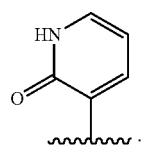

In one embodiment, a heterocycloalkenyl group is unsubstituted. In another embodiment, a heterocycloalkenyl group is a 6-membered heterocycloalkenyl. In another embodiment, a heterocycloalkenyl group is a 5-membered heterocycloalkenyl.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkyl-aryl, -aryl-alkyl, -alkylene-heteroaryl, -alkenylene-heteroaryl, -alkynylene-heteroaryl, hydroxy, hydroxyalkyl, haloalkyl, —O-alkyl, —O-haloalkyl, -alkylene-O-alkyl, —O-aryl, aralkoxy, acyl, aroyl, halo, nitro, cyano, carboxy, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), $Y_1Y_2N$—, $Y_1Y_2N$-alkyl-, $Y_1Y_2NC(O)$—, $Y_1Y_2NS(O)_2$— and —S(O)$_2$NY$_1$Y$_2$, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy —C(CH$_3$)$_2$— and the like which form moieties such as, for example:

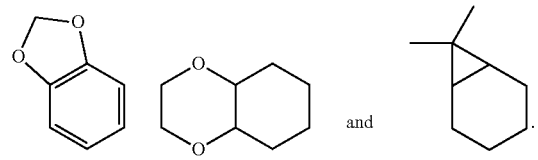

"Halo" means —F, —Cl, —Br or —I. In one embodiment, halo refers to —F, —Cl or —Br.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g. from a reaction mixture), or natural source or combination thereof. Thus, the term "purified", "in purified form" or "in isolated and purified form" for a compound refers to the physical state of the compound after being obtained from a purification process or processes described herein or well known to the skilled artisan (e.g., chromatography, recrystallization and the like) in sufficient purity to be characterizable by standard analytical techniques described herein or well known to the skilled artisan.

It should also be noted that any carbon as well as heteroatom with unsatisfied valences in the text, schemes, examples and Tables herein assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a Bicyclic Heterocycle Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Bicyclic Heterocycle Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxmethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a Bicyclic Heterocycle Derivative contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a Bicyclic Heterocycle Derivative incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Bicyclic Heterocycle Derivatives can form salts which are also within the scope of this invention. Reference to a Bicyclic Heterocycle Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Bicyclic Heterocycle Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the compounds of the Formula (I) may be formed, for example, by reacting a Bicyclic Heterocycle Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts, Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, choline, t-butyl amine, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the Bicyclic Heterocycle Derivatives may be atropisomers (e.g., substituted biaryls) and are considered as part of this invention. Enantiomers can also be separated by use of chiral HPLC column.

It is also possible that the Bicyclic Heterocycle Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a Bicyclic Heterocycle Derivative incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Bicyclic Heterocycle Derivatives of the present invention (e.g., those labeled with $^3H$ and $^{14}C$) are useful in compound and/or substrate tissue distribution assays. In one embodiment, tritiated (i.e., $^3H$) and carbon-14 (i.e., $^{14}C$) isotopes are employed for their ease of preparation and detectability. In another embodiment, substitution with heavier isotopes such as deuterium (i.e., $^2H$) may afford certain therapeutic advantages resulting from greater metabolic stability (e.g., increased in vivo half life or reduced dosage requirements). In one embodiment, one or more hydrogen atoms of a Bicyclic Heterocycle Derivative of the present invention is replaced by a deuterium atom. Isotopically labelled Bicyclic Heterocycle Derivatives of the present invention can generally be prepared by following procedures analogous to those disclosed in the Schemes and/or in the Examples herein below, by substituting an appropriate isotopically labelled reagent for a non-isotopically labelled reagent.

Polymorphic forms of the Bicyclic Heterocycle Derivatives, and of the salts, solvates, hydrates, esters and prodrugs of the Bicyclic Heterocycle Derivatives, are intended to be included in the present invention.

The following abbreviations are used below and have the following meanings: AcOH is acetic acid, Boc or BOC is —C(O)O-(t-butyl), n-BuLi is n-butyllithium, t-butyl is tertiary butyl, DAST is diethylaminosulfur trichloride, dba is dibenzylidene acetone, DCE is dichloroethane, DCM is dichloromethane, DIAD is diisopropylazodicarboxylate, DIEA is diisopropylethylamine, DMEM is Dulbecco's modified eagle medium, DMF is N,N-dimethylformamide, DMSO is dimethylsulfoxide, dppf is 1,1'-bis(diphenylphosphino)ferrocene, EDC is 1-(dimethylaminopropyl)-3-ethylcarbodiimide, EtOAc is ethyl acetate, EtOH is ethanol, $Et_3N$ is triethylamine, $EtNH_2$ is ethylamine, HOBt is 1-hydroxybenzotriazole, LCMS is liquid chromatography mass spectrometry, LDA is lithium diisopropylamide, mCPBA is meta-chloroperoxybenzoic acid, MeOH is methanol, NaOEt is sodium ethoxide, NaOtBu is sodium t-butoxide, NMM is n-methylmorpholine, NMR is nuclear magnetic resonance, Ph is phenyl, PhMe is toluene, PS-EDC is polystyrene functionalized with EDC—available from Polymer Laboratories, PS-DIEA is polystyrene functionalized with disopropylethylamine, TBAF is tetra-n-butyl-ammonium fluoride, THF is tetrahydrofuran, and TLC is thin-layer chromatography.

The Bicyclic Heterocycle Derivatives of Formula (I)

The present invention provides Bicyclic Heterocycle Derivatives of Formula (I):

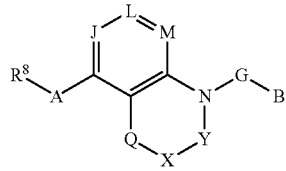

(I)

and pharmaceutically acceptable salts, solvates, esters, prodrugs and stereoisomers thereof,
wherein A, B, G, L, M, Q, X, Y and $R^8$ are defined above for the compounds of formula (I).

In one embodiment, A is alkylene.
In another embodiment, A is -(alkylene)$_t$-O-(alkylene)$_t$-.

In another embodiment, A is -(alkylene)$_t$-N($R^{12}$)-(alkylene)$_t$-.
In still another embodiment, A is -(alkylene)$_t$-S-(alkylene)$_t$-.
In one embodiment, A is —O—,
In another embodiment, A is —S—.
In another embodiment, A is —N($R^{12}$)—.
In still another embodiment, A is —NH—.
In another embodiment, A is —$CH_2$—.
In one embodiment, B is:

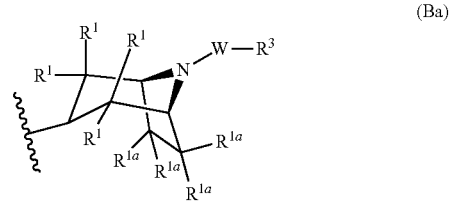

(Ba)

wherein $R^1$ and $R^3$ are defined above for the compounds of formula —C(O)O— or —S(O)$_2$— and each occurrence of $R^{1a}$ is independently selected from H, halo or alkyl.

In another embodiment, B is:

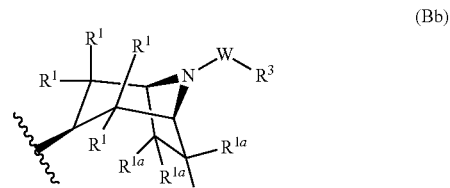

(Bb)

wherein $R^1$ and $R^3$ are defined above for the compounds of formula (I). W is —C(O)O— or —S(O)$_2$— and each occurrence of $R^{1a}$ is independently selected from H, halo or alkyl.

In another embodiment, B is:

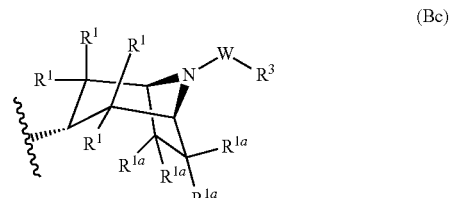

(Bc)

wherein $R^1$ and $R^3$ are defined above for the compounds of formula (I), W is —C(O)O— or —S(O)$_2$— and each occurrence of $R^{1a}$ is independently selected from H, halo or alkyl.

In still another embodiment, B is:

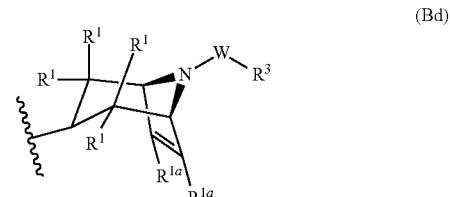

(Bd)

wherein $R^1$ and $R^3$ are defined above for the compounds of formula (I), W —C(O)O— or —S(O)$_2$— and each occurrence of $R^{1a}$ is independently selected from H, halo or alkyl.

In another embodiment, B is:

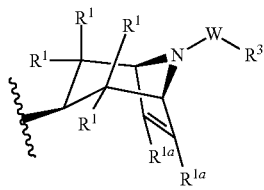

(Be)

wherein $R^1$ and $R^3$ are defined above for the compounds of formula (I), W is —C(O)O— or —S(O)$_2$— and each occurrence of $R^{1a}$ is independently selected from H, halo or alkyl.

In another embodiment, B is:

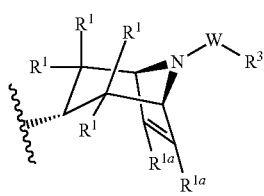

(Bf)

wherein $R^1$ and $R^3$ are defined above for the compounds of formula (I), W is —C(O)O— or —S(O)$_2$— and each occurrence of $R^{1a}$ is independently selected from H, halo or alkyl.

In yet another embodiment, B is:

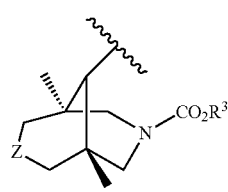

(Bg)

wherein Z and $R^3$ are defined above for the compounds of formula (I).

In another embodiment, B is:

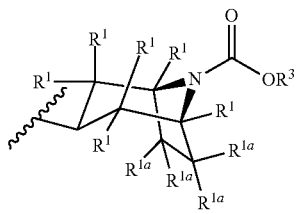

(Bh)

wherein $R^1$ and $R^3$ are defined above pounds of formula and each occurrence of $R^{1a}$ is independently H, halo or alkyl.

In a further embodiment, B is:

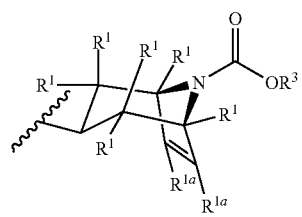

(Bj)

wherein $R^1$ and $R^3$ are defined above for the compounds of formula (I), and each occurrence of $R^{1a}$ is independently H, halo or alkyl.

In a further embodiment, B is:

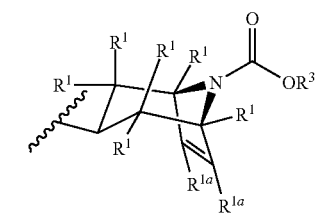

(Bk)

wherein $R^1$ and $R^3$ are defined above for the compounds of formula (I) and each occurrence of $R^{1a}$ is independently H, halo or alkyl.

In another embodiment, B is:

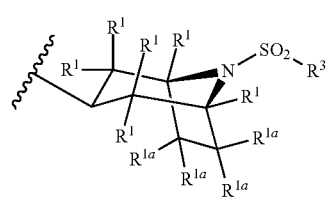

(Bm)

wherein $R^1$ and $R^5$ are defined above for the compounds of formula and each occurrence of $R^{1a}$ independently H, halo or alkyl.

In one embodiment, B is:

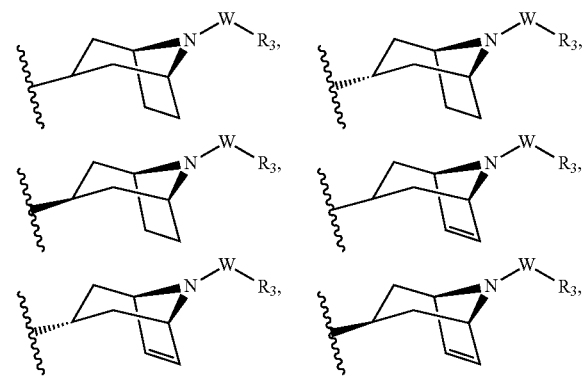

-continued
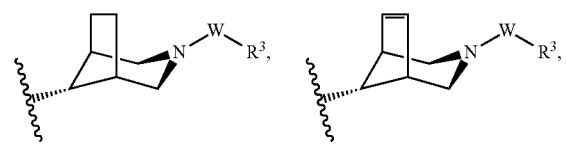
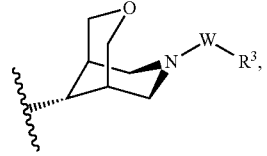
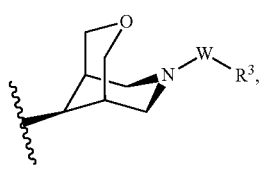
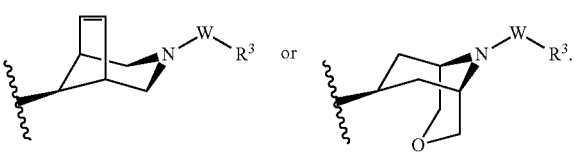
In another embodiment, B is:
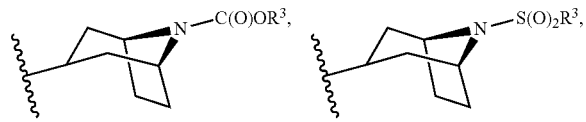
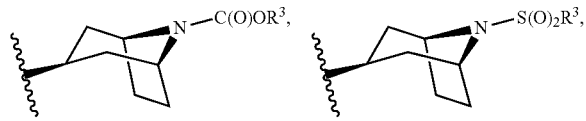
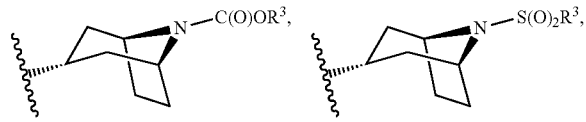
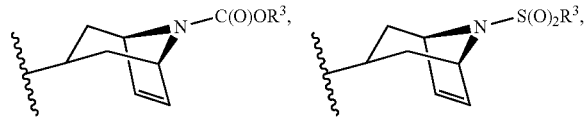
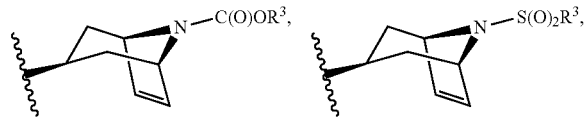
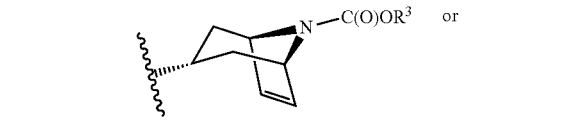
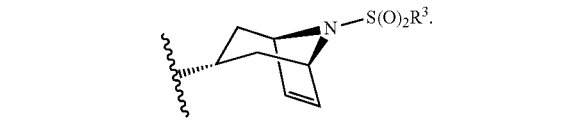
wherein R³ is alkyl, cycloalkyl or haloalkyl.
In another embodiment, B is:
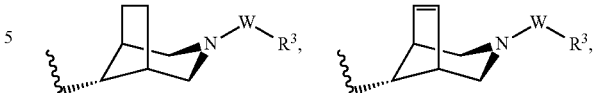
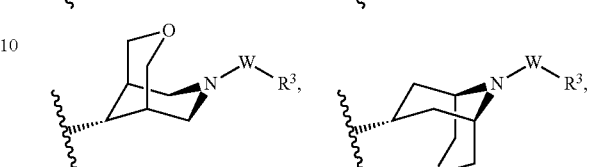
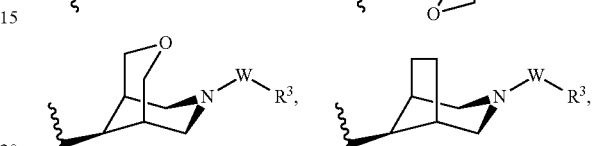
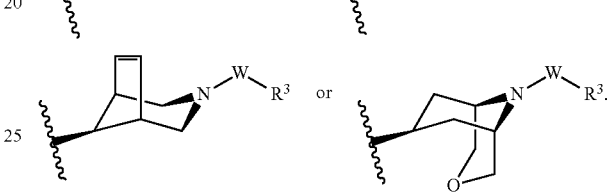
In still another embodiment, B is:
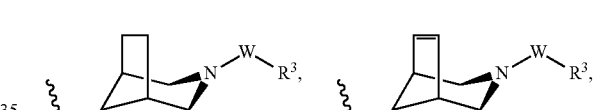
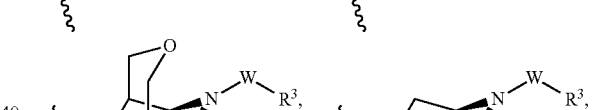
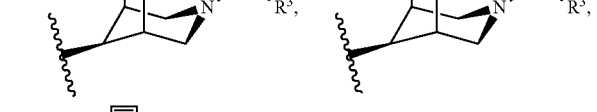
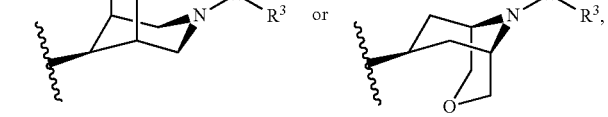
wherein W is —C(O)—, —C(O)O— or —S(O)₂— and R³ is alkyl, cycloalkyl or haloalkyl.
In another embodiment, B is:

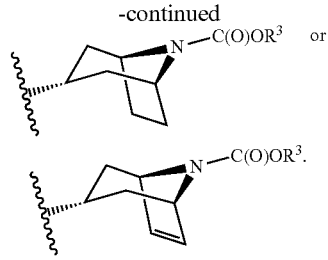
In yet another embodiment, B is:
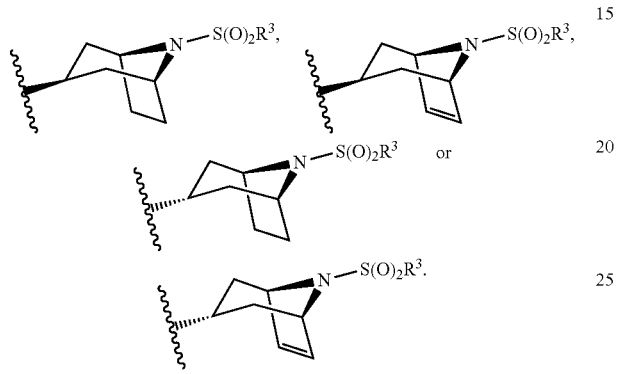
In another embodiment, B is:
wherein $R^3$ is alkyl, cycloalkyl or haloalkyl.
In a further embodiment, B is:
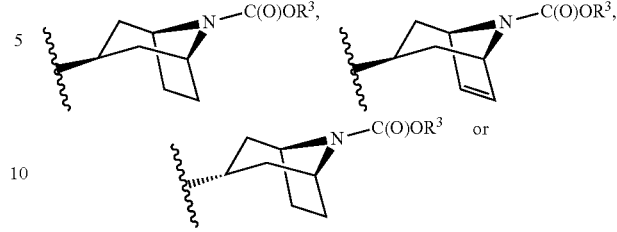
where $R^3$ is alkyl, cycloalkyl or haloalkyl.
In another embodiment, B is:
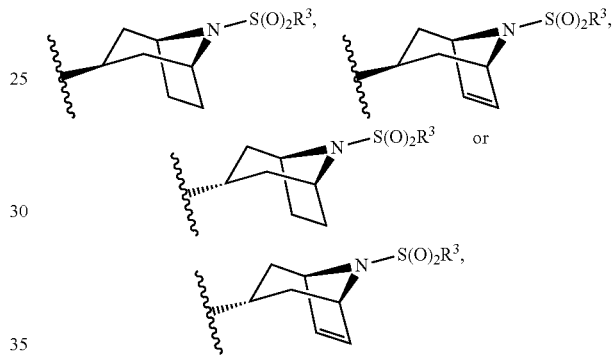
wherein $R^3$ is alkyl, cycloalkyl or haloalkyl.
In another embodiment, B is:
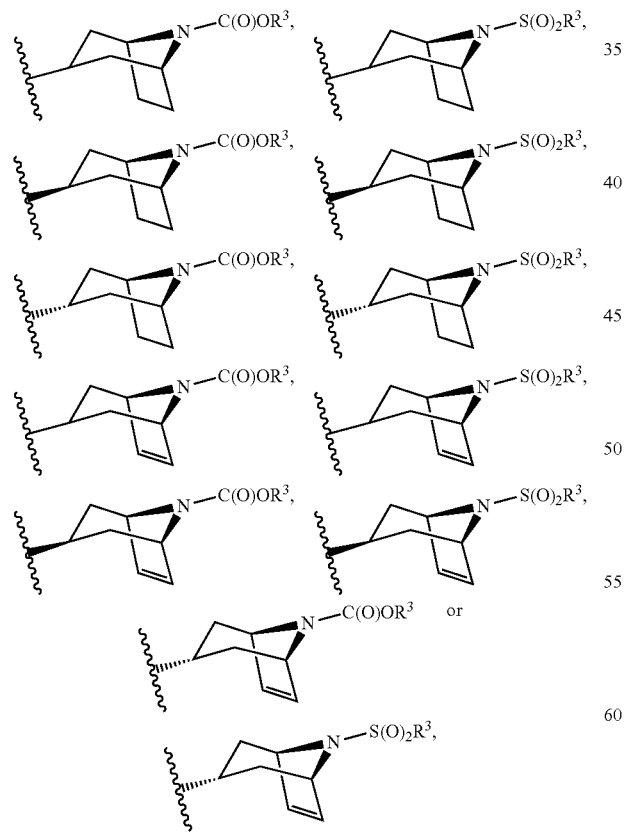
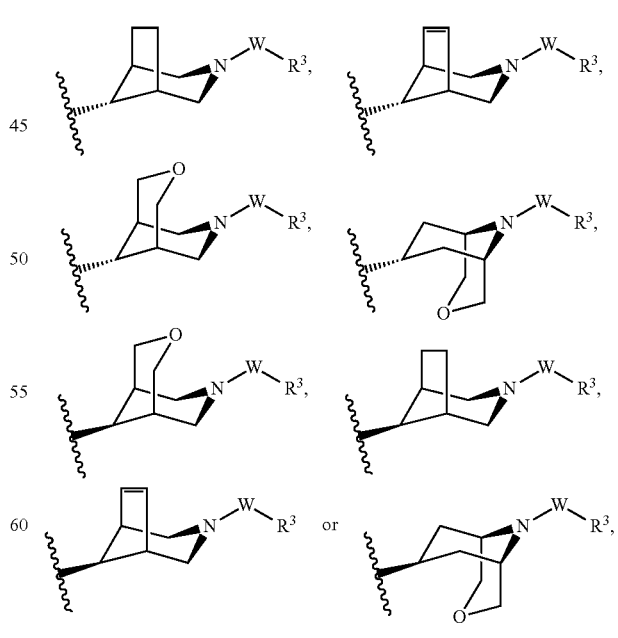
wherein W is —C(O)O— and $R^3$ is alkyl, cycloalkyl or haloalkyl.

In yet another embodiment, B is:

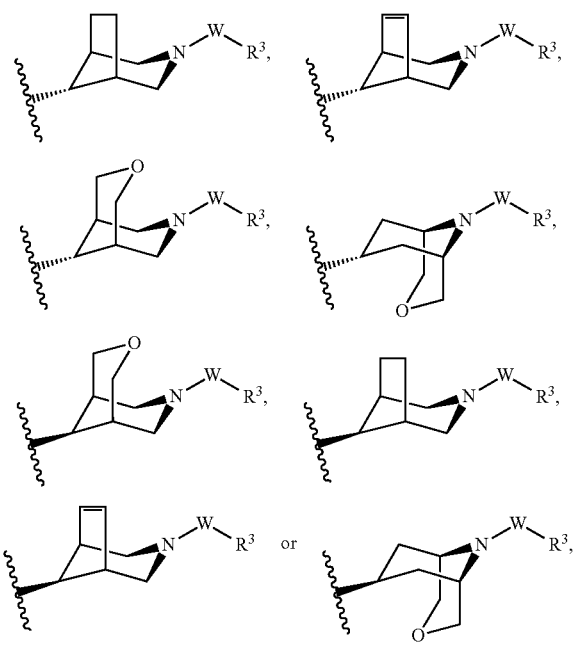

wherein W is —C(O)— and R³ is alkyl, cycloalkyl or haloalkyl.

In another embodiment, B is:

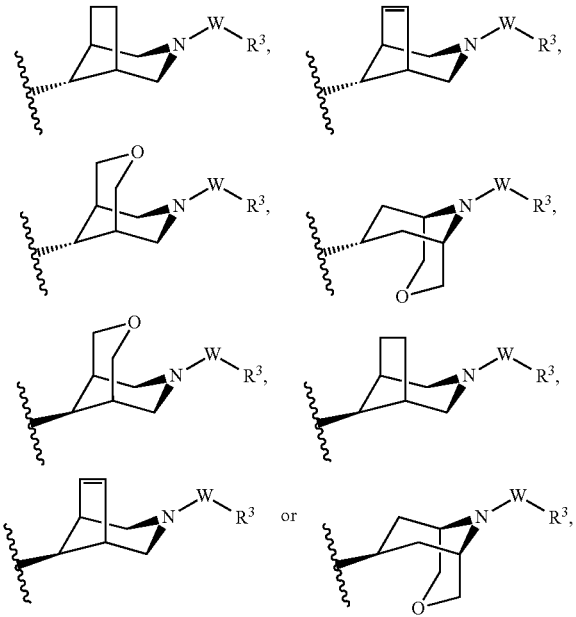

wherein W is —S(O)₂— and R³ is alkyl, cycloalkyl or haloalkyl.

In one embodiment, B is:

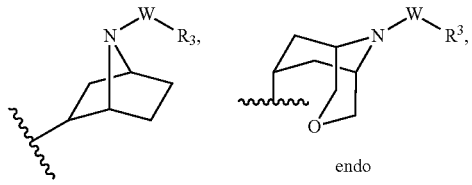

endo

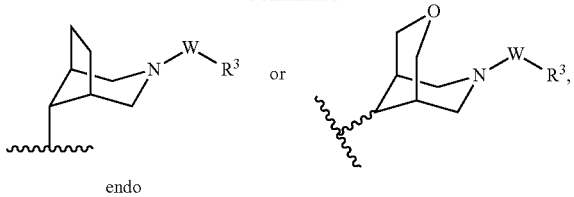

endo wherein W and R³ are defined above for the compounds of formula (I).

In one embodiment, G is a bond.
In another embodiment, G is alkylene.
In another embodiment, G is -(alkylene)$_t$-O-(alkylene)$_t$-.
In still another embodiment, G is -(alkylene)$_t$-N(R$^{12}$)-(alkylene)$_t$-.
In another embodiment, G is -(alkylene)$_t$-S-(alkylene)$_t$-.
In another embodiment, G is -alkylene-O—.
In yet another embodiment, G is -alkylene-S—.
In a further embodiment, G is -alkylene-N(R$^7$)—.
In another embodiment, G is —O—.
In another embodiment, G is —S—.
In still another embodiment, G is —NH—.
In one embodiment, J is —C(R$^{11}$)—.
In another embodiment, J is —N—.
In another embodiment, J is —CH— or —N—.
In still another embodiment, J is —CH—.
In one embodiment, L is —C(R$^{11}$)—.
In another embodiment, L is —N—.
In another embodiment, L is —CH— or —N—.
In still another embodiment, L is —CH—.
In one embodiment, M is —C(R$^{11}$)—.
In another embodiment, M is —N—.
In another embodiment, M is —CH— or —N—.
In still another embodiment, M is —CH—.
In one embodiment, W is —C(O)O—, —S(O)₂—, —C(O)— or alkylene.
In one embodiment, Q is a bond.
In another embodiment, Q is —O—.
In another embodiment, Q is —S—.
In still another embodiment, Q is —N(R$^7$)—.
In another embodiment, W is —C(O)O— or —S(O)₂—.
In another embodiment. W is a bond.
In still another embodiment, W is alkylene.
In another embodiment, W is —C(O)—.
In yet another embodiment, W is —S(O)₂—.
In another embodiment, W is —CH₂—.
In another embodiment, W is —C(O)O—.
In yet another embodiment, W is —S(O)₂N(R$^{10}$)—.
In a further embodiment, W is —C(O)N(R$^{10}$)—.
In one embodiment, —X—Y— is —C(R$^7$)₂C(R$^7$)₂— or —C(R$^7$)=C(R$^7$)—.
In another embodiment, —X—Y— is —C(R$^7$)₂C(O)—.
In another embodiment, —X—Y— is —N(R$^7$)C(O)—.
In yet another embodiment, —X—Y— is —OC(O)—.
In another embodiment, —X—Y— is —C(R$^7$)=C(R$^7$)—.
In a further embodiment, —X—Y— is —C(R$^7$)=N—.
In another embodiment, —X—Y— is —N=C(R$^7$)—.
In another embodiment, —X—Y— is —C(R$^7$)₂C(O)—.
In another embodiment, —X—Y— is —N(R$^7$)C(O)—,
In yet another embodiment, —X—Y— is —C(R$^7$)=C(R$^7$)—.
In a further embodiment, —X—Y— is —C(R$^7$)=N—.
In another embodiment, —X—Y— is —N=C(R$^7$)—.
In another embodiment, —X—Y— is —C(O)N(R$^7$)—.

In still another embodiment, —X—Y— is —C(O)C(R⁷)₂—.
In another embodiment, —X—Y— is —S(O)ₙ—C(R⁷)₂—.
In one embodiment, —X—Y— is —S(O)₂—C(R)₂—.
In another embodiment, —X—Y— is —S(O)—C(R)₂—.
In another embodiment, —X—Y— is —S—C(R⁷)₂—.
In yet another embodiment, —X—Y— is —C(R⁷)—S(O)ₙ—.
In another embodiment, —X—Y— is —C(R⁷)₂S(O)₂—.
In another embodiment, —X—Y— is —C(R⁷)₂S(O)—.
In a further embodiment, —X—Y— is —C(R⁷)₂S—.
In another embodiment, —X—Y— is —CH₂CH₂— or —CH=CH—.
In another embodiment, —X—Y— is —CH=CH—, —N=CH— or —CH=N—.
In another embodiment, —X—Y— is —CH₂CH₂—.
In still another embodiment, —X—Y— is CH=CH—.
in another embodiment, —X—Y— is —CH=N—.
In another embodiment, —X—Y— is —N=N—.
In another embodiment, —X—Y— is —N=CH—.
In yet another embodiment, —X—Y— is —C(O)NH—.
In another embodiment, —X—Y— is —NHC(O)—.
In a further embodiment, —X—Y— is —CH₂C(O)—.
In one embodiment, Z is a bond.
In another embodiment, Z is —C(R¹)₂—.
In another embodiment, Z is —O—.
In still another embodiment, Z is —N(R¹⁰)₂—.
In another embodiment, Z is —S(O)ₙ—.
In another embodiment, Z is —S(O)₂—.
In yet another embodiment, Z is —S(O)—.
In another embodiment, Z is —S—.
In another embodiment, Z is —CH₂—.
In one embodiment, each occurrence of R¹ is H, halo or —OH.
In another embodiment, each occurrence of R¹ is H.
In still another embodiment, at least one occurrence of R¹ is —OH.
In another embodiment, at least one occurrence of R¹ is halo.
In another embodiment, at least one occurrence of R¹ is F.
In another embodiment, at least one occurrence of R² is H, alkyl or —OH.
In another embodiment, at least one occurrence of R² is —OH.
In still another embodiment, at least one occurrence of R² is alkyl.
In another embodiment, at least one occurrence of R² is H.
In another embodiment, each occurrence of R² is H.
In one embodiment, R³ is alkyl or cycloalkyl.
In another embodiment, R³ is alkyl.
In another embodiment, R³ is a linear alkyl group.
In another embodiment, R³ is a branched alkyl group.
In still another embodiment, R³ is methyl.
In another embodiment, R³ is ethyl.
In another embodiment, R³ is isopropyl or t-butyl.
In another embodiment, R³ is isopropyl.
In a further embodiment, R³ is t-butyl.
In another embodiment, R³ is alkenyl.
In another embodiment, R³ is alkynyl.
In one embodiment, R³ is haloalkyl.
In another embodiment, R³ is —CF₃.
In another embodiment, R³ is —CH(CF₃)₂.
In one embodiment, R³ is cycloalkyl.
In another embodiment, R³ is cycloalkyl, which can be optionally substituted with up to 4 substituents, each independently selected from alkyl and halo.

In another embodiment, R³ is cycloalkyl, which can be optionally substituted with up to 4 substituents, each independently selected from methyl and —F.
In still another embodiment, R³ is cyclopropyl or cyclobutyl.
In another embodiment, R³ is cyclopropyl.
In another embodiment, R³ is cyclobutyl.
In still another embodiment, R³ is cyclopentyl.
In another embodiment, R³ is cyclohexyl.
In yet another embodiment, R³ is aryl.
In another embodiment, R³ is phenyl.
In still another embodiment, R³ is naphthyl.
In another embodiment, R³ is -alkylene-aryl.
In another embodiment. R³ is benzyl.
In yet another embodiment, R³ is -alkylene-O-alkylene-aryl.
in one embodiment, R³ is isopropyl, t-butyl, trifluoromethyl, cyclopropyl or cyclobutyl, wherein a cyclopropyl or cyclobutyl group can be optionally substituted with up to 4 substituents, each independently selected from alkyl and halo.
In another embodiment, R³ is:

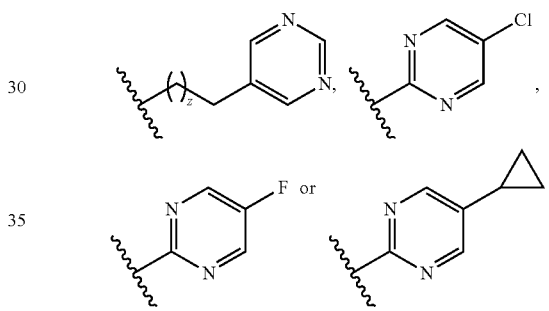

wherein z is an integer ranging from 0 to 5.
In one embodiment, R⁷ is H.
In another embodiment, R⁷ is alkyl.
In one embodiment, R⁸ is aryl or heteroaryl.
In another embodiment, R⁸ is aryl.
In another embodiment, R⁸ is heteroaryl.
In another embodiment, R⁸ is phenyl or pyridyl.
In another embodiment, R⁸ is pyridyl.
In still another embodiment, R⁸ is cycloalkyl.
In one embodiment, R⁸ is phenyl.
In another embodiment, R⁸ is phenyl, which is substituted with 1 or 2 groups, each independently selected from halo, —CN or —S(O)₂-alkyl.
In another embodiment, R⁸ is heteroaryl, which is substituted with 1 or 2 groups, each independently selected from alkyl and heteroaryl.
In yet another embodiment, R⁸ is:

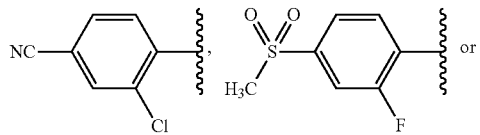

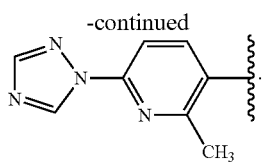

In one embodiment, A is —O— or —NH— and G is a bond.

In another embodiment, G and Q are each a bond.

In another embodiment. A is —O— or —NH—; G is a bond; and Q is a bond.

In still another embodiment, A is or —O— or —NH—; G is a bond; Q is a bond; J and M are each —N—; and L is —C($R^{11}$)—.

In another embodiment, A is —O— or —NH—; G is a bond; Q is a bond; J and M are each —N—; and L is —CH—.

In yet another embodiment, A is —O— or —NH—; G is a bond; Q is a bond; J and M are each —N—; L is —CH—; and —X—Y— is —CH$_2$CH$_2$—, —CH=CH— or —CH=NH—.

In one embodiment, Q is a bond and —X—Y— is —CH$_2$CH$_2$— or —CH=CH—.

In another embodiment, Q is —O— and —X—Y— is —C($R^7$)—N—.

In another embodiment, Q is —O— and —X—Y— is —CH—N—.

In one embodiment, J and M are each —N—.

In another embodiment, J and M are each —N— and L is —CH—.

In another embodiment, J and M are each —N—; L is —CH— and —X—Y— is —CH=N— or —CH=CH—.

In still another embodiment, J and M are each —N—; L is —CH— and —X—Y— is —CH=N—.

In another embodiment, J and M are each —N—; L is —CH— and —X—Y— is —CH=CH—.

In one embodiment, W is —C(O)O— and $R^3$ is alkyl or cycloalkyl.

In another embodiment, W is —C(O)O— and $R^3$ is cyclopropyl, cyclobutyl, isopropyl or t-butyl.

In one embodiment, W is —S(O)$_2$— and $R^3$ is alkyl or cycloalkyl.

In another embodiment, W is —S(O)$_2$— and $R^3$ is cycloalkyl.

In another embodiment, W is —S(O)$_2$— and $R^3$ is cyclopropyl or cyclobutyl.

In another embodiment, W is a bond and $R^3$ is:

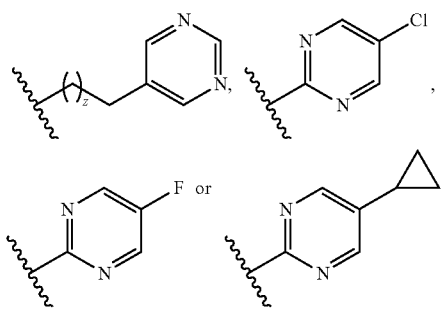

wherein z is an integer ranging from 0 to 5.

In one embodiment, p and u are each 1.

In another embodiment, p and u are each 1, and r and s are each 0.

In one embodiment, J and M are each —N—; L is —CH—; and A is —O— or —NH—.

In another embodiment, J and M are each —N—; L is —CH—; A is —O— or —NH—; and W is —C(O)O— or —S(O)$_2$—.

In another embodiment J and M are each —N—; L is —CH—; A is —O— or —NH—, W is —C(O)O— or —S(O)—; and $R^8$ is aryl or heteroaryl.

In still another embodiment, J and M are each —N—; L is —CH—; A is —O— or —NH—; W is —C(O)O— or —S(O)$_2$—; $R^8$ is aryl or heteroaryl; and $R^3$ is alkyl or cycloalkyl.

In another embodiment, J and M are each —N—; L is —CH—; A is —O— or —NH—; W is —C(O)O— or —S(O)$_2$—; $R^8$ is phenyl or pyridyl; and $R^3$ is alkyl or cycloalkyl.

In yet another embodiment, J and M are each —N—; L is —CH—; A is —O— or —NH—; W is —C(O)O— or —S(O)$_2$—; $R^8$ is phenyl or pyridyl; and $R^3$ is isopropyl, t-butyl, cyclopropyl or cyclobutyl.

In one embodiment, the present invention provides compounds of Formula (I), wherein variables A, B, G, J, L, M, Q, X, Y and $R^8$ are selected independently of each other.

In another embodiment, a compound of formula (I) is in purified form.

In one embodiment, the compounds of formula (I) have the formula (Ia):

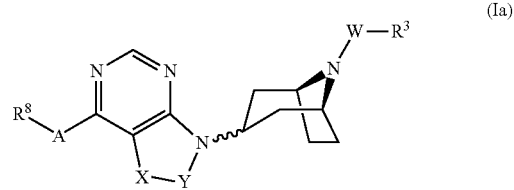

(Ia)

wherein:
A is —O— or —N($R^{12}$)—;
W is —C(O)O— or —S(O)$_2$—;
—X—Y— is —CH$_2$CH$_2$—, —CH=CH— or —CH=N—;
$R^3$ is alkyl or cycloalkyl; and
$R^5$ is aryl or heteroaryl.

In one embodiment, for the Compounds of Formula (Ia), $R^8$ is aryl.

In another embodiment, for the Compounds of Formula (Ia), $R^8$ is heteroaryl.

In another embodiment, for the Compounds of Formula (Ia), $R^8$ is pyridyl.

In still another embodiment, for the Compounds of Formula (Ia), $R^8$ is cycloalkyl.

In one embodiment, for the Compounds of Formula (Ia), $R^8$ is phenyl.

In one embodiment, for the Compounds of Formula (Ia), $R^8$ is substituted with $R^9$, wherein $R^9$ is selected from alkyl, halo, —CN, cycloalkyl, alkynyl, heteroaryl, —S-alkyl, or —S(O)$_2$-cycloalkyl.

In another embodiment, for the Compounds of Formula (Ia), $R^8$ substituted with $R^9$, wherein $R^9$ is selected from methyl, F, Cl, —CN, cyclopropyl, cyclobutyl, —C≡CH, —C≡C—CH$_3$, imidazolyl, triazolyl, —S(O)$_2$CH$_3$, or —S(O)$_2$-cyclopropyl, In another embodiment, for the Compounds of Formula (Ia), $R^8$ is phenyl, which is substituted with 1 or 2 groups, each independently selected from halo, —CN or —S(O)$_2$-alkyl.

In still another embodiment, for the Compounds of Formula (Ia), $R^8$ is heteroaryl, which is substituted with 1 or 2 groups, each independently selected from alkyl and heteroaryl.

In yet another embodiment, for the Compounds of Formula (Ia), $R^8$ is:

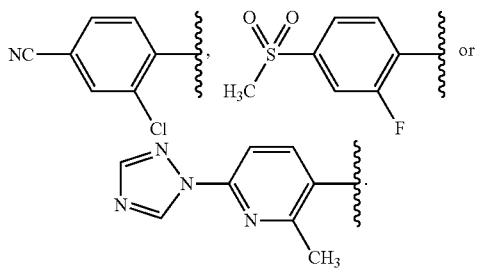

In one embodiment, for the Compounds of Formula (Ia), A is —O—.

In another embodiment, for the Compounds of Formula (Ia), A is —NH—.

In one embodiment, for the Compounds of Formula (Ia), W is —C(O)O—.

In another embodiment, for the Compounds of Formula (Ia), W is —S(O)$_2$—.

In one embodiment, for the Compounds of Formula (Ia), —X—Y— is —CH═CH— or —CH═N—.

In another embodiment, for the Compounds of Formula (Ia), —X—Y— is —CH═CH—.

In one embodiment, for the Compounds of Formula (Ia), $R^3$ is alkyl.

In another embodiment, for the Compounds of Formula (Ia), $R^3$ is a linear alkyl group.

In another embodiment, for the Compounds of Formula (Ia), $R^3$ is a branched alkyl In another embodiment, for the Compounds of Formula (Ia), $R^3$ is isopropyl.

In a further embodiment, for the Compounds of Formula (Ia), $R^3$ is t-butyl.

In one embodiment, for the Compounds of Formula (Ia), $R^3$ is cycloalkyl.

In another embodiment, for the Compounds of Formula (Ia), $R^3$ is cycloalkyl, which can be optionally substituted with up to 4 substituents, each independently selected from alkyl and halo.

In another embodiment, for the Compounds of Formula (Ia), $R^3$ is cycloalkyl, which can be optionally substituted with up to 4 substituents, each independently selected from methyl and —F.

In a further embodiment, for the Compounds of Formula (Ia), $R^3$ is cyclopropyl or cyclobutyl, which can be optionally substituted with a methyl group.

In still another embodiment, for the Compounds of Formula (Ia), $R^3$ is cyclopropyl.

In another embodiment, for the Compounds of Formula (Ia), $R^3$ is cyclobutyl.

In still another embodiment, for the Compounds of Formula (Ia), $R^3$ is cyclopentyl.

In another embodiment, for the Compounds of Formula (Ia), $R^3$ is cyclohexyl.

In one embodiment, for the Compounds of Formula (Ia), $R^8$ is aryl.

In another embodiment, for the Compounds of Formula (Ia), $R^8$ is heteroaryl.

In another embodiment, for the Compounds of Formula (Ia), $R^8$ is pyridyl.

In one embodiment, for the Compounds of Formula (Ia), $R^8$ is phenyl.

In another embodiment, for the Compounds of Formula (Ia), $R^8$ is phenyl, which is substituted with 1 or 2 groups, each independently selected from halo, —CN or —S(O)$_2$-alkyl.

In another embodiment, for the Compounds of Formula (Ia), $R^8$ is heteroaryl, which is substituted with 1 or 2 groups, each independently selected from alkyl and heteroaryl.

In one embodiment, for the Compounds of Formula (Ia), W is —S(O)$_2$— and is cycloalkyl, which can be optionally substituted with an alkyl group.

In one embodiment, for the Compounds of Formula (Ia), W is —C(O)O— and $R^3$ is alkyl.

In another embodiment, for the Compounds of Formula (Ia), W is —C(O)O— and $R^3$ is isopropyl or t-butyl.

In another embodiment, for the Compounds of Formula (Ia), W is —C(O)O— and $R^3$ is cycloalkyl, which can be optionally substituted with an alkyl group.

In one embodiment, the present invention provides compounds of Formula (Ia), wherein variables A, W, X, Y, $R^3$ and $R^8$ are selected independently of each other.

In another embodiment, a compound of formula (Ia) is in purified form.

The Bicyclic Heterocycle Derivatives of Formula (II)

The present invention further provides Bicyclic Heterocycle Derivatives of Formula (II):

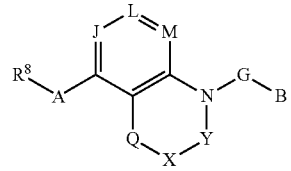

and pharmaceutically acceptable salts, solvates, esters and prodrugs thereof, wherein A, B, G, J, L, M, Q, X, Y and $R^8$ are defined above for the compounds of formula (II).

In one embodiment, A is alkylene.

In another embodiment, A is -(alkylene)$_t$-O-(alkylene)$_t$-.

In another embodiment, A is -(alkylene)$_t$-N(R$^{12}$)-(alkylene)$_t$-.

In still another embodiment, A is -(alkylene)$_t$-S-(alkylene)$_t$-.

In one embodiment, A is —O—.
In another embodiment, A is —S—.
In another embodiment, A is —N(R$^{12}$)—.
In still another embodiment, A is —NH—.
In another embodiment, A is —CH$_2$—.
In one embodiment, B is:

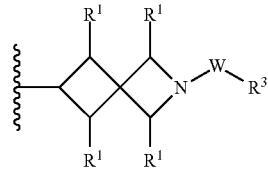

wherein W, $R^1$ and $R^3$ are defined above for the compounds of formula (II).

In another embodiment, B is:

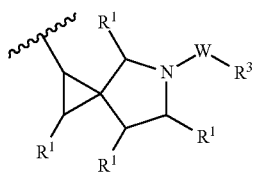

wherein W, $R^1$ and $R^3$ are defined above for the compounds of formula (II).

In another embodiment, B is:

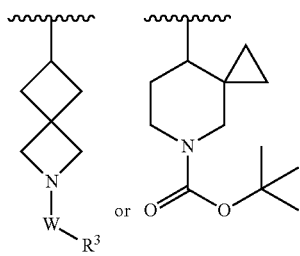

wherein $R^3$ is defined above for the compounds of formula (II).

In one embodiment, G is a bond.
In another embodiment, G is alkylene.
In another embodiment, G is -(alkylene)$_t$-O-(alkylene)$_t$-.
In still another embodiment, G is -(alkylene)$_t$-N($R^{12}$)-(alkylene)$_t$-.
In another embodiment, G is -(alkylene)$_t$-S-(alkylene)$_t$-.
In another embodiment, G is -alkylene-O—.
In yet another embodiment, G is -alkylene-S—.
In a further embodiment, G is -alkylene-N($R^7$)—.
In another embodiment, G is —O—.
In another embodiment, G is —S—.
In still another embodiment, G is —NH—.
In one embodiment, J is —C($R^{11}$)—.
In another embodiment, J is —N—.
In another embodiment, J is —CH— or —N—.
In still another embodiment, J is —CH—.
In one embodiment, L is —C($R^{11}$)—.
In another embodiment, L is —N—.
In another embodiment, L is —CH— or —N—.
In still another embodiment, L is —CH—.
In one embodiment, M is —C($R^{11}$)—.
In another embodiment, M is —N—.
In another embodiment, M is —CH— or —N—.
In still another embodiment, M is —CH—.
In one embodiment, Q is a bond.
In another embodiment, Q is —O—.
In another embodiment, Q is —S—.
In still another embodiment, Q is —N($R^7$)—.
In one embodiment, W is —C(O)O—, —S(O)$_2$—, —C(O)— or alkylene.
In another embodiment, W is —C(O)O— or —S(O)$_2$—.
In another embodiment, W is a bond.
In still another embodiment, W is alkylene.
In another embodiment, W is —C(O)—.
In yet another embodiment, W is —S(O)$_2$—.
In another embodiment, W is —CH$_2$—.
In another embodiment, W is —C(O)O—.
In yet another embodiment, W is —S(O)$_2$N($R^{10}$)—.

In a further embodiment, W is —C(O)N($R^{10}$)—.
In one embodiment, —X—Y— is —C($R^7$)$_2$C($R^7$)$_2$— or —C($R^7$)=C($R^7$)—.
In another embodiment, —X—Y— is —C($R^7$)$_2$C(O)—.
In another embodiment, —X—Y— is —N($R^7$)C(O)—.
In yet another embodiment, —X—Y— is —OC(O)—.
In another embodiment, —X—Y— is —C($R^7$)=C($R^7$)—.
In a further embodiment, —X—Y— is —C($R^7$)=N—.
In another embodiment, —X—Y— is —N=C($R^7$)—.
In another embodiment, —X—Y— is —C($R^7$)$_2$C(O)—,
In another embodiment, —X—Y— is —N($R^7$)C(O)—.
In yet another embodiment, —X—Y— is —C($R^7$)=C($R^7$)—.
In a further embodiment, —X—Y— is —C($R^7$)=N—.
In another embodiment, —X—Y— is —N=C($R^7$)—.
In another embodiment, —X—Y— is —C(O)N($R^7$)—.
In still another embodiment, —X—Y— is —C(O)C($R^7$)$_2$—.
In another embodiment, —X—Y— is —S(O)$_n$—C($R^7$)$_2$—.
In one embodiment, —X—Y— is —S(O)$_2$—C($R^7$)$_2$—.
In another embodiment, —X—Y— is —S(O)—C($R^7$)—.
In another embodiment, —X—Y— is —S—C($R^7$)$_2$—
In yet another embodiment, —X—Y— is —C($R^7$)$_2$S(O)$_2$—.
In another embodiment, —X—Y— is —C($R^7$)$_2$S(O)$_2$—.
In another embodiment, —X—Y— is —C($R^7$)$_2$S(O)—.
In a further embodiment, —X—Y— is —C($R^7$)$_2$S—.
In another embodiment, —X—Y— is —CH$_2$CH$_2$— or —CH=CH—.
In another embodiment, —X—Y— is —CH=CH—, —N=CH— or —CH=N—.
In another embodiment, —X—Y— is —CH$_2$CH$_2$—.
In still another embodiment, —X—Y— is —CH=CH—.
In another embodiment, —X—Y— is —CH=N—.
In another embodiment, —X—Y— is —N=N—.
In another, embodiment, —X—Y— is —N=CH—.
In yet another embodiment, —X—Y— is —C(O)NH—.
In another embodiment, —X—Y— is —NHC(O)—.
In a further embodiment, —X—Y— is —CH$_2$C(O)—.
In one embodiment, each occurrence of $R^1$ is H, halo or —OH.
In another embodiment, each occurrence of $R^1$ is H.
In still another embodiment, at least one occurrence of $R^1$ is —OH.
In another embodiment, at least one occurrence of $R^1$ is halo.
In another embodiment, at least one occurrence of $R^1$ is F.
In another embodiment, at least one occurrence of $R^2$ is H, alkyl or —OH.
In another embodiment, at least one occurrence of $R^2$ is —OH.
In still another embodiment, at least one occurrence of $R^2$ is alkyl.
In another embodiment, at least one occurrence of $R^2$ is H.
In another embodiment, each occurrence of $R^2$ is H.
In one embodiment, $R^3$ is alkyl.
In another embodiment, $R^3$ is a linear alkyl group.
In another embodiment, $R^3$ is a branched alkyl group.
In still another embodiment, $R^3$ is methyl.
In another embodiment, $R^3$ is ethyl.
In another embodiment, $R^3$ is isopropyl.
In a further embodiment, $R^3$ is t-butyl.
In another embodiment, $R^3$ is alkenyl.
In another embodiment, $R^3$ is alkynyl.
In one embodiment, $R^3$ is haloalkyl.
In another embodiment, $R^3$ is —CF$_3$.

In another embodiment, $R^3$ is —CH(CF$_3$)$_2$.
In one embodiment, $R^3$ is cycloalkyl.
In another embodiment, $R^3$ is cycloalkyl, which can be optionally substituted with up to 4 substituents, each independently selected from alkyl and halo.
In another embodiment, $R^3$ is cycloalkyl, which can be optionally substituted with up to 4 substituents, each independently selected from methyl and —F.
In still another embodiment, $R^3$ is cyclopropyl
In another embodiment, $R^3$ is cyclobutyl.
In still another embodiment, $R^3$ is cyclopentyl.
In another embodiment, $R^3$ is cyclohexyl.
In yet another embodiment, $R^3$ is aryl.
In another embodiment, $R^3$ is phenyl.
In still another embodiment, $R^3$ is naphthyl.
In another embodiment, $R^3$ is -alkylene-aryl.
In another embodiment, $R^3$ is benzyl.
In yet another embodiment, $R^3$ is -alkylene-O-alkylene-aryl.
In one embodiment, $R^3$ is isopropyl, t-butyl, trifluoromethyl, cyclopropyl or cyclobutyl, wherein a cyclopropyl or cyclobutyl group can be optionally substituted with up to 4 substituents, each independently selected from alkyl and halo.
In another embodiment, $R^3$ is:

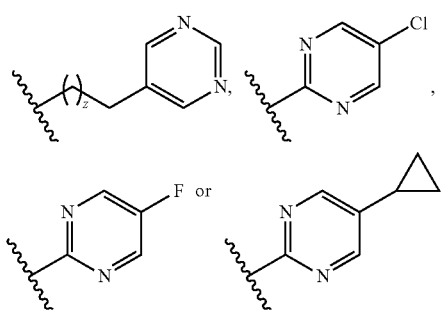

wherein z is an integer ranging from 0 to 5.
In one embodiment, $R^7$ is H.
In another embodiment, $R^7$ is alkyl.
In another embodiment, $R^8$ is aryl or heteroaryl.
In another embodiment, $R^8$ is aryl.
In another embodiment, $R^8$ is heteroaryl.
In another embodiment, $R^8$ is pyridyl.
In still another embodiment, $R^8$ is cycloalkyl.
In one embodiment, $R^8$ is phenyl.
In one embodiment, $R^8$ is substituted with $R^9$, wherein $R^9$ is selected from alkyl, halo, —CN, cycloalkyl, alkynyl, heteroaryl, —S-alkyl, or —S(O)$_2$-cycloalkyl.
In another embodiment, $R^8$ is substituted with $R^9$, wherein $R^9$ is selected from methyl, F, Cl, —CN, cyclopropyl, cyclobutyl, —C≡CH, —C≡C—CH$_3$, imidazolyl, triazolyl, —S(O)$_2$CH$_3$, or —S(O)$_2$-cyclopropyl.
In another embodiment, $R^8$ is phenyl, which is substituted with 1 or 2 groups, each independently selected from halo, —CN or —S(O)$_2$-alkyl.
In still another embodiment, $R^8$ is heteroaryl, which is substituted with 1 or 2 groups, each independently selected from alkyl and heteroaryl.

In yet another embodiment, $R^8$ is:

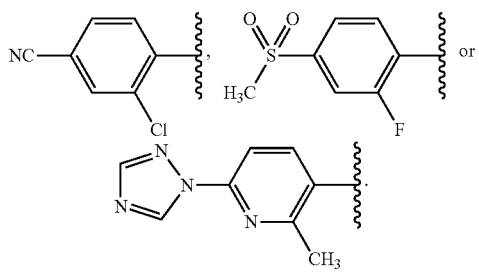

In one embodiment, p and q are each 1.
In another embodiment, r and s are each 0.
In another embodiment, p, q, r and s are each 1.
In one embodiment, the sum of p and q is 1.
In another embodiment, the sum of p and q is 2.
In another embodiment, the sum of p and q is 3.
In still another embodiment, the sum of p and q is 4.
In another embodiment, the sum of p and q is 5.
In yet another embodiment, the sum of p and q is 6.
In one embodiment, the sum of r and s is 1.
In another embodiment, the sum of r and s is 2.
In another embodiment, the sum of r and s is 3.
In still another embodiment, the sum of r and s is 4.
In another embodiment, the sum of r and s is 5.
In yet another embodiment, the sum of r and s is 6.
In another embodiment, p and r are each 1, q is 0 and s is 2.
In one embodiment, A is —O— or —NH— and G is a bond.
In another embodiment, G and Q are each a bond.
In another embodiment, A is —O— or —NH—; G is a bond; and Q is a bond.
In still another embodiment, A is —O— or —NH—; G is a bond; Q is a bond; J and M are each —N—; and L is —C($R^{11}$)—.
In another embodiment, A is —O— or —NH—; G is a bond; Q is a bond; J and M are each —N—; and L is —CH—.
In yet another embodiment, A is —O— or —NH—; G is a bond; Q is a bond; J and are each —N—; L is —CH—; and —X—Y— is —CH$_2$CH$_2$—, —CH═CH— or —CH═N—.
In one embodiment, W is —C(O)O— and $R^3$ is alkyl, cycloalkyl or haloalkyl.
In another embodiment, W is —C(O)O— and $R^3$ is cyclopropyl, cyclobutyl, isopropyl, t-butyl, —CF$_3$ or —CH(CF$_3$)$_2$
In one embodiment, W is —S(O)$_2$— and $R^3$ is alkyl or cycloalkyl.
In another embodiment, W is —S(O)$_2$— and $R^3$ is cycloalkyl.
In another embodiment, W is —S(O)$_2$— and $R^3$ is cyclopropyl or cyclobutyl.
In another embodiment, W is —NH— and $R^3$ is aryl or alkyl.
In one embodiment, J and M are each —N—.
In another embodiment, J and M are each —N—, Q is a bond, and L is —CH—.
In another embodiment, J and M are each —N—; L is —CH—; Q is a bond; and —X—Y— is —CH—CH$_2$— or —CH═CH—.
In still another embodiment, J and M are each —N—; L is —CH—; Q is a bond; and —X—Y— is —CH$_2$CH$_2$—.
In another embodiment, J and M are each —N—; L is —CH—; Q is a bond; and —X—Y— is —CH═CH—.

In one embodiment, W is —C(O)O— or —S(O)₂—; and A is —O—.

In another embodiment, W is —C(O)O— or —S(O)₂—; A is —O—; and R³ is alkyl or cycloalkyl.

In yet another embodiment, W is —C(O)O— or —S(O)₂—; A is —O—; and R⁸ is aryl or heteroaryl.

In a further embodiment, W is —C(O)O— or —S(O)₂—; A is —O—; R³ is alkyl or cycloalkyl; and R⁸ is aryl or heteroaryl.

In another embodiment, W is —C(O)O—; and A is —O—.

In another embodiment, W is —C(O)O—; A is —O—; and R³ is alkyl or cycloalkyl.

In yet another embodiment, W is —C(O)O—; A is —O—; and R⁸ is aryl or heteroaryl.

In another embodiment, W is a bond and R³ is;

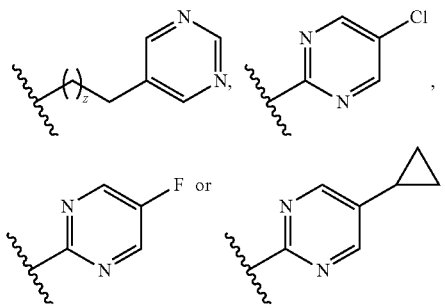

wherein z is an integer ranging from 0 to 5.

In a further embodiment, W is —C(O)O—; A is —O—; R³ is alkyl or cycloalkyl; and R⁸ is aryl or heteroaryl.

In one embodiment, W is —S(O)₂—; and A is —O—.

In another embodiment, W is —S(O)₂—; A is —O—; and R³ is alkyl or cycloalkyl.

In yet another embodiment, W is —S(O)₂—; A is —O—; and R⁸ is aryl or heteroaryl.

In a further embodiment, W is —S(O)₂—; A is —O—; R³ is alkyl or cycloalkyl; and R⁸ is aryl or heteroaryl.

In one embodiment, J and M are each —N—; L is —CH—; Q is a bond; —X—Y— is —CH₂CH₂— or —CH═CH—; and A is —O—.

In another embodiment, and W is —C(O)O— or —S(O)₂—.

In another embodiment, J and M are each —N—; L is —CH—; Q is a bond; —X—Y— is —CH₂CH₂— or —CH═CH—; W is —C(O)O— or —S(O)₂—; and A is —O—.

In still another embodiment, J and M are each —N—; L is —CH—; Q is a bond; —X—Y— is —CH₂CH₂— or —CH═CH—; W is —C(O)O— or —S(O)₂—; A is —O—; and R³ is alkyl or cycloalkyl.

In another embodiment, J and M are each —N—; L is —CH—; Q is a bond; —X—Y— is —CH₂CH₂— or —CH═CH—; W is —C(O)O— or —S(O)₂—; A is —O—; and R⁸ is aryl or heteroaryl.

In a further embodiment, J and M are each —N—; L is —CH—; Q is a bond; —X—Y— is —CH₂CH₂— or —CH═CH—; W is —C(O)O— or —S(O)₂—; A is —O—; R³ is alkyl or cycloalkyl; and R⁵ is aryl or heteroaryl.

In one embodiment, e present invention provides compounds of Formula (II), wherein variables A, B, G, Q, X, Y and R⁸ are selected independently of each other.

In another embodiment, a compound of formula (II) is in purified form.

The Bicyclic Heterocycle Derivatives of Formula (III)

The present invention further provides Bicyclic Heterocycle Derivatives of Formula (III):

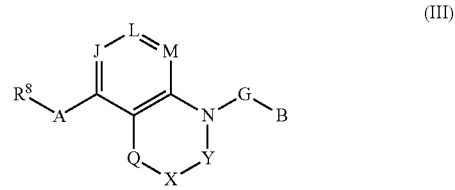

and pharmaceutically acceptable salts, solvates, esters and prodrugs thereof, wherein A, B, G, J, L, M, Q, X, Y and R⁸ are defined above for the compounds of formula (III).

In one embodiment, A is alkylene.

In another embodiment, A is -(alkylene)ₜ-O-(alkylene)ₜ-.

In another embodiment, A is -(alkylene)ₜ-N(R¹²)-(alkylene)ₜ-.

In still another embodiment, A is -(alkylene)ₜ-S-(alkylene)ₜ-.

In one embodiment, A is —O—.

In another embodiment, A is —S—.

In another embodiment, A is —N(R¹²)—.

In still another embodiment, A is —NH—.

In another embodiment, A is —CH₂—.

In one embodiment, B is:

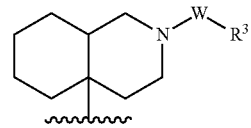

wherein W and R³ are defined above for the compounds of formula (III).

In another embodiment, B is:

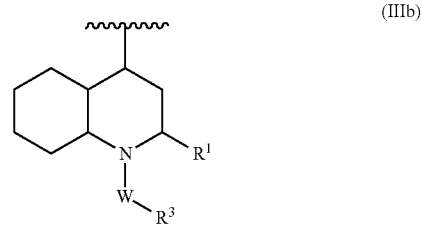

wherein W, R¹ and R³ are defined above for the compounds of formula (III).

In another embodiment, B is:

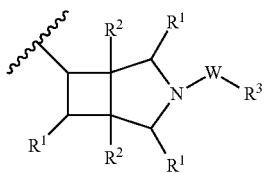

wherein W, R$^1$, R$^2$ and R$^3$ are defined above for the compounds of formula (III).

In still another embodiment, B is:

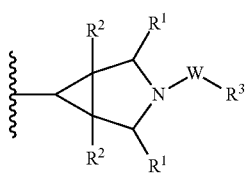

wherein W, R$^1$, R$^2$ and R$^3$ are defined above for the compounds of formula (III).

In another embodiment, B is:

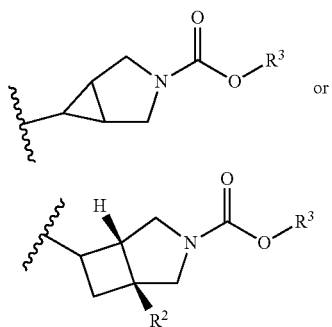

wherein R$^2$ and R$^3$ are defined above for the compounds of formula (III).

In one embodiment, G is a bond.
In another embodiment, G is alkylene.
In another embodiment, G is -(alkylene)$_t$-O-(alkylene)$_t$-.
In still another embodiment, G is -(alkylene)$_t$-N(R$^{12}$)-(alkylene)$_t$-.
In another embodiment, G is -(alkylene)$_t$-S-(alkylene)$_t$-.
In another embodiment, G is -alkylene-O—.
In yet another embodiment, G is -alkylene-S—.
In a further embodiment, G is -alkylene-N(R$^7$)—.
In another embodiment, G is —O—.
In another embodiment, G is —S—.
In still another embodiment, G is —NH—.
In one embodiment, J is —C(R$^{11}$)—.
In another embodiment, J is —N—.
In another embodiment, J is —CH— or —N—.
In still another embodiment, J is —CH—.
In one embodiment, L is —C(R$^{11}$)—.
In another embodiment, L is —N—.
In another embodiment, L is —CH— or —N—.
In still another embodiment, L is —CH—.
In one embodiment, M is —C(R$^{11}$)—.
In another embodiment, M is —N—.
In another embodiment, M is —CH— or —N—.

In still another embodiment, M is —CH—.
In one embodiment, Q is a bond.
In another embodiment, Q is —O—.
In another embodiment, Q is —S—.
In still another embodiment, Q is —N(R$^7$)—.
In one embodiment, W is —C(O)O—, —S(O)$_2$—, —C(O)— or alkylene.
In another embodiment, W is —C(O)O— or —S(O)$_2$—.
In another embodiment, W is a bond.
In still another embodiment, W is alkylene.
In another embodiment, W is —C(O)—.
In yet another embodiment, W is —S(O)$_2$—.
In another embodiment, W is —CH$_2$—.
In another embodiment, W is —C(O)O—.
In yet another embodiment, W is —S(O)$_2$N(R$^{10}$)—.
In a further embodiment, W is —C(O)N(R$^{10}$)—.
In one embodiment, —X—Y— is —C(R$^7$)$_2$C(R$^7$)$_2$— or —C(R$^7$)═C(R$^7$)—.
In another embodiment, —X—Y— is —C(R$^7$)$_2$C(O)—.
In another embodiment, —X—Y— is —N(R$^7$)C(O)—.
In yet another embodiment, —X—Y— is —OC(O)—.
In another embodiment, —X—Y— is —C(R$^7$)═C(R$^7$)—.
In a further embodiment, —X—Y— is —C(R$^7$)═N—.
In another embodiment, —X—Y— is —N═C(R$^7$)—.
In another embodiment, —X—Y— is —C(R$^7$)$_2$C(O)—.
In another embodiment, —X—Y— is —N(R$^7$)C(O)—.
In yet another embodiment, —X—Y— is —C(R$^7$)═C(R$^7$)—.
In a further embodiment, —X—Y— is —C(R$^7$)═N—.
In another embodiment, —X—Y— is —N═C(R$^7$)—.
In another embodiment, —X—Y— is —C(O)N(R$^7$)—.
In still another embodiment, —X—Y— is —C(O)C(R$^7$)$_2$—.
In another embodiment, —X—Y— is —S(O)$_n$—C(R$^7$)$_2$—.
In one embodiment, —X—Y— is —S(O)$_2$—C(R$^7$)$_2$—.
In another embodiment, —X—Y— is —S(O)—C(R$^7$)$_2$—.
In another embodiment, —X—Y— is —S—C(R$^7$)$_2$—.
In yet another embodiment, —X—Y— is —C(R$^7$)$_2$S(O)$_n$—.
In another embodiment, —X—Y— is —C(R$^7$)$_2$S(O)$_2$—.
In another embodiment, —X—Y— is —C(R$^7$)$_2$S(O)—.
In a further embodiment, —X—Y— is —C(R$^7$)$_2$S—.
In another embodiment, —X—Y— is —CH$_2$CH$_2$— or —CH═CH—.
In another embodiment, —X—Y— is —CH═CH—, —N═CH— or —CH═N—.
In another embodiment, —X—Y— is —CH$_2$CH$_2$—.
In still another embodiment, —X—Y— is —CH═CH—.
In another embodiment, —X—Y— is —CH—N—.
In another embodiment, —X—Y— is —N═N—.
In another embodiment, —X—Y— is —N═CH—.
In yet another embodiment, —X—Y— is —C(O)NH—.
In another embodiment, —X—Y— is —NHC(O)—.
In a further embodiment, —X—Y— is —CH$_2$C(O).
In one embodiment, each occurrence of R$^1$ is H, halo or —OH.
In another embodiment, each occurrence of R$^1$ is H.
In still another embodiment, at least one occurrence of R$^1$ is —OH.
In another embodiment, at least one occurrence of R$^1$ is halo.
In another embodiment, at least one occurrence of R$^1$ is F.
In another embodiment, at least one occurrence of R$^2$ is H, alkyl or —OH.
In another embodiment, at least one occurrence of R$^2$ is —OH.

In still another embodiment, at least one occurrence of $R^2$ is alkyl.

In another embodiment, at least one occurrence of $R^2$ is H.
In another embodiment, each occurrence of $R^2$ is H.
In one embodiment, $R^3$ is alkyl.
In another embodiment, $R^3$ is a linear alkyl group.
In another embodiment, $R^3$ is a branched alkyl group.
In still another embodiment, $R^3$ is methyl.
In another embodiment, $R^3$ is ethyl.
In another embodiment, $R^3$ is isopropyl.
In a further embodiment, $R^3$ is t-butyl.
In another embodiment, $R^3$ is alkenyl.
In another embodiment, $R^3$ is alkynyl.
In one embodiment, $R^3$ is haloalkyl.
In another embodiment, $R^3$ is —$CF_3$.
In another embodiment, $R^3$ is —$CH(CF_3)_2$.
In one embodiment, $R^3$ is cycloalkyl.
In another embodiment, $R^3$ is cycloalkyl, which can be optionally substituted with up to 4 substituents, each independently selected from alkyl and halo.
In another embodiment, $R^3$ is cycloalkyl, which can be optionally substituted with up to 4 substituents, each independently selected from methyl and —F.
In still another embodiment, $R^3$ is cyclopropyl.
In another embodiment, $R^3$ is cyclobutyl.
In still another embodiment, $R^3$ is cyclopentyl.
In another embodiment, $R^3$ is cyclohexyl.
In yet another embodiment, $R^3$ is aryl.
In another embodiment, $R^3$ is phenyl.
In still another embodiment, $R^3$ is naphthyl.
In another embodiment, $R^3$ is -alkylene-aryl.
In another embodiment, $R^3$ is benzyl.
In yet another embodiment, $R^3$ is -alkylene-O-alkylene-aryl.

In one embodiment, $R^3$ is isopropyl, t-butyl, trifluoromethyl, cyclopropyl or cyclobutyl, wherein a cyclopropyl or cyclobutyl group can be optionally substituted with up to 4 substituents, each independently selected from alkyl and halo.

In another embodiment, $R^3$ is:

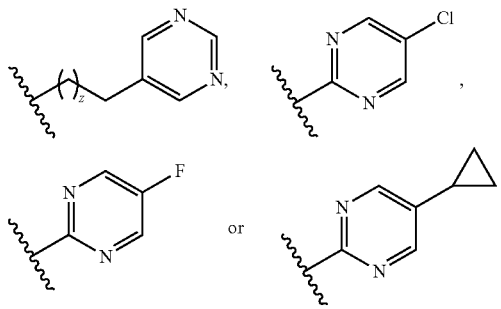

wherein z is an integer ranging from 0 to 5.
In one embodiment, $R^7$ is H.
In another embodiment, $R^7$ is alkyl.
In one embodiment, $R^8$ is aryl or heteroaryl.
In another embodiment, $R^8$ is aryl.
In another embodiment, $R^8$ is heteroaryl.
In another embodiment, $R^8$ is pyridyl.
In still another embodiment, $R^8$ is cycloalkyl.
In one embodiment, $R^8$ is phenyl.
In one embodiment, $R^8$ is substituted with $R^9$, wherein $R^9$ is selected from alkyl, halo, —CN, cycloalkyl, alkynyl, heteroaryl, —S-alkyl, or —$S(O)_2$-cycloalkyl.

In another embodiment, $R^8$ is substituted with $R^9$, wherein $R^9$ is selected from methyl, F, Cl, —CN, cyclopropyl, cyclobutyl, —C≡CH, —C≡C—$CH_3$, imidazolyl, triazolyl, —$S(O)_2CH_3$, or —$S(O)_2$-cyclopropyl.

In another embodiment, $R^8$ is phenyl, which is substituted with 1 or 2 groups, each independently selected from halo, —CN or —$S(O)_2$-alkyl.

In still another embodiment, $R^8$ is heteroaryl, which is substituted with 1 or 2 groups, each independently selected from alkyl and heteroaryl.

In yet another embodiment, $R^8$ is:

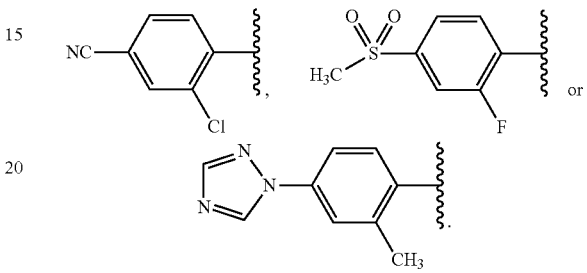

In one embodiment, p and u are each 1.
In another embodiment, p and u are each 1, and r and s are each 0.
In one embodiment, p and q are each 1.
In another embodiment, r and s are each 0.
In another embodiment, p, q, r and s are each 1.
In one embodiment, the sum of p and q is 1.
In another embodiment, the sum of p and q is 2.
In another embodiment, the sum of p and q is 3.
In still another embodiment, the sum of p and q is 4.
In another embodiment, the sum of p and q is 5.
In yet another embodiment, the sum of p and q is 6.
In one embodiment, the sum of r and s is 1.
In another embodiment, the sum of r and s is 2.
In another embodiment, the sum of r and s is 3.
In still another embodiment, the sum of r and s is 4.
In another embodiment, the sum of r and s is 5.
In yet another embodiment, the sum of r and s is 6.
In one embodiment, A is —O— or —NH— and G is a bond.
In another embodiment, G and Q are each a bond.
In another embodiment, A is —O— or —NH—; G is a bond; and Q is a bond.
In still another embodiment, A is —O— or —NH—; G is a bond; Q is a bond; J and M are each —N—; and L is —$C(R^{11})$—.
In another embodiment, A is —O— or —NH—; G is a bond; Q is a bond; J and M are each —N—; and L is —CH—.
In yet another embodiment, A is —O— or —NH—; G is a bond; Q is a bond; J and M are each —N—; L is —CH—; and —X—Y— is —$CH_2CH_2$—, —CH=CH— or —CH=N—.
In one embodiment, W is —C(O)O— and $R^3$ is alkyl, cycloalkyl or haloalkyl.
In another embodiment, W is —C(O)O— and $R^3$ is cyclopropyl, cyclobutyl, isopropyl, t-butyl, —$CF_3$ or —$CH(CF_3)_2$
In one embodiment, W is —$S(O)_2$— and $R^3$ is alkyl or cycloalkyl.
In another embodiment, W is —$S(O)_2$— and $R^3$ is cycloalkyl.
In another embodiment, W is —$S(O)_2$— and $R^3$ is cyclopropyl or cyclobutyl.

In another embodiment, W is —NH— and R³ is aryl or alkyl.

In one embodiment, J and M are each —N—.

In another embodiment, J and M are each —N—, Q is a bond, and L is —CH—.

In another embodiment, J and M are each —N—; L is —CH—; Q is a bond; and —X—Y— is —CH₂CH₂— or —CH=CH—.

In still another embodiment, J and M are each —N—; L is —CH—; Q is a bond; and —X—Y— is —CH₂CH₂—.

In another embodiment, J and M are each —N—; L is —CH—; Q is a bond; and —X—Y— is —CH=CH—.

In one embodiment, W is —C(O)O— or —S(O)₂—; and A is —O—.

In another embodiment. W is a bond and R³ is:

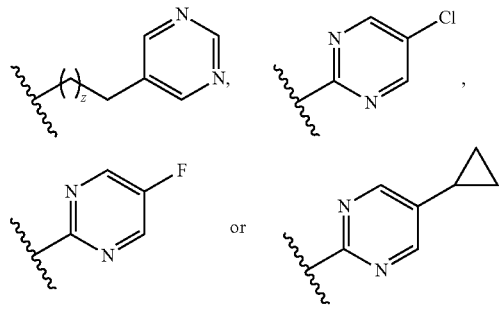

wherein z is an integer ranging from 0 to 5.

In another embodiment, W is —C(O)O— or —S(O)₂—; A is —O—; and R³ is alkyl or cycloalkyl.

In yet another embodiment, W is —C(O)O— or —S(O)₂—; A is —O—; and R³ is aryl or heteroaryl.

In a further embodiment, W is —C(O)O— or —S(O)₂—; A is —O—; R³ is alkyl or cycloalkyl; and R⁸ is aryl or heteroaryl.

In another embodiment, W is —C(O)O—; and A is —O—.

In another embodiment, W is —C(O)O—; A is —O—; and R³ is alkyl or cycloalkyl.

In yet another embodiment, W is —C(O)O—; A is —O—; and R⁸ is aryl or heteroaryl.

In a further embodiment, W is —C(O)O—; A is —O—; R³ is alkyl or cycloalkyl; and R⁸ is aryl or heteroaryl.

In one embodiment, W is —S(O)₂—; and A is —O—.

In another embodiment, W is —S(O)₂—; A is —O—; and R³ is alkyl or cycloalkyl.

In yet another embodiment, W is —S(O)₂—; A is —O—; and R⁸ is aryl or heteroaryl.

In a further embodiment, W is —S(O)₂—; A is —O—; R³ is alkyl or cycloalkyl; and R⁸ is aryl or heteroaryl.

In one embodiment, J and M are each —N—; L is —CH—; Q is a bond; —X—Y— is —CH₂CH₂— or —CH=CH—; and A is —O—.

In another embodiment, and W is —C(O)O— or —S(O)₂—.

In another embodiment, J and M are each —N—; L is —CH—; Q is a bond; —X—Y— is —CH₂CH₂—, —CH—; —C(O)O— or —S(O)₂—; and A —O—.

In still another embodiment, J and M are each —N—; L is —CH—; Q is a bond; —X—Y— is —CH₂CH₂— or —CH=CH—; W is —C(O)O— or —S(O)₂—; A is —O—; and R³ is alkyl or cycloalkyl.

In another embodiment, J and M are each —N—; L is —CH—; Q is a bond; —X—Y— is —CH₂CH₂— or —CH=CH—; W is —C(O)O— or —S(O)₂—; A is —O—; and R⁸ is aryl or heteroaryl.

In a further embodiment, J and M are each —N—; L is —CH—; Q is a bond; —X—Y— is —CH₂CH₂— or —CH=CH—; W is —C(O)O— or —S(O)₂—; A is —O—; R³ is alkyl or cycloalkyl; and R⁸ is aryl or heteroaryl.

In one embodiment, the present invention provides compounds of Formula (III), wherein variables A, B, G, J, L, M, Q, X, Y and R⁸ are selected independently of each other.

In another embodiment, a compound of formula (III) is in purified form.

Non-limiting examples of the Bicyclic Heterocycle Derivatives of the present invention include, but are not limited to, the following compounds:

| Compound No. | STRUCTURE | MW (M + H) |
|---|---|---|
| 1 | 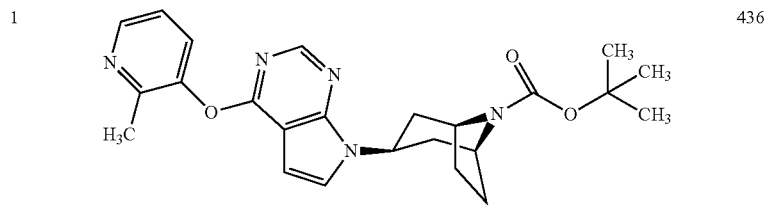 | 436 |
| 2 | 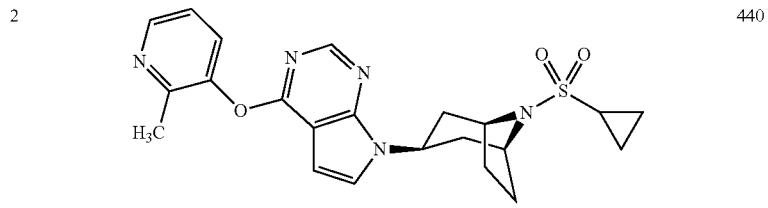 | 440 |

-continued
| Compound No. | STRUCTURE | MW (M + H) |
|---|---|---|
| 3 | 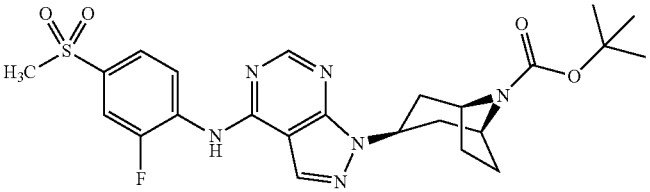 | 517 |
| 4 | 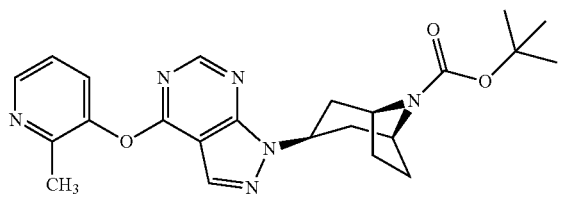 | 437 |
| 5 | 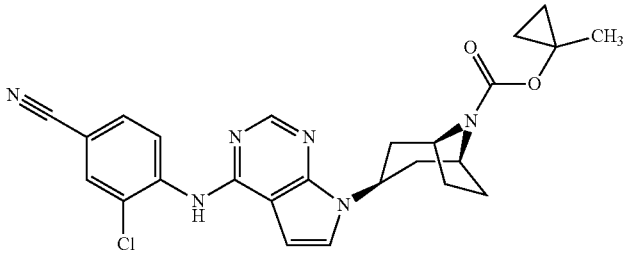 | 477 |
| 6 | 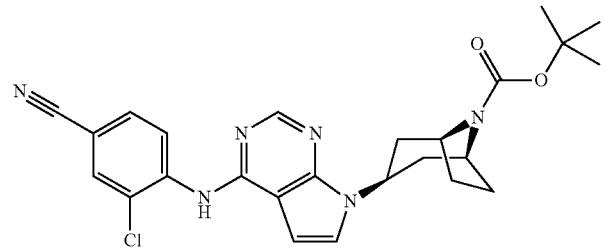 | 479 |
| 7 | 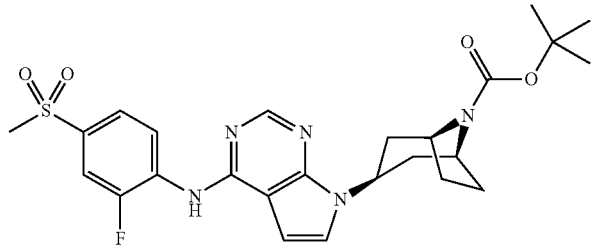 | 516 |
| 8 | 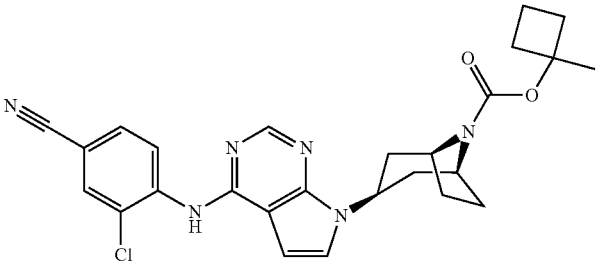 | 491 |

-continued

| Compound No. | STRUCTURE | MW (M + H) |
|---|---|---|
| 9 | 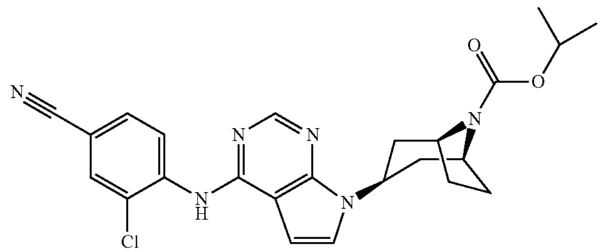 | 465 |
| 10 | 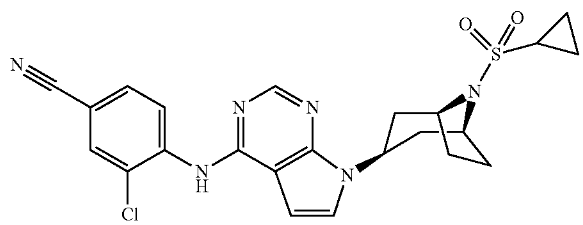 | 483 |
| 11 | 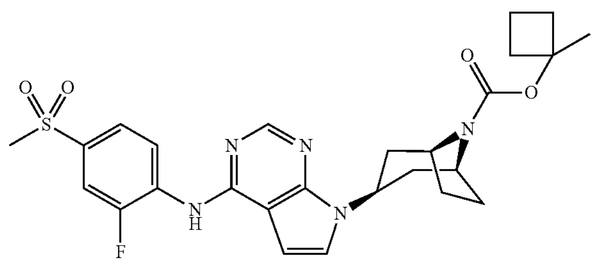 | 528 |
| 12 | 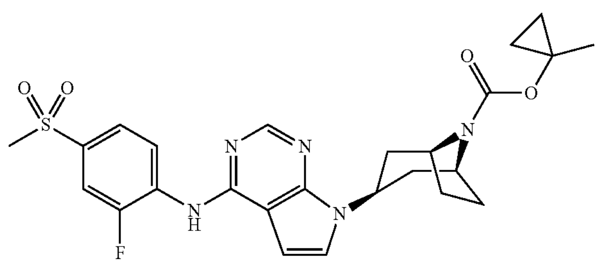 | 514 |
| 13 | 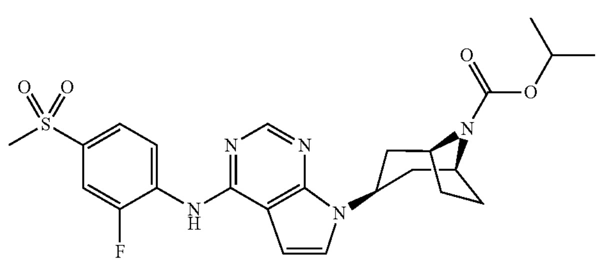 | 502 |
| 14 | 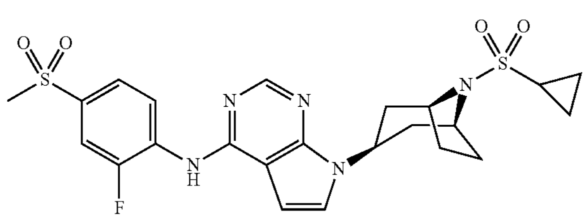 | 520 |

-continued

| Compound No. | STRUCTURE | MW (M + H) |
|---|---|---|
| 15 | 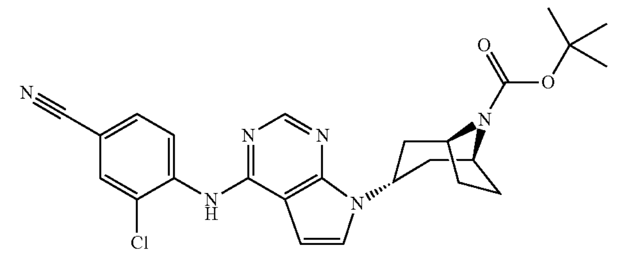 | 479 |
| 16 | 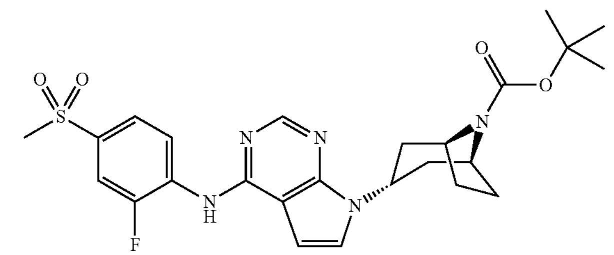 | 516 |
| 17 | 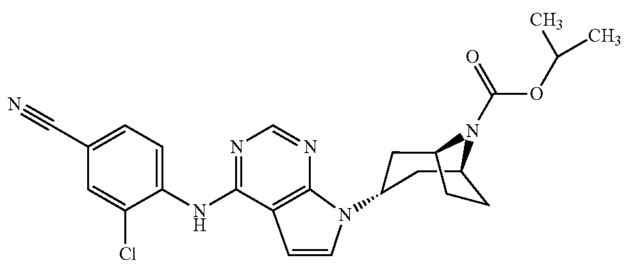 | 465 |
| 18 | 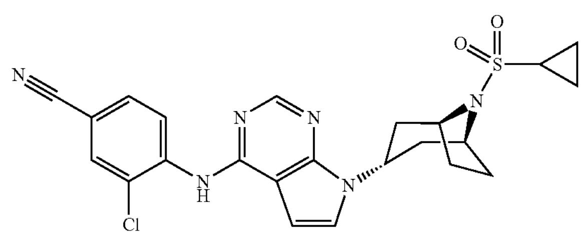 | 483 |
| 19 | 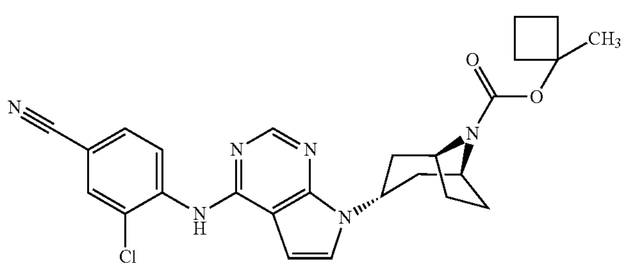 | 491 |
| 20 | 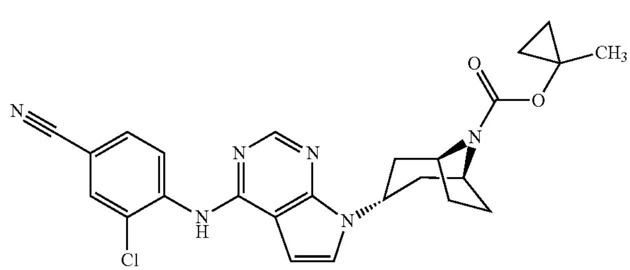 | 477 |

-continued

| Compound No. | STRUCTURE | MW (M + H) |
|---|---|---|
| 21 | 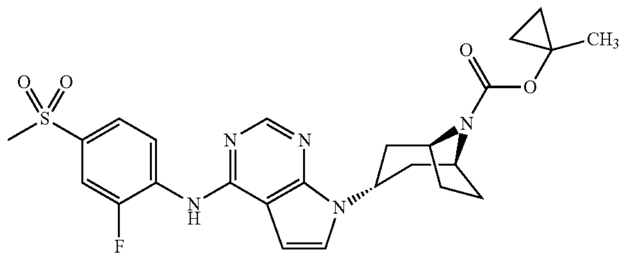 | 514 |
| 22 | 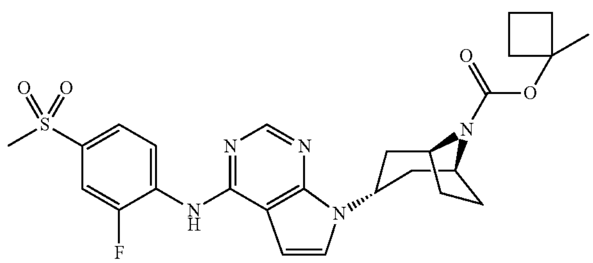 | 528 |
| 23 | | 475 | and pharmaceutically acceptable salts, solvates, esters and prodrugs thereof.

Methods for Making the Bicyclic Heterocycle Derivatives

Methods useful for making the Bicyclic Heterocycle Derivatives are set forth in the Examples below and generalized in Schemes 1-13. Alternative synthetic pathways and analogous structures will be apparent to those skilled in the art of organic synthesis.

Scheme 1 illustrates methods useful for making the compounds of formula iii, vi, viii, xi, xii, xiii and xvi, which are useful intermediates or making the Bicyclic Heterocycle Derivatives.

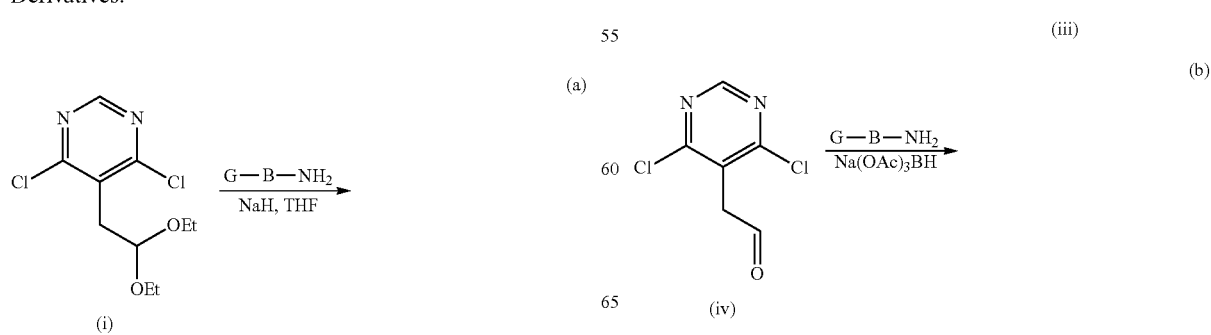

-continued

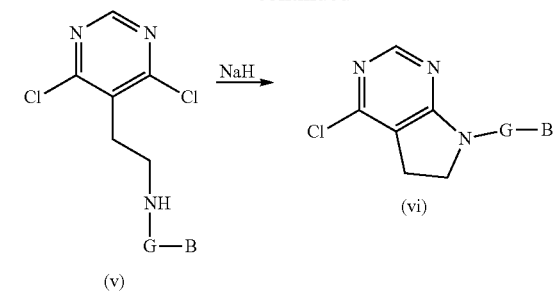
(v) → (vi)

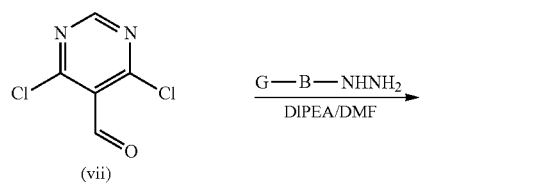
(vii) → (viii)

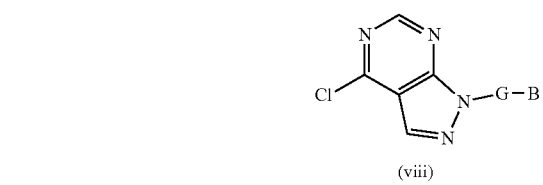
(ix) → (x)

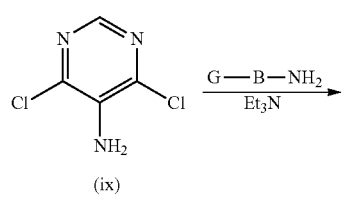
(x)

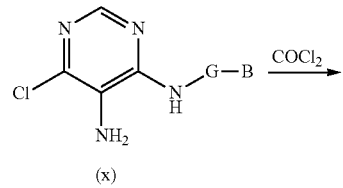
(xi)

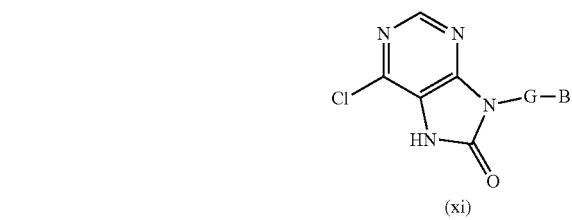
(ix) → (x)

(c)

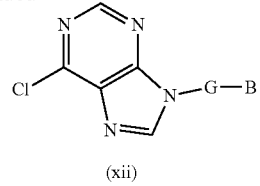
(xii)

(f)

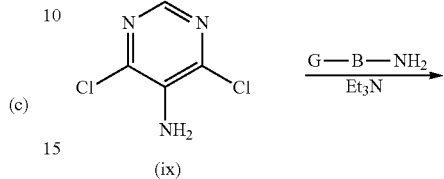
(ix)

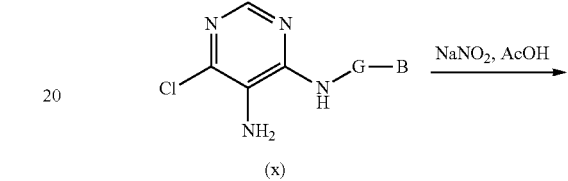
(x)

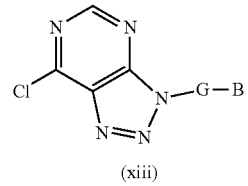
(xiii)

(d)

(g)

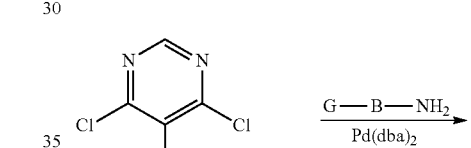
(xiv)

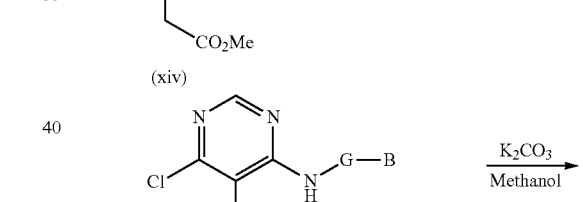
(xv)

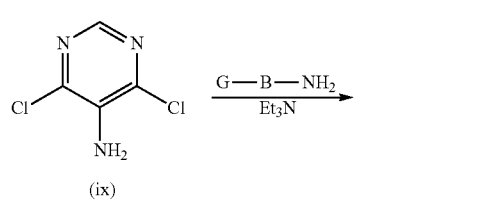

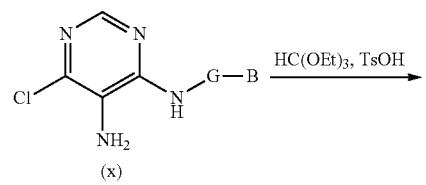

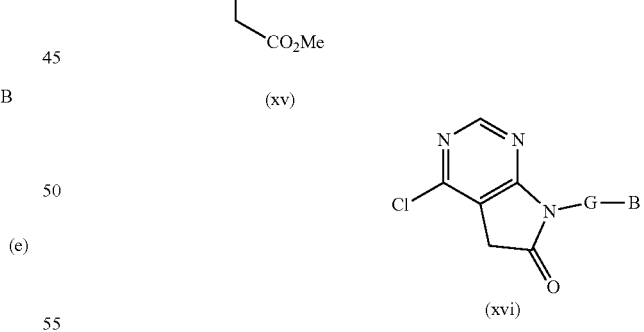
(xvi)

(e)

Scheme 1(a) shows a method useful for making the bicyclic core of the Bicyclic Heterocycle Derivatives wherein J and M are each —N—, L is —CH—; and —X—Y— is —CH═CH—.

A compound of formula i can be converted to its amino derivative of formula II, which can be subsequently cyclized in the presence of acid to provide the bicyclic core compounds of formula iii, which are useful intermediates for making the Bicyclic Heterocycle Derivatives wherein J and M are each —N—, L is —CH—; and —X—Y— is —CH═CH—.

Scheme 1(b) shows a method useful for making the bicyclic core of the Bicyclic Heterocycle Derivatives wherein J and M are each —N—, L is —CH—; and —X—Y— is —CH$_2$CH$_2$—.

An aldehyde compound of formula iv can be converted to its amino derivative of formula v, which can be subsequently cyclized in the presence of sodium hydride to provide the bicyclic core compounds of formula vi, which are useful intermediates for making the Bicyclic Heterocycle Derivatives wherein J and M are each —N—, L is —CH—; and —X—Y— is —CH$_2$CH$_2$—.

Scheme 1(c) shows a method useful for making the bicyclic core of the Bicyclic Heterocycle Derivatives wherein J and M are each —N—, L is —CH—; and —X—Y— is —CH=CN—.

An aldehyde compound of formula vii can be reacted with a compound of formula B-G-NHNH$_2$ in the presence of diisopropylethyl amine to form the bicyclic core compounds of formula viii, which are useful intermediates for making the Bicyclic Heterocycle Derivatives wherein J and M are each —N—, L is —CH—; and —X—Y— is —CH=N—.

Scheme 1(d) shows a method useful for making the bicyclic core of the Bicyclic Heterocycle Derivatives wherein J and M are each —N—, L is —CH—: and —X—Y— is —NHC(O)—.

An amine compound of formula ix can be converted to its diamino derivative of formula x, which can be subsequently cyclized upon reaction with oxalyl chloride to provide the bicyclic core compounds of formula xi, which are useful intermediates making the Bicyclic Heterocycle Derivatives wherein J and M are each —N—, L is —CH—; and —X—Y— is —NHC(O)—.

Scheme 1(e) shows a method useful for making the bicyclic core of the Bicyclic Heterocycle Derivatives wherein J and M are each —N—, L is —CH—; and —X—Y— is —N=CH—.

An amine compound of formula ix can be converted to its diamino derivative of formula x, which can be subsequently cyclized upon reaction with triethylorthoformate in the presence of p-toluenesulfonic acid to provide the bicyclic core compounds of formula xii, which are useful intermediates for making the Bicyclic Heterocycle Derivatives wherein) and M are each —N—, L is —CH—; and —X—Y— is —N=CH—.

Scheme 1(f) shows a method useful for making the bicyclic core of the Bicyclic Heterocycle Derivatives wherein J and M are each —N—, L is —CH—; and —X—Y— is —N=N—.

An amine compound of formula ix can be converted to its diamino derivative of formula x, which can be subsequently reacted with sodium nitrite in the presence of acetic acid to provide the bicyclic core compounds of formula xiii, which are useful intermediates for making the Bicyclic Heterocycle Derivatives wherein J and M are each —N—, L is —CH—; and —X—Y— is —N=N—.

Scheme 1(g) shows a method useful for making the bicyclic core of the Bicyclic Heterocycle Derivatives wherein J and M are each —N—, L is —CH—; and —X—Y— is —CH$_2$C(O)—.

An ester compound of formula xiv can be converted to its monoamine derivative of formula xv, which can be subsequently cyclized in the presence of potassium carbonate in methanol to provide the bicyclic core compounds of formula xvi, which are useful intermediates for making the Bicyclic Heterocycle Derivatives wherein J and M are each —N—, L is —CH—; and —X—Y— is —CH$_2$C(O)—.

Scheme 2 shows a method useful for converting hydroxy B group precursors (including, but not limited to the compounds shown below in Schemes 7-13) to their corresponding amino B group precursors. The amino B group precursors are useful for making the compounds of formula (I) wherein G is —NH—.

Scheme 2

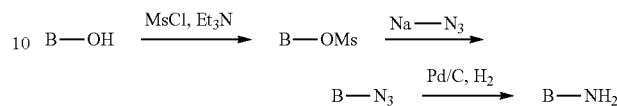

Scheme 3 illustrates a method that is useful for making the compounds of formula (I) by coupling a compound of formula R$^8$-AH (xvii) with an intermediate compound of formula iii, vi, viii, xi, xii, xiii or xvi in the presence of sodium hydride.

Scheme 3

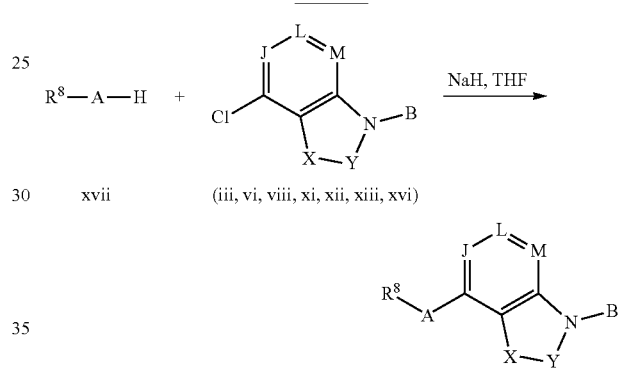

Scheme 4

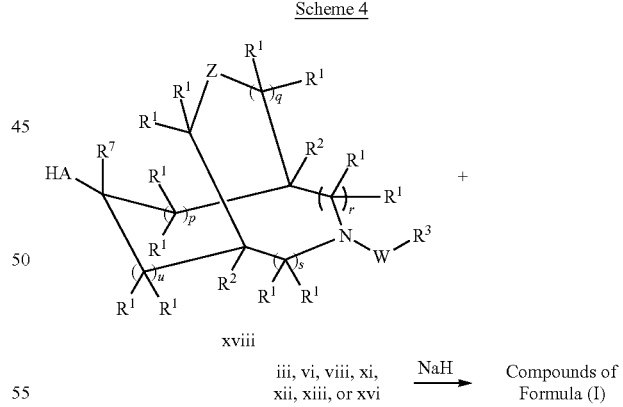

wherein R$^1$, R$^2$, R$^3$, R$^7$, W, Z, A, p, q, r, s and u are defined above for the compounds of formula (I).

A compound of formula xviii can be reacted with a bicyclic core intermediate of formula iii, vi, viii, xi, xiii or xvi in the presence of sodium hydride to provide the compounds of formula (I).

The compounds of formula xviii can be commercially available or can be prepared using methods well-known to one skilled in the art of organic chemistry.

Scheme 5 illustrates a general method useful for making the compounds of formula (II).

Scheme 5

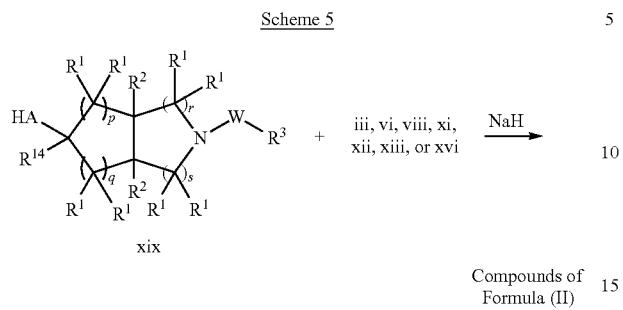

wherein $R^1$, $R^2$, $R^3$, $R^{14}$, W, A, p, q, r and s are defined above for the compounds of formula (II).

A compound of formula xix can be reacted with a bicyclic core intermediate of formula iii, vi, viii, xi, xiii or xvi in the presence of sodium hydride to provide the compounds of formula (II).

The compounds of formula xix can be commercially available or can be prepared using methods well-known to one skilled in the art of organic chemistry.

Scheme 6 illustrates a general method useful for making the compounds of formula (III).

Scheme 6

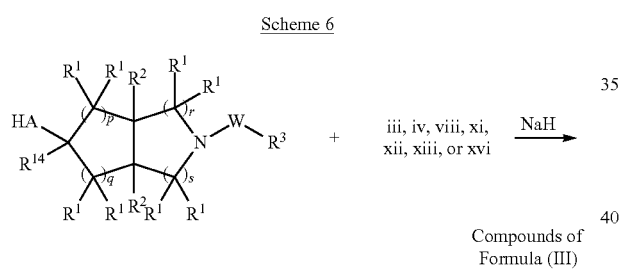

wherein $R^1$, $R^2$, $R^3$, $R^{14}$, W, Z, A, p, q, r and s are defined above for the compounds of formula (III).

A compound of formula xx can be reacted with a bicyclic core intermediate of formula iii, vi, viii, xi, xiii or xvi in the presence of sodium hydride to provide the compounds of formula (III).

The compounds of formula xx can be commercially available or can be prepared using methods well-known to one skilled in the art of organic chemistry.

Scheme 7 shows a method useful for making the compound of formula xxiv, which is useful for making the compounds of formula (III) wherein A is —O— and B is:

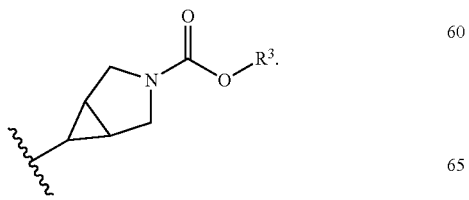

Scheme 7

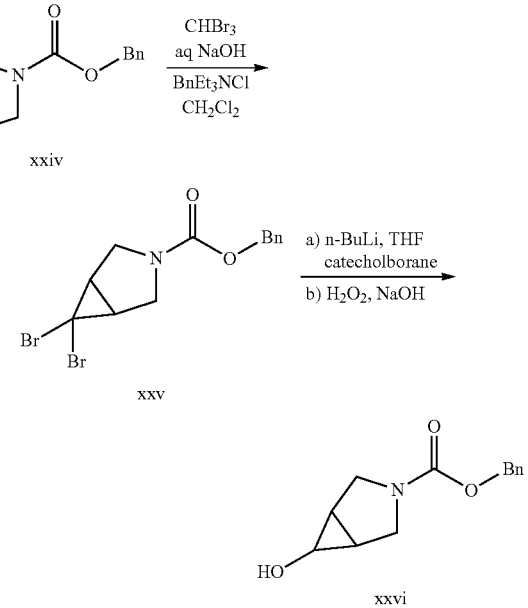

wherein Bn is benzyl.

The compound of formula viii is converted to compound x using the two-step process shown above, which is described in *J. Med. Chem.* 48:5009 (2005).

Scheme 8 shows a method useful for making the compound of formula xxvii, which is useful for making the compounds of formula (III) wherein A is —O— and B is:

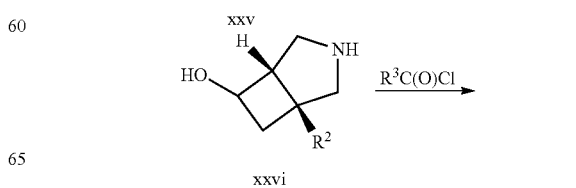

Scheme 8

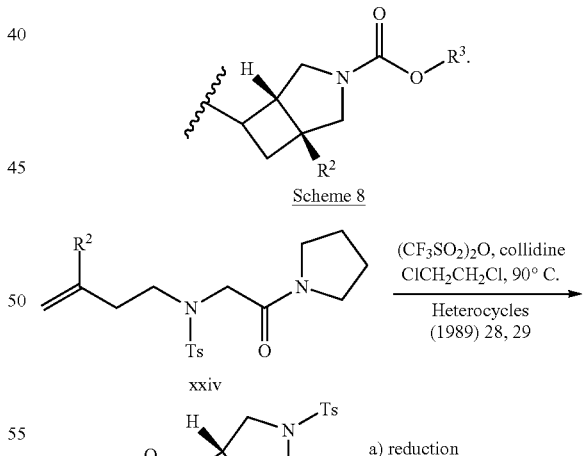

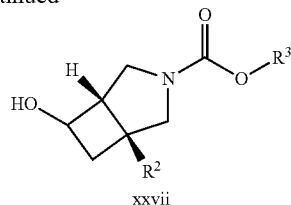

wherein R² is H or alkyl and R³ is defined above for the Bicyclic Heterocycle Derivatives of formula (II).

A compound of formula xxiv is converted to a compound of formula xxv using the method described in *Heterocycles* 28:29 (1989). The ketone group of the compound of formula xxv is subsequently reduced using NaBH₄, for example, and then the tosyl group is removed to provide the compound of formula xxvi, following the method described in International Publication No. WO 94/15933. Finally, a compound of formula xxvi can be reacted with a carbonyl chloride of formula R³C(O)Cl to provide the compounds of formula xxvii.

Scheme 9 shows a method useful for making the compound of formula xxxi, which is useful for making the compounds of formula (II) wherein A is —O— and B is:

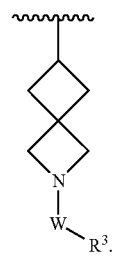

Scheme 9

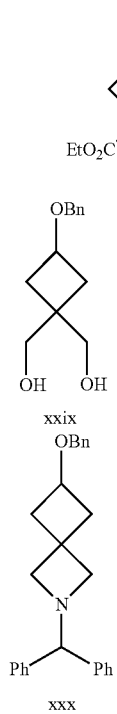

The ethyl ester groups of compound xxviii are reduced using lithium aluminum hydride (LAH) to provide the diol compound xxix. Compound xxix is then converted to spirocyclic compound xxx via a two step process. The hydroxy groups of xxx are first converted to their respective —O-triflates by reacting xxix with an excess of triflic anhydride in the presence of DIEA, then the resulting di-O-triflate intermediate is reacted with benzhydryl methylamine in the presence of diisopropylethyl amine to provide compound xxx. The benzhydryl group of xxx is then removed via catalytic hydrogenation in the presence of ammonium formate and the resulting amine is protected as its BOC derivative. The benzyl protected alcohol group of the resulting BOC-protected intermediate is then removed via catalytic hydrogenation to provide hydroxy intermediate xxxi.

Scheme 10 shows a method useful for making the compound of formula xxxvii, which is useful for making the compounds of formula (I) wherein A is —O— and B is:

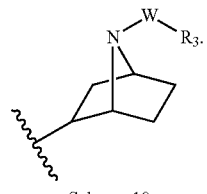

Scheme 10

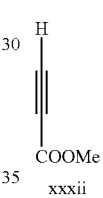  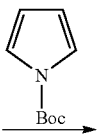

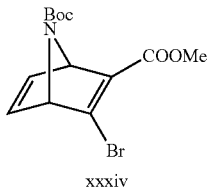

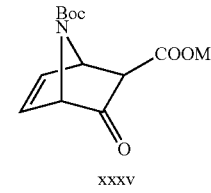

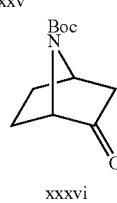

endo/exo = 2:1

Compound xxxii is brominated using NBS to provide the bromo compound xxxiii, which is then subjected to a cycloaddition reaction with N-Boc pyrrole to provide cyclic compound xxxiv. Compound xxxiv is then converted to ketoester xxxv, which is then decarboxylated to provide ketone xxxvi. Compound xxxvi is then reduced using sodium borohydride to provide compound xxxvii.

Scheme 11 shows a method useful for making the compound of formula xli, which is useful for making the compounds of formula (I) wherein A is —O— and B is:

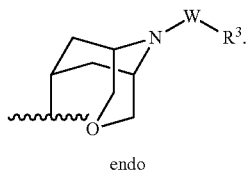

endo

Scheme 11

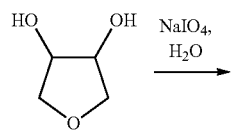

xxxviii

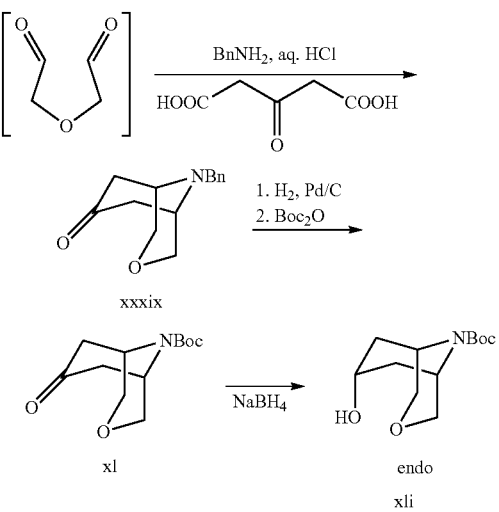

Diol xxxviii is subjected to an oxidative cleavage using sodium periodate and the resulting dialdehyde intermediate is then cyclized by reacting it with 1,3-acetone dicarboxylic acid in the and benzylamine to provide cyclic compound xxxix. The benzyl-protected amine of compound xxxix is then deprotected and reprotected as its Boc derivative xl. Compound xl is then reduced using sodium borahydride to provide compound xli.

Scheme 12 shows a method useful for making the compound of formula xliv, which is useful for making the compounds of formula (I) wherein A is —O— and B is:

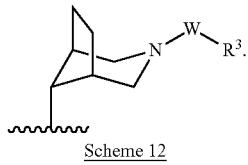

Scheme 12

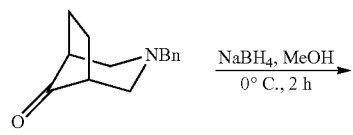

(commercial)

xlii

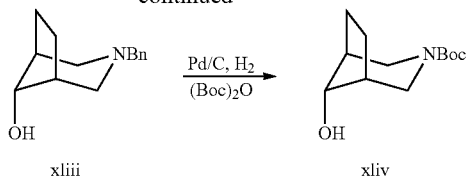

Compound xlii is reduced using sodium borohydride to provide alcohol xliii, the benzyl amine group of which is subsequently deprotected using catalytic hydrogenation, then reprotected as its Boc derivative xliv.

Scheme 13 shows a method useful for making the compound of formula xlviii, which is useful for making the compounds of formula (I) wherein A is —O— and B is:

Scheme 13

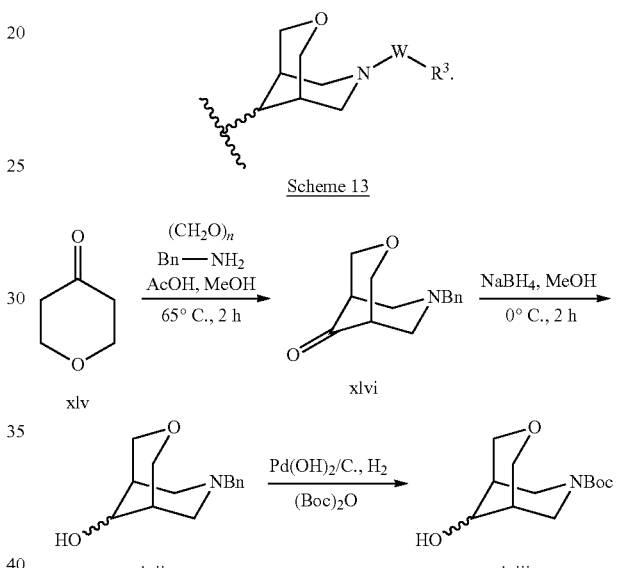

Compound xlv is cyclized to provide bicyclic compound xlvi. Compound xlvi is then reduced using sodium borohydride to provide alcohol xivii, the benzyl amine group of which is subsequently deprotected using catalytic hydrogenation, then reprotected as its Boc deriviative xlviii.

The starting materials and reagents depicted in Schemes 1-13 above are either available from commercial suppliers such as Sigma-Aldrich (St. Louis, Mo.) and Acros Organics Co. (Fair Lawn, N.J.), ear can be prepared using methods well-known to those of skill in the art of organic synthesis.

One skilled in the art will recognize that the synthesis of the Bicyclic Heterocycle Derivatives of the present invention may require the need for the protection of certain functional groups (i.e., derivatization for the purpose of chemical compatibility with a particular reaction condition). Suitable protecting groups for the various functional groups of the Bicyclic Heterocycle Derivatives and methods for their installation and removal may be found in Greene et al., *Protective Groups in Organic Synthesis*, Wiley-Interscience, New York, (1999).

EXAMPLES

The following examples exemplify illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received. Reagents and intermediates that are not commercially available were prepared in the manner described below. $^1$H NMR spectra were obtained on a Gemini AS-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

Example 1

Preparation of Compound 6

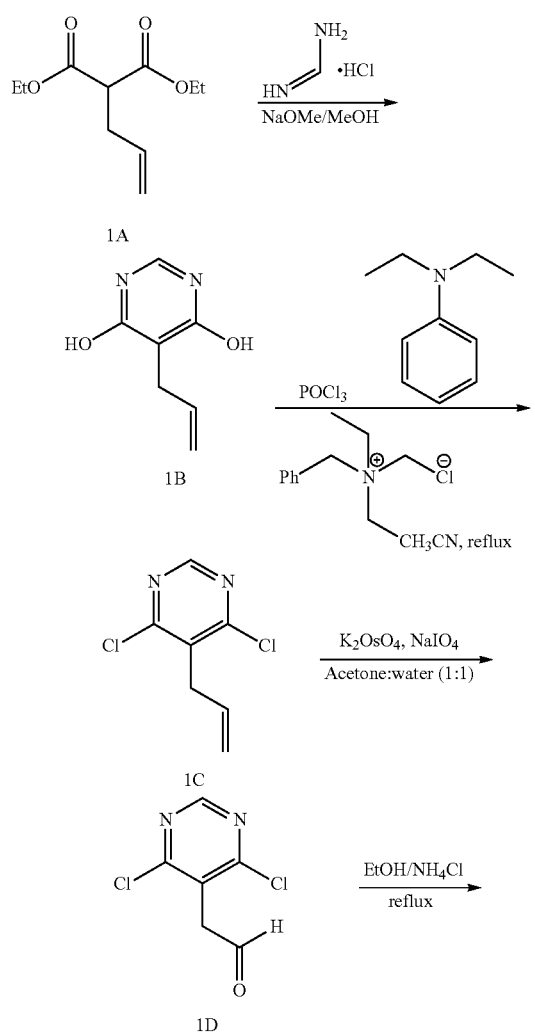

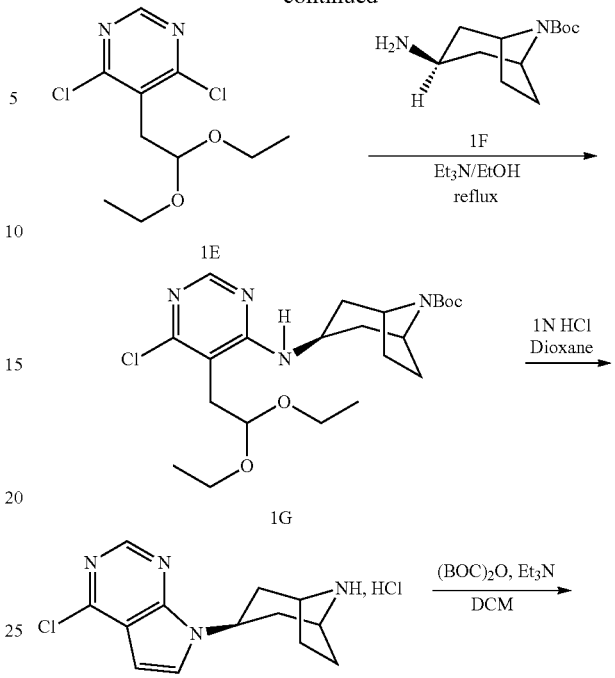

Step 1—Synthesis of Compound 1B

To a cold suspension of sodium methoxide (30% solution in methanol) (32.4 g, 599.31 mmol) in methanol (about 300 rut) at 5° C. was added formamidine hydrochloride (10.05 g, 124.86 mmol) and the resulting reactor was allowed to stir for 10 minutes. Diethyl allylmalonate (1A, 25 g, 124.85 mmol) was then added and the resulting reaction was allowed to stir for about 15 hours at room temperature. The reaction mixture was concentrated in vacuo and the resulting residue was dissolved in ice cold water (about 100 mL) and acidified to pH=7 using 2N HCl. The white precipitate obtained was filtered, washed with water and dried under vacuum to provide compound 1.8 (13.52 g, 71.19%).

Step 2—Synthesis of Compound 1C

Compound 1B (13.5 g, 88.73 mmol), diethylaniline (15.9 g, 106.48 mmol), benzyltriethyl ammonium chloride (40.42 g, 177.46 mmol) and phosphorous oxychloride (74.0 g, 482.68 mmol) were taken up in acetonitrile (about 260 mL) and the resulting reaction was heated to reflux and allowed to stir at this temperature for 15 hours. The reaction mixture was cooled, poured over crushed ice and washed sequentially with saturated aqueous sodium bicarbonate, brine and water. The aqueous layer was extracted with EtOAc and the combined organic layers were dried over anhydrous sodium sulfate, filtered and concentrated in vacuo. The residue obtained was purified using flash column chromatography on silica gel ($CH_2Cl_2$) and the product 1C was isolated (9.73 g, 57.95%).

Step 3—Synthesis of Compound 1D

Compound 1C (9.73 g, 51.47 mmol) was dissolved in a mixture of acetone:water (1:1, 290 mL) and to the resulting solution was added potassium osmate dihydrate (0.64 g, 1.75 mmol). The resulting solution was allowed so stir for 5 minutes, then solid sodium periodate (44 g, 205.37 mmol) was added in 4 portions over a 1 hour period. The temperature of the reaction didn't exceed 40° C. during this addition. The resulting suspension was allowed to stir for 1 hour as the reaction cooled to room temperature on its own. The reaction mixture was then filtered and the filtrate was concentrated in vacuo to remove acetone. The resulting aqueous solution was extracted 2 times with dichloromethane and the combined organic layers were washed with 10% sodium thiosulfate solution, dried over anhydrous sodium sulfate, filtered and concentrated in vacuo to provide compound 1D (8.16 g, 83.01%).

Step 4—Synthesis of Compound 1E

Compound 1D (5.12 g, 26.80 mmol) was dissolved in ethanol (130 mL) and to the resulting solution was added ammonium chloride (0.29 g, 5.36 mmol). The resulting reaction was heated to reflux and allowed to stir at this temperature for 15 hours, then the reaction mixture was cooled to room temperature and concentrated in vacuo. The resulting residue was dissolved in ethyl acetate, filtered, concentrated in vacuo and the residue obtained was purified using flash column chromatography on silica gel (hexane/acetone (80/20)) and the product 1E (5.6 g, 78.76%) was isolated.

Step 5—Synthesis of Compound 1G

Compound 1E (0.39 g, 1.24 mmol) was taken up in ethanol (14 mL) and to the resulting solution was added tert-butyl 3-amino-8-azabicylco[3.2.1]octane-8-carboxylate (1F, 0.27 g, 1.19 mmol), followed by triethylamine 1 mL). The resulting reaction was heated to reflux and allowed to stir at this temperature for 15 hours, then the reaction mixture was cooled to room temperature and concentrated in vacuo. The residue obtained was purified using flash column chromatography on silica gel (hexane/acetone (80/20)) and the product 1G (0.4 g, 73.11%) was isolated.

Step 6—Synthesis of Compound 1H

Compound 1G (0.39 g, 0.86 mmol) was dissolved in dioxane (10 mL) and to the resulting solution was added 1N hydrochloric acid (4 mL, aqueous). The resulting reaction was allowed to stir for about 72 hours at room temperature, then concentrated in vacuo to provide compound 1H as the hydrochloride salt (0.25 g, 87.73%).

Step 7—Synthesis of Compound 1J

To a solution of amine hydrochloride 1H (0.23 g, 0.75 mmol) in dichloromethane (8 mL) was added triethylamine (0.36 mL, 2.57 mmol) and the resulting solution was allowed to stir for 5 minutes. Di-tert-butyl dicarbonate (0.20 g, 0.93 mmol) was added and the resulting mixture was allowed to stir at room temperature for 1 hour. The reaction was quenched with saturated ammonium chloride solution and extracted 2 times with dichloromethane. The combined organic layers were dried over anhydrous sodium sulfate, filtered and concentrated in vacuo. The residue obtained was purified using flash column chromatography on silica gel (hexane/acetone (80/20)) and the product 1J (0.26 g, 96.38%) was isolated.

Step 8—Synthesis of Compound 6

To a stirred solution of sodium hydride (0.08 g, 0.2.07 mmol) in tetrahydrofuran (6 ml) in a sealed tube was added a solution of 4-amino-3-chloro benzonitrile (0.06 g, 0.42 mmol) tetrahydrofuran (9 mL) and the resulting reaction was allowed to stir for about 45 minutes. The reaction mixture was then cooled to 0 and a solution of compound 1J (0.15 g, 0.41 mmol) in tetrahydrofuran (9 mL) was added and the resulting reaction was heated to reflux and allowed to stir at this temperature for about 15 hours. The reaction was cooled to room temperature, quenched with water and extracted 2 times with ethyl acetate. The combined organic layers were dried over anhydrous sodium sulfate, filtered, concentrated in vacuo. The resulting residue was purified using preparative thin layer chromatography (hexane/acetone (80/20)) to provide compound 6 (0.12 g, 60.13%).

Example 2

Preparation of Compound 1

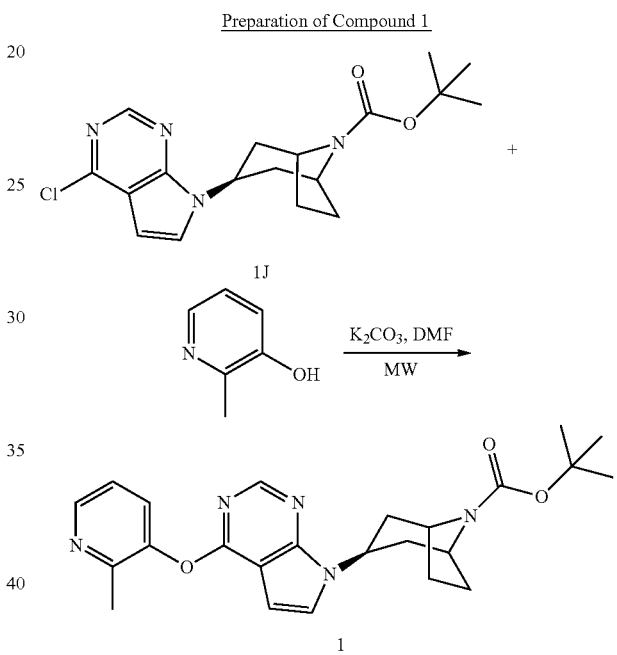

To a solution of compound 1J (0.0185 g, 0.051 mmol) in DMF (2.0 mL) was added 3-hydroxy-2-methyl-pyridine (0.0056 g, 0.0513 mmol) and $K_2CO_3$ (0.021 g, 0.153 mmol) and the resulting reaction mixture was treated under microwave conditions at high absorption for 1 hour. The reaction was concentrated in vacuo and the resulting residue was purified using preparative TLC (5% methanol/dichloromethane) to provide compound 1 (0.012 g, 0.028 mmol).

Example 3

Preparation of Comound 9

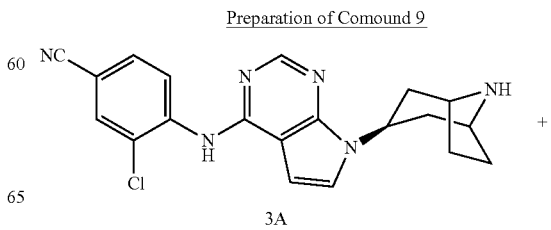

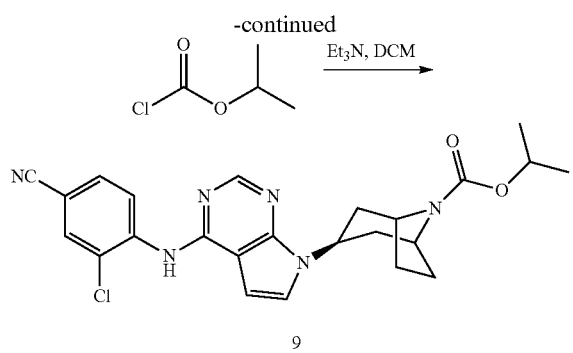

Step 1—Synthesis of Compound 3A

To a solution of compound 6 (0.12 g, 0.25 mmol) in dichloromethane (3 mL) was added trifluoroacetic acid (0.3 mL) and the resulting reaction was allowed to stir for about 30 minutes at room temperature. The reaction mixture was evaporated to dryness to remove excess solvent and trifluoroacetic acid to provide the free amine 3A (0.09 g, 100%).

Step 2—Synthesis of Compound 9

To a stirred solution of compound 3A (0.02 g, 0.06 mmol) in dichloromethane mL) was added triethylamine (0.03 mL, 0.18 mmol) and the resulting reaction was allowed to stir for about 5 minutes. Isopropyl chloroformate (1M solution in toluene, 0.07 mL, 0.07 mmol) was then added and the resulting reaction was allowed to stir for about 2 hours. The reaction was quenched with saturated ammonium chloride solution and extracted 2 times with dichloromethane. The combined organic layers was dried over anhydrous sodium sulfate, filtered, concentrated in vacuo and the residue obtained was purified using preparative thin layer chromatography (hexane/ethyl acetate (55/45)) to provide compound 9 (0.023 g, 77.42%).

Example 4

Preparation of Comound 5

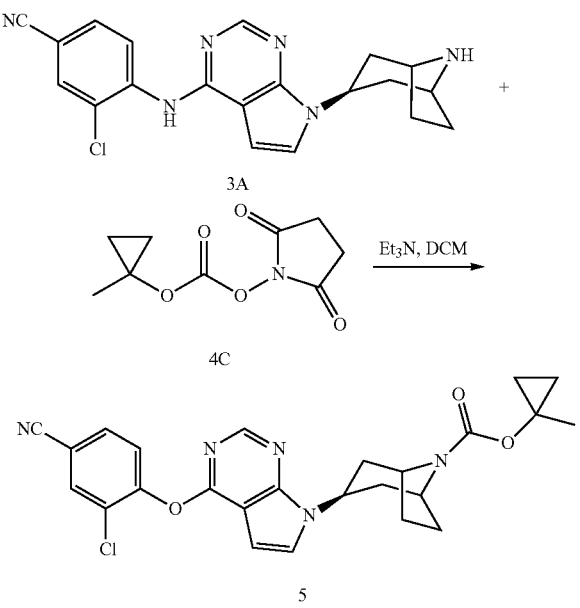

Step 1—Synthesis of Compound 4C

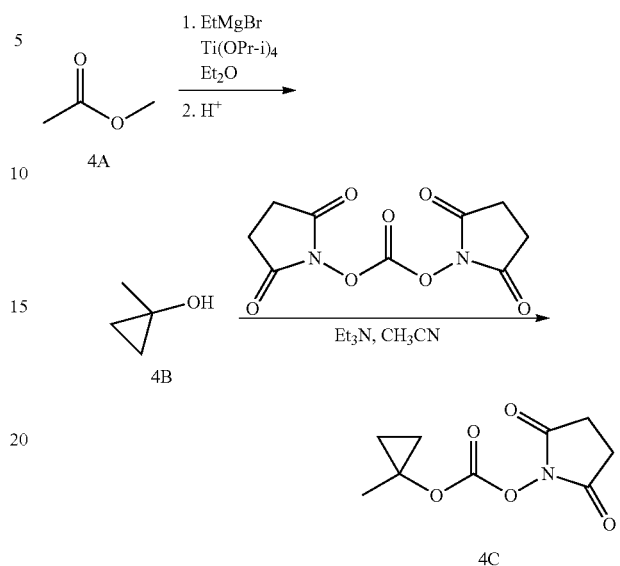

To a stirred solution of compound 4A (1.98 g, 25 mmol) in ether (80 mL) and titanium isopropoxide (1.7 mL, 5.75 mmol) was added a solution of ethyl magnesium bromide (17.66 mL, 53 mmol) in ether (60 mL) slowly over a period of 1 hour at room temperature (ice bath was used to maintain room temperature) and stirring continued for 15 more minutes. The mixture was poured into cooled 10% aqueous sulfuric acid (250 mL) and the product was extracted with 3 times with ether. The combined organic layers were washed with water, dried over anhydrous sodium sulfate, filtered and concentrated in vacuo to about 25% of the original volume to provide compound 4B in solution, which was diluted with acetonitrile (80 mL) and to the resulting solution was added N,N'-disuccinimidyl carbonate (12.8 g, 49.9 mmol). The resulting reaction was allowed to stir for 10 minutes, then triethylamine (10.5 mL, 74.88 mmol) was added and the resulting reaction was allowed to stir for about 15 hours at room temperature under nitrogen atmosphere. The reaction mixture was washed with saturated sodium bicarbonate solution and extracted with ethyl acetate. The organic layer was collected, dried over anhydrous magnesium sulfate, filtered and concentrated in vacuo to provide compound 4C (0.6 g, 12%).

Step 2—Synthesis of Compound 5

To a stirred solution of amine 3A (0.024 g, 0.06 mmol) in dichloromethane (3 mL) was added triethylamine (0.03 mL, 0.18 mmol) and the resulting mixture was allowed to stir for about 5 minutes. Compound 4C (0.026 g, 0.12 mmol) was then added and the resulting reaction was allowed to stir at room temperature for about 2 hours. The reaction was quenched with saturated ammonium chloride solution and extracted 2 times with dichloromethane. The combined organic extracts were dried over anhydrous sodium sulfate, filtered, concentrated in vacuo, and the resulting residue was purified using preparative thin layer chromatography (hexane/ethyl acetate (50/50)) to provide compound 5 (0.029 g, 93.33%).

Example 5

Preparation of Compound 8

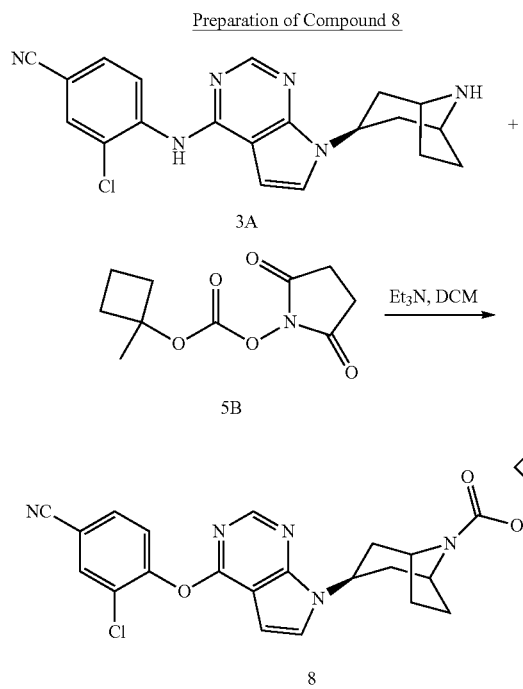

Step 1—Synthesis of Compound 5B

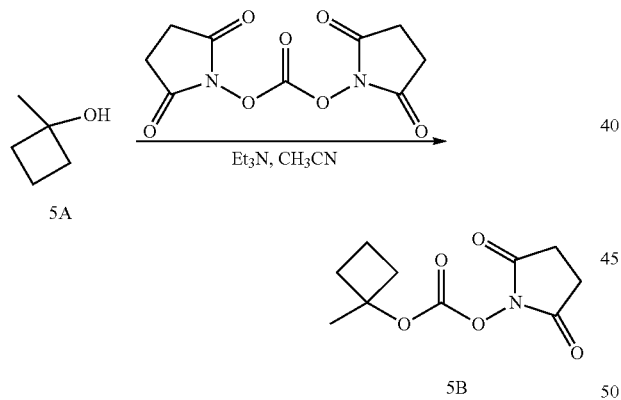

Using the method described in Example 4, Step 1 and substituting compound 5A for compound 4B, compound 5B was prepared 10.5 g,

Step 2—Synthesis of Compound 5C

To a stirred solution of compound 3A (0.024 g, 0.06 mmol) in dichloromethane (i) mL) was added triethylamine (0.03 mL, 0.19 mmol) and the resulting mixture was allowed to stir for about 5 minutes. Compound 5B (0.028 g, 0.12 mmol) was then added and the reaction was allowed to stir at room temperature for additional 2 hours. The reaction was quenched with saturated ammonium chloride solution and extracted 2 times with dichloromethane. The combined organic extracts were dried over anhydrous sodium sulfate, filtered, concentrated in vacuo, and the resulting residue was purified using preparative thin layer chromatography (hexane/ethyl acetate (50/50)) to provide compound 8 (0.021 g, 67.74%).

Example 6

Preparation of Compound 10

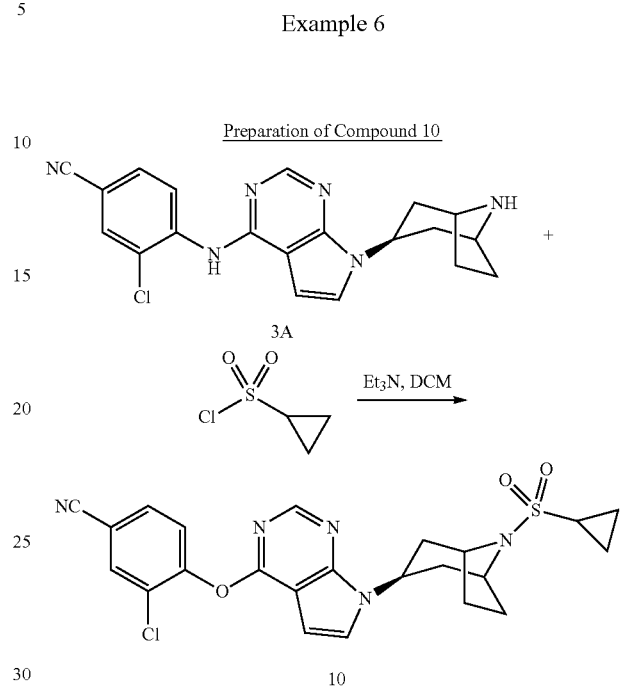

To a stirred solution of compound 3A (0.024 g, 0.06 mmol) in dichloromethane (2 mL) was added triethylamine (0.03 mL, 0.18 mmol) and the resulting reaction was allowed to stir for 5 minutes. Cyclopropane sulfonyl chloride (0.01 mL, 0.07 mmol) was added and the resulting reaction was allowed to stir for an additional 2 hours. The reaction was quenched with saturated ammonium chloride and extracted 2 times with dichloromethane. The combined organic extracts were dried over anhydrous sodium sulfate, filtered, concentrated in vacuo, and the resulting residue was purified using preparative thin layer chromatography (hexane/ethyl acetate (50/50)) to provide compound 10 (0.01 g, 32.8%).

Example 7

Preparation of Compound 4

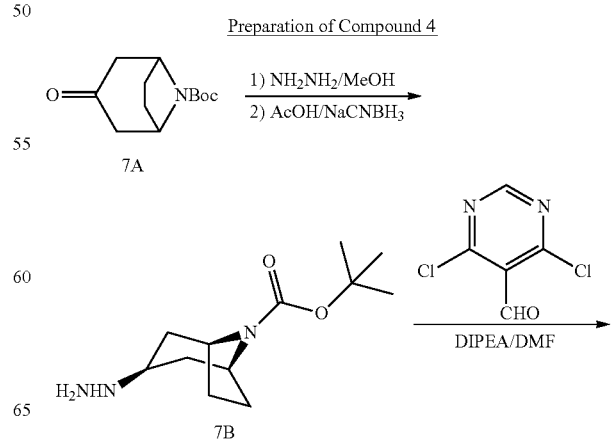

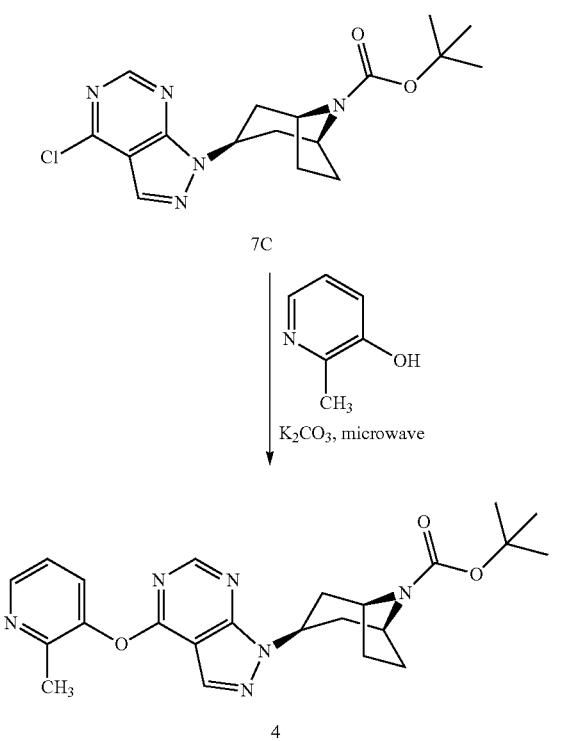

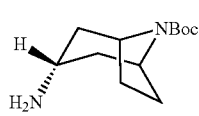

Example 8

Preparation of Compound 15

Compound 15 was synthesized using the method described in Scheme 1 and by replacing the exo-amine 1F in step 5 with the endo-amine 8A.

Example 9

Preparation of Compounds 13 and 17

Compounds 13 and 17 were prepared using the method described in Example 3 and by substituting the appropriate reactants.

Example 10

Preparation of Compounds 12, 20 and 21

Compounds 12, 20 and 21 were prepared using the method described in Example 4 and by substituting the appropriate reactants.

Example 11

Preparation of Compounds 11, 19 and 22

Compounds 11, 19 and 22 were prepared using the method described in Example 5 and by substituting the appropriate reactants.

Example 12

Preparation of Compounds 14 and 18

Compound 14 and 18 were prepared using the method described in Example 6 and by substituting the appropriate reactants.

Example 13 cAMP Assay

The ability of illustrative compounds of the invention to activate GPR119 and stimulate increases in cAMP levels was determined using the LANCE™ cAMP kit (Perkin Elmer). HEK293 cells expressing human GPR119 were maintained in culture flasks at 37° C./5% $CO_2$ in DMEM containing 10% fetal bovine serum, 100 U/ml Pen/Strep, and 0.5 mg/ml geneticin. The media was changed to Optimem and cells were incubated overnight at 37° C./5% $CO_2$. The Optimem was then aspirated and the cells were removed from the flasks using room temperature Hank's balanced saline solution (HBSS). The cells were pelleted using centrifugation (1300 rpm, 7 minutes, room temperature), then resuspended in stimulation buffer (HBSS, 0.1% BSA, 5 mM HEPES, 15 μM RO-20) at $2.5 \times 10^6$ cells/mL. Alexa Fluor 647-anti cAMP antibody (1:100) was then added to the cell suspension and incubated for 30 minutes. A representative Bicyclic Hetero- Step 1—Synthesis of Compound 7B To a solution of Boc-nortropinone (7A, 2.0 g) and anhydrous hydrazine (306.5 μl, 1.1 eq) in MeOH (6 mL), was added acetic acid (300 μl). The resulting reaction was allowed to stir at room temperature for 10 minutes, then heated at 60° C. and allowed to stir at this temperature for 1 hour. The reaction mixture was then cooled to room temperature and $NaCNBH_3$ (1.76 g, 3 eq) was added. The resulting reaction was heated at 60° C., under nitrogen atmosphere and allowed to stir at this temperature for 17 hours, then cooled to room temperature and concentrated in vacuo to provide a crude yellow oil. The crude oil was partitioned between water and ethyl acetate and the organic layer was washed with brine, dried over $MgSO_4$ and concentrated in vacuo to provide compound 7B as a yellow oil (2.09 g, 97%).

Step 2—Synthesis of Compound 7C

To a solution of 4,6-Dichloro-pyrimidine-5-carbaldehyde (500 mg) in DMF (5 mL) was added DIPEA (738 μl, 1.5 eq), followed by compound 7B (886 mg, 1.3 eq). The resulting reaction was allowed to stir at room temperature for 1.5 hours, then was heated to 60° C. and allowed to stir at this temperature for 2 hours. The reaction mixture was then cooled to torn temperature and concentrated in vacuo. The resulting residue was purified using preparative thin-layer chromatography (3% $MeOH/CH_2Cl_2$) to provide compound 7C as a yellow it (385 mg, 37%).

Step 3—Synthesis of Compound 4

Using the method described in Example 2 and substituting compound 7C for compound 1J, compound 4 was synthesized.

cycle Derivative (6 μl at 2× concentration) in stimulation buffer containing 2% DMSO were then added to white 384 well Matrix plates. Cell suspension mix (6 μl) was added to each well and incubated with the Bicyclic Heterocycle Derivative for 30 minutes. A cAMP standard curve was also created in each assay according to the kit protocol. Standard concentrations of cAMP in stimulation buffer (6 μl) were added to white 384 well plates. Subsequently, 6 μl of 1:100 anti-cAMP antibody was added to each well. Following the 30 minute incubation period, 12 μl of detection mix (included in kit) was added to all wells and incubated for 2-3 hours at room temperature. Fluorescence was detected on the plates using an Envision instrument. The level of cAMP in each well is determined by extrapolation from the cAMP standard curve.

Using this assay, $EC_{50}$ values for various illustrative Bicyclic Heterocycle Derivatives of the present invention were calculated and range from about 75 nM to about 1.3 μM.

Example 14

Effect of the Compounds of the Invention in Oral Glucose Tolerance Test

Male C57Bl/6NCrl mice (6-8 week old) were fasted overnight and randomly dosed with either vehicle (20% hydroxypropyl-β-cyclodextrin) or a representative compound of the invention (at 3, 10 or 30 mg/kg) via oral gavage (n=8 mice/group). Glucose was administered to the animals 30 minutes post-dosing (3 g/kg p.o.). Blood glucose was measured prior to administration of test compound and glucose, and at 20 minutes after glucose administration using a hand-held glucometer (Ascensia Elite, Bayer).

Using this protocol, the effects of various Bicyclic Heterocycle Derivatives of the present invention were measured and indicate that the Bicyclic Heterocycle Derivatives of the present invention are effective in lowering blood glucose levels after glucose challenge.

Example 15

Effect of the Compounds of the Invention in an Animal Model of Diabetes

Four week old male C57Bl/6NCrl mice can be used to generate a nongenetic model of type 2 diabetes mellitus as previously described (*Metabolism* 47(6): 663-668, 1998). Briefly, mice are made insulin resistant by high fat feeding (60% of kcal as fat) and hyperglycemia is then induced using a low dose of streptozotocin (100 mg/kg i.p.). Eight weeks after streptozotocin administration, the diabetic mice are placed into one of 4 groups (n=13/gp) receiving the following treatments: vehicle (20% hydroxypropyl-β-cyclodextrin p.o.), a representative compound of the invention (30 mg/kg p.o.), glipizide (20 mg/kg p.o.) or exendin-4 (10 ug/kg i.p.). Mice are dosed once daily for 13 consecutive days, and blood glucose levels are measured daily using, for example, a hand held glucometer, to determine the effects of the test compound(s) on glucose levels of the diabetic animals.

Uses of the Bicyclic Heterocycle Derivatives

The Bicyclic Heterocycle Derivatives are useful in human and veterinary medicine for treating or preventing a Condition in a patient. In accordance with the invention, the Bicyclic Heterocycle Derivatives can be administered to a patient in need of treatment or prevention of a Condition.

Treatment of Obesity and Obesity-Related Disorders

The Bicyclic Heterocycle Derivatives can also be useful for treating obesity or an obesity-related disorder.

Accordingly, in one embodiment, the invention provides methods for treating obesity or an obesity-related disorder in a patient, wherein the method comprises administering to the patient an effective amount of one or more Bicyclic Heterocycle Derivatives, or a pharmaceutically acceptable salt, solvate, ester or prodrug thereof.

Treatment of Diabetes

The Bicyclic Heterocycle Derivatives are useful for treating diabetes in a patient. Accordingly, in one embodiment, the present invention provides a method for treating diabetes in a patient, comprising administering to the patient an effective amount of one or more Bicyclic Heterocycle Derivatives.

Examples of diabetes treatable or preventable using the Bicyclic Heterocycle Derivatives include, but are not limited to, type I diabetes (insulin-dependent diabetes mellitus), type II diabetes (non-insulin dependent diabetes mellitus), gestational diabetes, autoimmune diabetes, insulinopathies, idiopathic type I diabetes (Type 1b), latent autoimmumne diabetes in adults, early-onset type 2 diabetes (ECM), youth-onset atypical diabetes (YOAD), maturity onset diabetes of the young (MODY), malnutrition-related diabetes, diabetes due to pancreatic disease, diabetes associated with other endocrine diseases (such as Cushing's Syndrome, acromegaly, pheochromocytoma, glucagonoma, primary aldosteronism or somatostatinoma), type A insulin resistance syndrome, type B insulin resistance syndrome, lipatrophic diabetes, diabetes induced by β-cell toxins, and diabetes induced by drug therapy (such as diabetes induced by antipsychotic agents).

In one embodiment, the diabetes is type I diabetes.

In another embodiment, the diabetes is type II diabetes.

Treatment of a Diabetic Complication

The Bicyclic Heterocycle Derivatives are also useful for treating a diabetic complication in a patient. Accordingly, in one embodiment, the present invention provides a method for treating a diabetic complication in a patient, comprising administering to the patient an effective amount of one or more Bicyclic Heterocycle Derivatives.

Examples of diabetic complications treatable or preventable using the Bicyclic Heterocycle Derivatives include, but are not limited to, diabetic cataract, glaucoma, retinopathy, aneuropathy (such as diabetic neuropathy, polyneuropathy, mononeuropathy, autonomic neuropathy, microaluminuria and progressive diabetic neuropathyl), nephropathy, gangrene of the feet, immune-complex vasculitis, systemic lupsus erythematosus (SLE), atherosclerotic coronary arterial disease, peripheral arterial disease, nonketotic hyperglycemic-hyperosmolar coma, foot ulcers, joint problems, a skin or mucous membrane complication (such as an infection, a shin spot, a candidal infection or necrobiosis lipoidica diabeticorumobesity), hyperlipidemia, cataract, hypertension, syndrome of insulin resistance, coronary artery disease, a fungal infection, a bacterial infection, and cardiomyopathy.

Treatment of a Metabolic Disorder

The Bicyclic Heterocycle Derivatives can also be useful for treating a metabolic disorder. Examples of metabolic disorders treatable include, but are not limited to, metabolic syndrome (also known as "Syndrome X"), impaired glucose tolerance, impaired fasting glucose, hypercholesterolemia, hyperlipidemia, hypertriglyceridemia, low HDL levels, hypertension, phenylketonuria, post-prandial lipidemia, a glycogen-storage disease, Gaucher's Disease, Tay-Sachs Disease, Niemann-Pick Disease, ketosis and acidosis.

Accordingly, in one embodiment, the invention provides methods for treating a metabolic disorder in a patient, wherein the method comprises administering to the patient an effective amount of one or more Bicyclic Heterocycle Derivatives, or a pharmaceutically acceptable salt, solvate, ester or prodrug thereof.

In one embodiment, the metabolic disorder is hypercholesterolemia.

In another embodiment, the metabolic disorder is hyperlipidemia.

In another embodiment, the metabolic disorder is hypertriglyceridemia.

In still another embodiment, the metabolic disorder is metabolic syndrome.

In a further embodiment, the metabolic disorder is low HDL levels.

Methods for Treating a Cardiovascular Disease

The Bicycle Heterocycle Derivatives are useful for treating or preventing a cardiovascular disease in a patient.

Accordingly, in one embodiment, the present invention provides a method for treating a cardiovascular disease in a patient, comprising administering to the patient an effective amount of one or more Bicyclic Heterocycle Derivatives.

Illustrative examples of cardiovascular diseases treatable or preventable using the present methods, include, but are not limited to atherosclerosis, congestive heart failure, cardiac arrhythmia, myocardial infarction, atrial fibrillation, atrial flutter, circulatory shock, left ventricular hypertrophy, ventricular tachycardia, supraventricular tachycardia, coronary artery disease, angina, infective endocarditis, non-infective endocarditis, cardiomyopathy, peripheral artery disease, Reynaud's phenomenon, deep venous thrombosis, aortic stenosis, mitral stenosis, pulmonic stenosis and tricuspid stenosis.

In one embodiment, the cardiovascular disease is atherosclerosis.

In another embodiment, the cardiovascular disease is congestive heart failure.

In another embodiment, the cardiovascular disease is coronary artery disease.

Combination Therapy

In one embodiment, the present invention provides methods for treating a Condition in a patient, the method comprising administering to the patient one or more Bicycle Heterocycle Derivatives, or a pharmaceutically acceptable salt, solvate, ester or prodrug thereof and at least one additional therapeutic agent that is not a Bicyclic Heterocycle Derivative, wherein the amounts administered are together effective to treat or prevent a Condition.

Non-limiting examples of additional therapeutic agents useful in the present methods for treating or preventing a Condition include, anti-obesity agents, antidiabetic agents, any agent useful for treating metabolic syndrome, any agent useful for treating a cardiovascular disease, cholesterol biosynthesis inhibitors, cholesterol absorption inhibitors, bile acid sequestrants, probucol derivatives, IBAT inhibitors, nicotinic acid receptor (NAR) agonists, ACAT inhibitors, cholesteryl ester transfer proton (CETP) inhibitors, low-density lipoprotein (LDL) activators, fish oil, water-soluble fibers, plant sterols, plant stanols, fatty acid esters of plant stanols, or any combination of two or more of these additional therapeutic agents.

Non-limiting examples of anti-obesity agents useful in the present methods for treating a Condition include CB1 antagonists or inverse agonists such as rimohabant, neuropeptide Y antagonists, MCR4 agonists, MCH receptor antagonists, histamine $H_3$ receptor antagonists or inverse agonists, metabolic rate enhancers, nutrient absorption inhibitors, leptin, appetite suppressants and lipase inhibitors.

Non-limiting examples of appetite suppressant agents useful in the present methods for treating or preventing a Condition include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramin ; glucagon-like peptide 1 (GLP-1) agonists; topiramate; and phytopharm compound 57.

Non-limiting examples of metabolic rate enhancers useful in the present methods for treating or preventing a Condition include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, arnrinone, milrinone, cilostamide, rolipram and cilomilast); thyroid hormone (3 agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens oleoyl-estrone); glucocorticoid antagonists; 11-beta hydroxy steroid dehydrogenase type 1 (11β HSD-1) inhibitors; melanocortin-3 receptor (Mc3r) agonists; and stearoyl-CoA desaturase-1 (SCD-1) compounds.

Non-limiting examples of nutrient absorption inhibitors useful in the present methods for treating or preventing a Condition include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Non-limiting examples of cholesterol biosynthesis inhibitors useful in the present methods for treating or preventing a Condition include HMG-CoA reductase inhibitors, squalene synthase inhibitors, squalene epoxidase inhibitors, and mixtures thereof.

Non-limiting examples of cholesterol absorption inhibitors useful in the present methods for treating or preventing a Condition include ezetimibe. In one embodiment, the cholesterol absorption inhibitor is ezetimibe.

HMG-CoA reductase inhibitors useful in the present methods for treating or preventing a Condition include, but are not limited to, statins such as lovastatin, pravastatin, fluvastatin, simvastatin, atorvastatin, cerivastatin, CI-981, resuvastatin, rivastatin, pitavastatin, rosuvastatin or L-659,699 ((E,E)-11-[3'R-(hydroxy-methyl)-4'-oxo-2'R-oxetanyl]-3,5,7R-trimethyl-2,4-undecadienoic acid).

Squalene synthesis inhibitors useful in the present methods for treating or preventing a Condition include, but are not limited to, squalene synthetase inhibitors; squalestatin 1; and squalene epoxidase inhibitors, such as NB-598 ((E)-N-ethyl-N-(6,6-dimethyl-2-hepten-4-ynyl)-3-[(3,3'-bithiophen-5-yl)methoxy]benzene-methanamine hydrochloride).

Bile acid sequestrants useful in the present methods for treating or preventing a Condition include, but are not limited to, cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bramodecane and (6-bromohexyl)-trimethylammonium bromide) which are available from Sankyo), water soluble derivatives such as 3,3-ioene, N—(Cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

Probucol derivatives useful in the present methods for treating or preventing a Condition include, but are not limited to, AGI-067 and others disclosed in U.S. Pat. Nos. 6,121,319 and 6,147,250.

IBAT inhibitors useful in the present methods for treating or preventing a Condition include, but are not limited to, benzothiepines such as therapeutic compounds comprising a 2,3,4,5-tetrahydro-1-benzothiepine 1,1-dioxide structure such as are disclosed in International Publication No. WO 00/38727.

Nicotinic acid receptor agonists useful in the present methods for treating or preventing a Condition include, but are not limited to, those having a pyridine-3-carboxylate structure or a pyrazine-2-carboxylate structure, including acid forms, salts, esters, zwitterions and tautomers, where available. Other examples of nicotinic acid receptor agonists useful in the present methods include nicotinic acid, niceritrol, nicofuranose and acipimox. An example of a suitable nicotinic acid product is NIASPAN® (niacin extended-release tablets) which are available from Kos Phai inaceuticals, Inc. (Cranbury, N.J.). Further nicotinic acid receptor agonists useful in the present methods for treating or preventing a Condition include, but are not limited to, the compounds disclosed in U.S. Patent Publication Nos. 2006/0264489 and 2007/0066630, and U.S. patent application Ser. No. 11/771,538, each of which is incorporated herein by reference.

ACAT inhibitors useful in the present methods for treating or preventing a Condition include, but are not limited to, avasimibe, HL-004, lecimibide and CL-277082 (N-(2,4-difluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 July; 60(1); 55-93, which is incorporated by reference herein.

CETP inhibitors useful in the present methods for treating or preventing a Condition include, but are not limited to, those disclosed in International Publication No. WO 00/38721 and U.S. Pat. No. 6,147,090, which are incorporated herein by reference.

LDL-receptor activators useful in the present methods for treating or preventing a Condition include, but are not limited to, include HOE-402, an imidazolidinyl-pyrimidine derivative that directly stimulates LDL receptor activity. See M. Huettinger at al., "Hypolipidemic activity of HOE-402 is Mediated by Stimulation of the LDL Receptor Pathway", *Arterioscler. Thromb.* 1993; 13:1005-12.

Natural water-soluble fibers useful in the present methods for treating or preventing a Condition include, but are not limited to, psyllium, guar, oat and pectin.

Fatty acid esters of plant stanols useful in the present methods for treating or preventing a Condition include, but are not limited to, the sitostanol ester used in BENECOL® margarine.

Non-limiting examples of antidiabetic agents useful in the present methods for treating diabetes or a diabetic complication include a sulfonylurea; an insulin sensitizer; a β-glucosidase inhibitor; an insulin secretagogue; a hepatic glucose output lowering agent; an anti-obesity agent as set forth above herein; a DPP-IV inhibitor; an antihypertensive agent; a meglitinide; an agent that slows or blocks the breakdown of starches and sugars in vivo; an histamine $H_3$ receptor antagonist; an antihypertensive agent, a sodium glucose uptake transporter 2 (SGLT-2) inhibitor; a peptide that increases insulin production; and insulin or any insulin-containing composition.

In one embodiment, the antidiabetic agent is a β-Glucosidase inhibitor. Non-limiting examples of β-Glucosidase inhibitors useful the present methods include miglitol, acarbose, and voglibose.

In one embodiment, the antidiabetic agent is an insulin sensitizer.

Non-limiting examples of insulin sensitizers include PPAR activators, such as the glitazone and thiazoldinedione class of agents, which include rosiglitazone, rosiglitazone maleate (AVANDIA™ from GlaxoSmithKline), pioglitazone, pioglitazone hydrochloride (ACTOS™, from Takeda) ciglitazone and MCC-555 (Mitstubishi Chemical Co.), troglitazone and englitazone; biguanides, such as phenformin, metformin, metformin hydrochloride (such as GLUCOPHAGE® from Bristol-Myers Squibb), metformin hydrochloride with glyburide (such as GLUCOVANCE™ from Bristol-Myers Squibb) and buformin; DPP-IV inhibitors, such as sitagliptin, saxagliptin (Januvia™, Merck), denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck); PTP-1B inhibitors; and glucokinase activators.

In another embodiment, the antidiabetic agent is a DPP-TV inhibitor.

Non-limiting examples of DPP-IV inhibitors useful in the present methods include sitagliptin, saxagliptin (Januvia™, Merck), denagliptin, vildagliptin (Galvus™, Novartis), alogliptin, alogliptin benzoate, ABT-279 and ABT-341 (Abbott), ALS-2-0426 (Alantos), ARI-2243 (Arisaph). BI-A and BI-B (Boehringer Ingelheim), SYR-322 (Takeda), MP-513

(Mitsubishi), DP-893 (Pfizer), RO-0730699 (Roche) or a combination of sitagliptin/metformin HCl (Janumet™, Merck).

In one embodiment, the antidiabetic agent is an insulin secretagogue.

In one embodiment, the insulin secretagogue is a sulfonylurea.

Non-limiting examples of sulfonylureas include glipizide, tolbutamide, glyburide, glimepiride, chlorpropamide, acetohexamide, gliamilide, gliclazide, glibenclamide and tolazamide.

In another embodiment, the insulin secretagogue is a meglitinide.

Non-limiting examples of meglitinides useful in the present methods for treating a Condition include repaglinide, mitiglinide, and nateglinide.

In still another embodiment, the insulin secretagogue is GLP-1 or a GLP-1 mimetic.

Non-limiting examples of GLP-1 mimetics useful in the present methods include Byetta-Exanatide, Liraglutinide, CJC-1131 (ConjuChem, Exanatide-LAR (Amylin), BIM-51077 (Ipsen/LaRoche), ZP-10 (Zealand Pharmaceuticals), and compounds disclosed in International Publication No. WO 00/07617.

Other non-limiting examples of insulin secretagogues useful in the present methods include exendin, GIP and secretin.

In one embodiment, the antidiabetic agent is a SGLT-2 inhibitor.

Non-limiting examples of SGLT-2 inhibitors useful in the present methods include dapagliflozin and sergliflozin, AVE2268 (Sanofi-Aventis) and T-1095 (Tanabe Seiyaku).

In another embodiment, the antidiabetic agent is a hepatic glucose output lowering agent.

Non-limiting examples of hepatic glucose output lowering agents include Glucophage and Glucophage XR.

In another embodiment, the antidiabetic agent is a of histamine $H_3$ receptor antagonist.

Non-limiting examples of histamine $H_3$ receptor antagonist agents include the following compound:

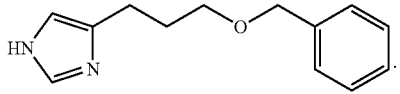 [SMILES: c1ccc(COCCCc2c[nH]cn2)cc1]

In another embodiment, the antidiabetic agent is insulin or an insulin-containing preparation.

The term "insulin" as used herein, includes all formulations of insulin, including long acting and short acting forms of insulin.

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the antidiabetic agent is anti-obesity agent.

Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat. Appetite suppressants are not considered to be within the scope of the anti-obesity agents useful in the present methods.

In another embodiment, the antidiabetic agent is an antihypertensive agent.

Non-limiting examples of antihypertensive agents useful in the present methods for treating diabetes include β-blockers and calcium channel blockers (for example diltiazem, verapamil, nifedipine, amlopidine, and myhefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

In still another embodiment, the antidiabetic agent is an agent that slows or blocks the breakdown of starches and sugars in vivo.

Non-limiting examples of antidiabetic agents that slow or block the breakdown of starches and sugars in vivo and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07611 (incorporated herein by reference).

Other specific additional therapeutic agents useful in the present methods for treating preventing a Condition include, but are not limited to, rimonabant, 2-methyl-6-(phenylethynyl)-pyridine, 3[(2-methyl-1,4-thiazol-4-yl)ethynyl]pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

In one embodiment, the present combination therapies for treating or preventing diabetes comprise administering a Bicyclic Heterocycle Derivative, an antidiabetic agent and/or an antiobesity agent.

In another embodiment, the present combination therapies for treating or preventing diabetes comprise administering a Bicyclic Heterocycle Derivative and an antidiabetic agent.

In another embodiment, the present combination therapies for treating or preventing diabetes comprise administering a Bicyclic Heterocycle Derivative and an anti-obesity agent.

In one embodiment, the present combination therapies for treating or preventing obesity comprise administering a Bicyclic Heterocycle Derivative, an antidiabetic agent and/or an antiobesity agent.

In another embodiment, the present combination therapies for treating or preventing obesity comprise administering a Bicyclic Heterocycle Derivative and an antidiabetic agent.

In another embodiment, the present combination therapies for treating or preventing obesity comprise administering a Bicyclic Heterocycle Derivative and an anti-obesity agent.

In one embodiment, the present combination therapies for treating or preventing metabolic syndrome comprise administering a Bicyclic Heterocycle Derivative and one or more additional therapeutic agents selected from: anti-obesity agents, antidiabetic agents, any agent useful for treating metabolic syndrome, any agent useful for treating a cardiovascular disease, cholesterol biosynthesis inhibitors, sterol absorption inhibitors, bile acid sequestrants, probucol derivatives, IBAT inhibitors, nicotinic acid receptor (NAR) agonists, ACAT inhibitors, cholesteryl ester transfer proton (CETP) inhibitors, low-density lipoprotein (LDL) activators, fish oil, water-soluble fibers, plant sterols, plant stanols and fatty and esters of plant stanols.

In one embodiment, the additional therapeutic agent is a cholesterol biosynthesis inhibitor. In another embodiment, the cholesterol biosynthesis inhibitor is a squalene synthetase inhibitor. In another embodiment, the cholesterol biosynthesis inhibitor is a squalene epoxidase inhibitor. In still another embodiment, the cholesterol biosynthesis inhibitor is an HMG-CoA reductase inhibitor. In another embodiment, the HMG-CoA reductase inhibitor is a statin. In yet another embodiment, the statin is lovastatin, pravastatin, simvastatin or atorvastatin.

In one embodiment, the additional therapeutic agent is a cholesterol absorption inhibitor. In another embodiment, the cholesterol absorption inhibitor is ezetimibe.

In one embodiment, the additional therapeutic agent comprises a cholesterol absorption inhibitor and a cholesterol biosynthesis inhibitor. In another embodiment, the additional therapeutic agent comprises a cholesterol absorption inhibitor and a statin. In another embodiment, the additional therapeutic agent comprises ezetimibe and a statin. In another embodiment, the additional therapeutic agent comprises ezetimibe and simvastatin.

In one embodiment, the present combination therapies for treating or preventing metabolic syndrome comprise administering a Bicyclic Heterocycle Derivative, an antidiabetic agent and/or an antiobesity agent.

In another embodiment, the present combination therapies for treating or preventing metabolic syndrome comprise administering a Bicyclic Heterocycle Derivative and an antidiabetic agent.

In another embodiment, the present combination therapies for treating or preventing metabolic syndrome comprise administering a Bicyclic Heterocycle Derivative and an anti-obesity agent.

In one embodiment, the present combination therapies for treating or preventing a cardiovascular disease comprise administering one or more Bicyclic Heterocycle Derivatives, and an additional agent useful for treating or preventing a cardiovascular disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Bicyclic Heterocycle Derivatives are administered during a time when the additional therapeutic agent(s) exert their prophylactic or therapeutic In another embodiment, the one or more Bicyclic Heterocycle Derivatives and the additional therapeutic agent(s) are administered in doses commonly employed when such agents are used as monotherapy for treating a Condition.

In another embodiment, the one or more Bicyclic Heterocycle Derivatives and the additional therapeutic agent(s) are administered in doses lower than the doses commonly employed when such agents are used as monotherapy for treating a Condition.

In still another embodiment, the one or more Bicyclic Heterocycle Derivatives and the additional therapeutic agent(s) act synergistically and are administered in doses lower than the doses commonly employed when such agents are used as monotherapy for treating a Condition.

In one embodiment, the one or more Bicyclic Heterocycle Derivatives and the additional therapeutic agent(s) are present in the same composition. In one embodiment, this composition is suitable for oral administration. In another embodiment, this composition is suitable for intravenous administration.

The one or more Bicyclic Heterocycle Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Bicyclic Heterocycle Derivatives and the additional therapeutic agent(s) may inhibit the resistance of a Condition to these agents.

In one embodiment, when the patient is treated for diabetes or a diabetic complication, the additional therapeutic agent is an antidiabetic agent which is not a Bicyclic Heterocycle Derivative. In another embodiment, the additional therapeutic agent is an agent useful for reducing any potential side effect of a Bicyclic Heterocycle Derivative. Such potential side effects include, but are not limited to, nausea, vomiting, headache, fever, lethargy, muscle-aches, diarrhea, general pain, and pain at an injection site.

In one embodiment, the additional-therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Bicyclic Heterocycle Derivative(s) and the other agent(s) for treating diseases or conditions listed above can be administered simultaneously or sequentially. This particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Bicyclic Heterocycle Derivatives and the additional therapeutic agent(s)can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Compositions and Administration

In one embodiment, the invention provides compositions comprising an effective amount of one or more Bicyclic Heterocycle Derivatives or a pharmaceutically acceptable salt, solvate, ester or prodrug thereof, and a pharmaceutically acceptable carrier.

For preparing compositions comprising one or more Bicyclic Heterocycle Derivatives, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the fowl of creams, lotions, aerosols and/or emulsions and can be included in a transdermal patch of the matrix or reservoir type as are conventional in the art for this purpose.

In one embodiment, a Bicyclic Heterocycle Derivative is administered orally. In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, the condition and size of the patient, as well as severity of the symptoms being treated. A typical recommended daily dosage regimen for oral administration can range from about 1 mg/day to about 1000 mg/day, 1 mg/day to about 500 mg/day, 1 mg/day to about 300 mg/day, 1 mg/day to about 75 mg/day, 1 mg/day to about 50 mg/day, or 1 mg/day to about 20 mg/day, in one dose or in two to four divided doses.

When the invention comprises a combination of one or more Bicyclic Heterocycle Derivatives and an additional therapeutic agent, the two active components may be co-administered simultaneously or sequentially, or a single composition comprising one or more Bicyclic Heterocycle Derivatives and the additional therapeutic agent(s) in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of an advantageous effect of the combination.

In one embodiment, the components of a combination therapy regimen are to be administered simultaneously, they can be administered in a single composition with a pharmaceutically acceptable carrier.

In another embodiment, when the components of a combination therapy regimen are to be administered separately or sequentially, they can be administered in separate compositions, each containing a pharmaceutically acceptable carrier.

Kits

In one aspect, the present invention provides a kit comprising an effective amount of one or more Bicyclic Heterocycle Derivatives, or a pharmaceutically acceptable salt, solvate, ester or prodrug thereof, and a pharmaceutically acceptable carrier.

In another aspect the present invention provides a kit comprising an amount of one or more Bicyclic Heterocycle Derivatives, or a pharmaceutically acceptable salt, solvate, ester or prodrug thereof, and an amount of at least one additional therapeutic agent listed above, wherein the combined amounts are effective for treating or preventing a Condition in a patient.

When the components of a combination therapy regimen are to be administered in more than one composition, they can be provided in a kit comprising a single package containing one or more containers, wherein one container contains one or more Bicyclic Heterocycle Derivatives in a pharmaceutically acceptable carrier, and a second, separate container comprises an additional therapeutic agent in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

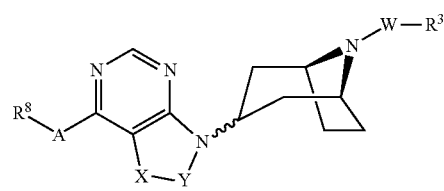

or a pharmaceutically acceptable salt thereof,
wherein:
  A is —O— or —N(R$^{12}$)—;
  W is —C(O)O—, —C(O)— or —S(O)$_2$—;
  —X—Y is CH$_2$—CH$_2$ or CH=CH;
  R$^3$ is alkyl, haloalkyl or cycloalkyl, wherein the cycloalkyl group can be optionally substituted with up to 4 substituents each independently selected from the group consisting of: alkyl and halo;
  each occurrence of R$^7$ is independently H or alkyl;
  R$^8$ is aryl or heteroaryl, optionally substituted with R$^9$;
  R$^9$ represents from 1-4 optional substituents, which can be the same or different, selected from alkyl, alkenyl, alkynyl, halo, haloalkyl, —CN, —NO$_2$, —O-(alkylene)$_t$-R$^{13}$, —S-(alkylene)$_t$-R$^{13}$, —N(R$^{13}$)-(alkylene)$_t$-R$^{13}$, -(alkylene)$_t$-R$^{13}$, —C(O)-(alkylene)$_t$-R$^{13}$, —C(O)O-(alkylene)$_t$-R$^{13}$, —N(R$^7$)C(O)-(alkylene)$_t$-R$^{13}$, —C(O)N(R$^7$)-(alkylene)$_t$-R$^{13}$, —OC(O)-(alkylene)$_t$-R$^{13}$, —N(R$^7$)C(O)N(R$^7$)-(alkylene)$_t$-R$^{13}$, —N(R$^7$)C(O)O-(alkylene)$_t$-R$^{13}$, —S(O)-(alkylene)$_t$-R$^{13}$ or —S(O)$_2$(alkylene)$_t$-R$^{13}$;
  R$^{12}$ is H, alkyl or aryl;
  each occurrence of R$^{13}$ is independently H, haloalkyl, aryl, cycloalkyl, cycloalkenyl, heterocycloalkyl, heterocycloalkenyl or heteroaryl; and
  each occurrence of t is independently 0 or 1.

2. The compound of claim 1 having the structure:

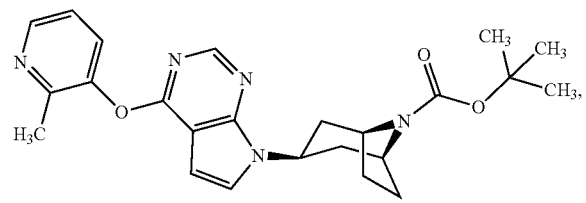

-continued

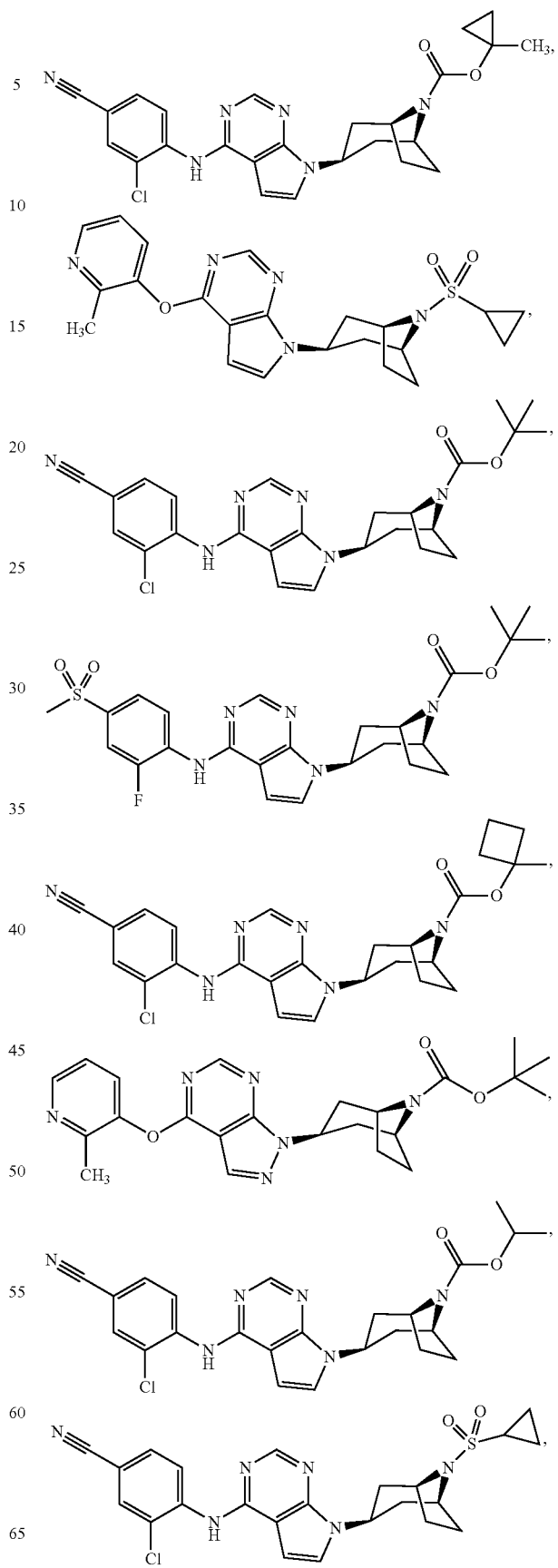

87
-continued

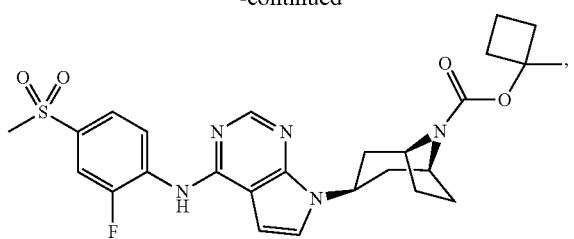

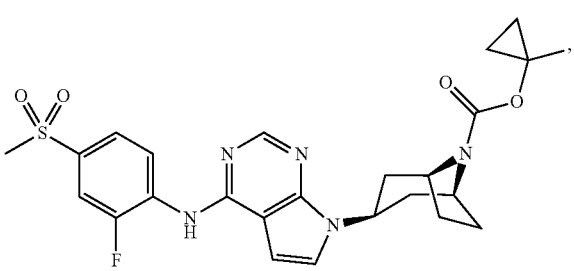

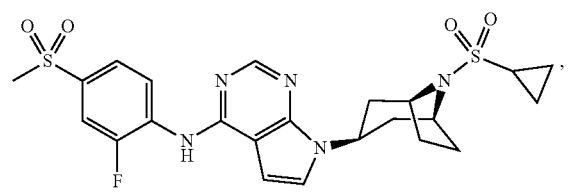

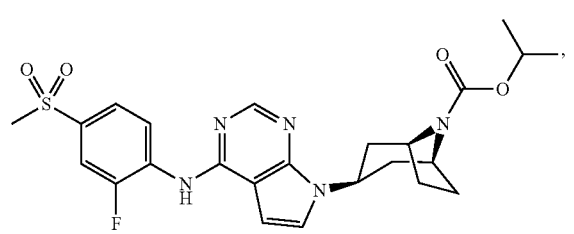

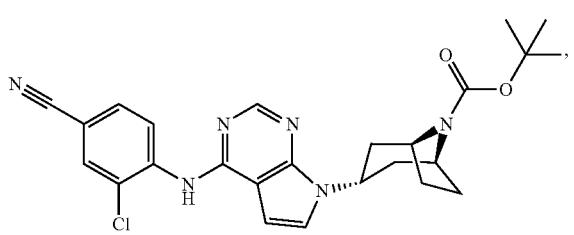

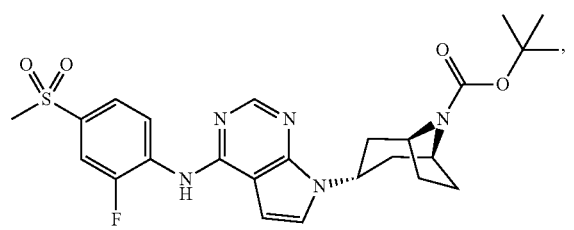

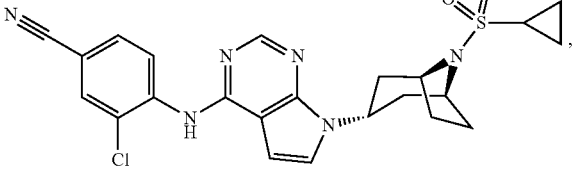

88
-continued

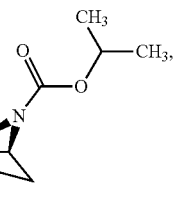

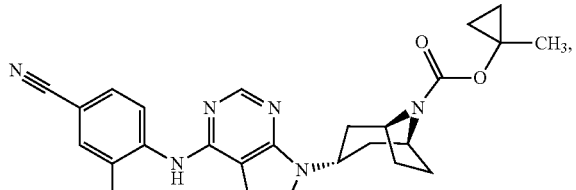

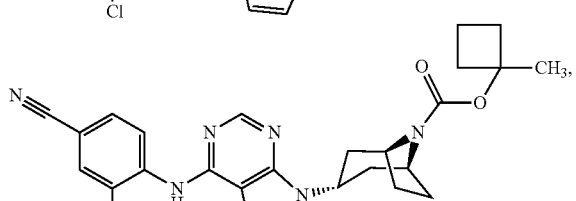

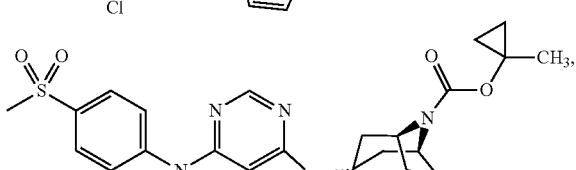

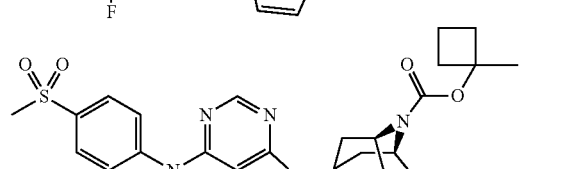

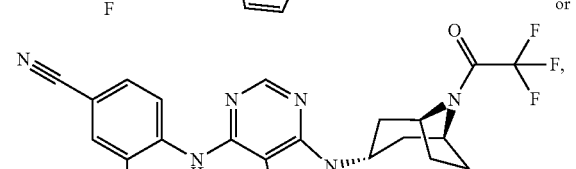

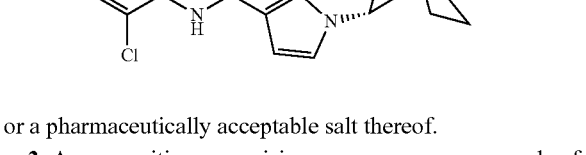

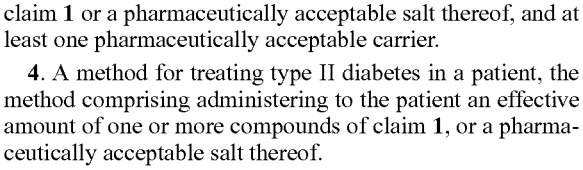 or

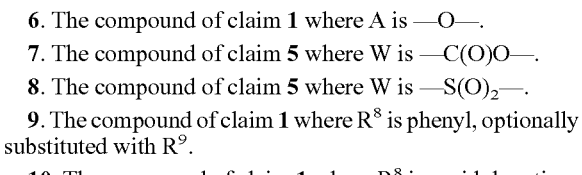

or a pharmaceutically acceptable salt thereof.

3. A composition comprising one or more compounds of claim 1 or a pharmaceutically acceptable salt thereof, and at least one pharmaceutically acceptable carrier.

4. A method for treating type II diabetes in a patient, the method comprising administering to the patient an effective amount of one or more compounds of claim 1, or a pharmaceutically acceptable salt thereof.

5. The compound of claim 1 where A is —NH—.

6. The compound of claim 1 where A is —O—.

7. The compound of claim 5 where W is —C(O)O—.

8. The compound of claim 5 where W is —S(O)$_2$—.

9. The compound of claim 1 where $R^8$ is phenyl, optionally substituted with $R^9$.

10. The compound of claim 1 where $R^8$ is pyridyl, optionally substituted with $R^9$.

11. The compound of claim 9 where $R^3$ is cyclopropyl or cyclobutyl, optionally substituted with up to 4 substituents each independently selected from the group consisting of: alkyl and halo.

12. The compound of claim 9 where $R^3$ is isopropyl or t-butyl.

13. The compound of claim 1 where $R^9$ is independently selected from alkyl, halo, —CN, cycloalkyl, alkynyl, heteroaryl, —S(O)$_2$-alkyl, or S(O)$_2$-cycloalkyl.

14. The compound of claim 1 where $R^9$ is independently selected from methyl, F, Cl, —CN, , or —S(O)$_2$CH$_3$.

15. The compound of claim 1 where $R^8$ is phenyl, substituted with 1 or 2 groups, each independently selected from halo, —CN or —S(O)$_2$-alkyl.

16. The compound of claim 1 where $R^8$ is heteroaryl, which is substituted with 1 or 2 groups, each independently selected from alkyl or heteroayl.

\* \* \* \* \*